US012161729B2

(12) United States Patent
Nguyen et al.

(10) Patent No.: US 12,161,729 B2
(45) Date of Patent: Dec. 10, 2024

(54) METHODS AND COMPOSITIONS FOR VISUALIZING A URETER IN A SURGICAL PROCEDURE

(71) Applicant: ALUME BIOSCIENCES, INC., San Diego, CA (US)

(72) Inventors: Quyen Nguyen, San Diego, CA (US); Michael Whitney, San Diego, CA (US)

(73) Assignee: ALUME BIOSCIENCES, INC., San Diego, CA (US)

( * ) Notice: Subject to any disclaimer, the term of this patent is extended or adjusted under 35 U.S.C. 154(b) by 0 days.

(21) Appl. No.: 18/349,833

(22) Filed: Jul. 10, 2023

(65) Prior Publication Data

US 2023/0338585 A1 Oct. 26, 2023

Related U.S. Application Data

(63) Continuation of application No. PCT/US2022/012379, filed on Jan. 13, 2022.

(60) Provisional application No. 63/137,621, filed on Jan. 14, 2021.

(51) Int. Cl.
*A61K 49/00* (2006.01)
*C07K 7/06* (2006.01)
*C07K 7/08* (2006.01)

(52) U.S. Cl.
CPC ...... *A61K 49/0056* (2013.01); *A61K 49/0021* (2013.01); *A61K 49/0043* (2013.01); *C07K 7/06* (2013.01); *C07K 7/08* (2013.01)

(58) Field of Classification Search
CPC ............ A61K 49/0056; A61K 49/0021; A61K 49/0043; C07K 7/06; C07K 7/08; G01N 33/5005
See application file for complete search history.

(56) References Cited

U.S. PATENT DOCUMENTS

| | | | |
|---|---|---|---|
| 4,439,356 A | 3/1984 | Khanna et al. | |
| 4,452,720 A | 6/1984 | Harada et al. | |
| 4,496,542 A | 1/1985 | Skiles et al. | |
| 4,659,839 A | 4/1987 | Nicolotti et al. | |
| 5,066,580 A | 11/1991 | Lee | |
| 5,227,487 A | 7/1993 | Haugland et al. | |
| 5,543,295 A | 8/1996 | Bronstein et al. | |
| 5,750,409 A | 5/1998 | Herrmann et al. | |
| 5,936,087 A | 8/1999 | Benson et al. | |
| 6,008,379 A | 12/1999 | Benson et al. | |
| 6,025,505 A | 2/2000 | Lee et al. | |
| 6,080,852 A | 6/2000 | Lee et al. | |
| 8,685,372 B2 | 4/2014 | Tsien et al. | |
| 9,072,773 B2 | 7/2015 | Gonzalez et al. | |
| 9,353,154 B2 | 5/2016 | Gonzalez et al. | |
| 2012/0148499 A1 | 6/2012 | Tsien et al. | |
| 2014/0010861 A1 | 1/2014 | Bancel et al. | |
| 2014/0276008 A1 | 9/2014 | Steinbach et al. | |
| 2017/0157208 A1 | 6/2017 | Eyer et al. | |
| 2018/0043037 A1* | 2/2018 | Dalma-Weiszhausz | A61K 49/0043 |

FOREIGN PATENT DOCUMENTS

WO 2010/121023 A2 10/2010
WO 2019/028281 A2 2/2019

OTHER PUBLICATIONS

Altschul et al., "Gapped BLAST and PSI-BLAST: a new generation of protein database search programs," *Nucleic Acids Research* 25(17):3389-3402, 1997.
Barth et al., "Direct Administration of Nerve-Specific Contrast to Improve Nerve Sparing Radical Prostatectomy," *Theranostics* 7(3):573-593, Jan. 2017.
Borsook et al., "Surgically-Induced Neuropathic Pain (SNPP): Understanding the Perioperative Process," Annals of surgery. 257:403-412, Mar. 2013.
Chames et al., "Therapeutic antibodies: successes, limitations and hopes for the future," *British Journal of Pharmacology* 157:220-233, Jan. 2009.
Cherrick et al., "Indocyanine green: observations on its physical properties, plasma decay, and hepatic extraction," *Journal of Clinical Investigation* 39(4):592-600, Apr. 1960.
Chitchian et al., "Combined image-processing algorithms for improved optical coherence tomography of prostate nerves," *Journal of Biomedical Optics* 15(4), Jul./Aug. 2010. (6 pages).
Cotero et al., "Intraoperative Fluorescence Imaging of Peripheral and Central Nerves Through a Myelin-Selective Contrast Agent," *Mol Imaging Biol* 14:708-717, Apr. 10, 2012.
Cotero et al., "Improved Intraoperative Visualization of Nerves through a Myelin-Binding Fluorophore and Dual-Mode Laparoscopic Imaging," *PLoS One* 10(6):0130276, Jun. 15, 2015.
D'Amico et al., "Biochemical Outcome After Radical Prostatectomy, External Beam Radiation Therapy, or Interstitial Radiation Therapy for Clinically Localized Prostate Cancer," *JAMA* 280(11):969-974, Sep. 16, 1998.
Descotes, "Immunotoxicity of monoclonal antibodies," *mAbs* 1(2):104-111, Mar./Apr. 2009.
GenBank "PREDICTED: uncharacterized protein LOC108770849 [Trachymyrmex cornetzi]," National Center for Biotechnology Information Reference Sequence: XP_018378085.1, Sep. 23, 2016. (2 pages) URL: <https://www.ncbi.nlm.nih.gov/protein/XP_018378085.1?report-genbank&logS-protalign&blast rank=1&RID=Y1C8WUYGO1 R>.
Gibbs et al., "Structure-activity relationship of nerve-highlighting fluorophores," PLoS One 8(9)(e73493), Sep. 2013. (12 pages).
Gibbs-Strauss et al., "Nerve-highlighting fluorescent contrast agents for image-guided surgery," Mol Imaging 10(2):91-101, Apr. 2011.
Glasgow "Design and Selection of Probes for In Vivo Molecular Targeting and Imaging," A Dissertation in Biomedical Sciences, University of California, San Diego, 2015. (220 pages).
Glasgow et al., "Laminin targeting of a peripheral nerve-highlighting peptide enables degenerated nerve visualization," PNAS 113(45):12774-12779, Nov. 8, 2016.

(Continued)

*Primary Examiner* — Michael G. Hartley
*Assistant Examiner* — Leah H Schlientz
(74) *Attorney, Agent, or Firm* — Seed IP Law Group LLP

(57) ABSTRACT

Methods for visualizing a ureter, including fluorescent visualization of a ureter, as well as other target tissues, during a surgical procedure, comprising administering to a subject a fluorescent conjugate comprising a peptide and a fluorescent moiety.

29 Claims, 1 Drawing Sheet

Specification includes a Sequence Listing.

(56) References Cited

OTHER PUBLICATIONS

Gray et al., "Compact Fluorescence and White Light Imaging System for Intraoperative Visualization of Nerves," *Proc SPIE* 8207, Feb. 3, 2012. Author's Manuscript. (11 pages).
Hackman et al., "Polymeric Micelles as Carriers for Nerve-Highlighting Fluorescent Probe Delivery," *Mol Pharmaceutics* 12:4386-4394, Oct. 20, 2015.
Hingorani et al., "Nerve-targeted probes for fluorescence-guided intraoperative imaging," *Theranostics* 8(15):4226-4237, Jul. 30, 2018.
Hussain et al., "Fluorescently labeled peptide increases identification of degenerated facial nerve branches during surgery and improves functional outcome," *PloS one* 10(3):(0119600), Mar. 9, 2015. (13 pages).
International Search Report with Written Opinion corresponding to International Patent Application No. PCT/US2018/045054, dated Dec. 26, 2018, 13 pages.
Lee et al., "Aptamer database," *Nucleic Acids Research* 32:D95-D100, Jan. 2004.
Lim et al., "Peripheral Nerve Injury Induces Persistent Vascular Dysfunction and Endoneurial Hypoxia, Contributing to the Genesis of Neuropathic Pain," Journal of Neuroscience 35(8):3346-3359, Feb. 25, 2015.
Liu et al., "Rapid fluorescence imaging of spinal cord following epidural administration of a nerve-highlighting fluorophore," *Theranostics* 7(7):1863-1874, Apr. 10, 2017.
Marques et al., "Imaging neuromuscular junctions by confocal fluorescence microscopy: individual endplates seen in whole muscles with vital intracellular staining of the nerve terminals," *J. Anat.* 192:425-430, 1998.
Marshall et al., "Near-infrared fluorescence imaging in humans with indocyanine green: a review and update," *Open Surg Oncol J* 2(2):12-25, 2010.
Massaad et al., "Fluorescently-tagged anti-ganglioside antibody selectively identifies peripheral nerve in living animals," *Scientific Reports* 5(15766), Oct. 2015. (11 pages).
Naskar et al., "Detection of early neuron degeneration and accompanying microglial responses in the retina of a rat model of glaucoma," Investigative Ophthalmology & Visual Science 43(9):2962-2968, Sep. 2002.
Nelson et al., "Back to Baseline: Erectile Function Recovery after Radical Prostatectomy from the Patients' Perspective," J Sex Med. 10(6):1636-1643, Jun. 2013.
Papworth et al., "In vivo fibre optic confocal imaging of microvasculature and nerves in the rat vas deferens and colon," *J. Anat.* 192(Pt4):489-495, May 1998.
Park et al., "Prototype nerve-specific near-infrared fluorophores," *Theranostics* 4(8): 823-833, Jun. 7, 2014.
Stankoff et al., "Imaging of CNS myelin by positron-emission tomography," *PNAS* 103(24):9304-9309, Jun. 13, 2006.
Tanaka et al., "Real-Time Intraoperative Ureteral Guidance Using Invisible Near-Infrared Fluorescence," *The Journal of Urology* 178:2197-2202, Nov. 2007.
Van Der Meijden et al., "The value of haptic feedback in conventional and robot-assisted minimal invasive surgery and virtual reality training: a current review," *Surg Endosc.* 23:1180-1190, Jan. 2009.
Verbeek et al., "Near-Infrared Fluorescence Imaging of Both Colorectal Cancer and Ureters Using a Low-Dose Integrin Targeted Probe," *Ann Surg Oncol* 21:S528-S537, Feb. 11, 2014.
Walsh "Anatomic radical prostatectomy: evolution of the surgical technique," *The Journal of Urology* 160:2418-2424, Dec. 1998.
Wang et al., "Design, Synthesis, and Evaluation of Coumarin-based Molecular Probes for Imaging of Myelination," *J Med Chem.* 54(7):2331-2340, Apr. 14, 2011.
Wang et al., "Longitudinal near-infrared imaging of myelination," *J Neurosci.* 31(7):2382-2390, Feb. 16, 2011.
Woltmann et al., "Anatomosurgical study of the marginal mandibular branch of the facial nerve for submandibular surgical approach," *Braz Dent J.* 17(1):71-74, 2006.
Wu et al., "Improved facial nerve identification with novel fluorescently labeled probe," *The Laryngoscope* 121(4):805-810, Apr. 2011.
Dip et al., "Novel technique for identification of ureters using sodium fluorescein," *Surgical Endoscopy* 28:2730-2733, Apr. 2014. (4 pages).
Lee et al., "Use of Indocyanine Green During Robot-assisted Ureteral Reconstructions," *European Urology* 67:291-298, Feb. 2015. (8 pages).
Mahalingam et al., "Intraoperative Ureter Visualization Using a Novel Near-Infrared Fluorescent Dye," *Molecular Pharmaceutics* 15:3442-3447, Jul. 2018. (6 pages).
Rajanbabu et al., "Ureteric mapping with Indocyanine green: A new tool to prevent ureteral injury in complex gynecological surgery," *Journal of Endometriosis and Pelvic Pain Disorders* 12(3-4):190-192, Jul. 2020. (3 pages).
Cabanes et al., "Intra-operative identification of ureters using indocyanine green for gynecological oncology procedures," *International Journal of Gynecological Cancer* 30:278, 2020 [Published online Nov. 2019]. (1 page).
Chen et al., "Determination of fluorescein and fluorescein monoglucuronide excreted in urine," *Chemical and Pharmaceutical Bulletin* 28(9):2812-2816, Sep. 1980. (5 pages).
Cherrick et al., "Indocyanine Green: Observations on its Physical Properties, Plasma Decay, and Hepatic Extraction," *Journal of Clinical Investigation* 39(4):592-600, Apr. 1960. (10 pages).
Mahalingam et al., "Design of a Near Infrared Fluorescent Ureter Imaging Agent for Prevention of Ureter Damage during Abdominal Surgeries," *Molecules* 26:3739, Jun. 2021. (11 pages).
Meershoek et al., "Multispectral-Fluorescence Imaging as a Tool to Separate Healthy from Disease-Related Lymphatic Anatomy During Robot-Assisted Laparoscopy," *Journal of Nuclear Medicine* 59:1757-1760, May 2018. (4 pages).
Siddighi et al., "Indocyanine green for intraoperative localization of ureter," *American Journal of Obstetrics & Gynecology* 211:436.e1-436.e2, Oct. 2014. (2 pages).
Slooter et al., "Currently available and experimental dyes for intraoperative near-infrared fluorescence imaging of the ureters: a systematic review," *Techniques in Coloproctology* 23:305-313, Apr. 2019. (9 pages).
Cision PR Network, URL=https://www.prnewswire.com/news-releases/alume-biosciences-granted-fda-fast-track-designation-of-alm-488-for-surgical-nerve-visualization-301289360.html, May 12, 2021, download date Aug. 16, 2023. (4 pages).
Cision PR Network, URL=https://www.prnewswire.com/news-releases/us-fda-allows-trial-to-proceed-for-alume-biosciences-nerve-imaging-candidate-301051743.html, May 4, 2020, download date Aug. 16, 2023. (5 pages).
De Proost et al., "Selective visualisation of sensory receptors in the smooth muscle layer of ex-vivo airway whole-mounts by styryl pyridinium dyes," *Cell and tissue research* 329:421-431, May 24, 2007.
Ebraheim et al., "Vulnerability of the recurrent laryngeal nerve in the anterior approach to the lower cervical spine," *Spine* 22(22):2664-2667, 1997.
Gaillard et al., "Facial nerve dysfunction after parotidectomy: the role of local factors," *Laryngoscope* 115(2):287-291, Feb. 2005.
Gallina et al., "Surgery and Erectile Dysfunction," *Arch Esp. Urol.* 63(8):640-648, 2010.
Gantz "Intraoperative facial nerve monitoring," *Am J Otol* 11:58-61, Nov. 1985.
Gosain et al., "The Temporal Branch of the Facial Nerve: How Reliably Can We Predict Its Path?" *Plast Reconstr Surg.* 99(4):1224-1233, Apr. 1997.
Guillonneau "Préservation neurologique et vasculaire au cours de la prostatectomie totale laparoscopique," *Prog Urol* 19(Suppl 4):S180-S182, 2009. (with English Abstract).
Haller et al., "Clinically Relevant Anatomy of Recurrent Laryngeal Nerve," *Spine* 37(2):97-100, 2012.

(56) References Cited

OTHER PUBLICATIONS

International Search Report and Written Opinion, mailed May 12, 2022, for International Application No. PCT/US2022/012379, 18 pages.
Kaltenbronn et al., "Synthesis of a saralasin derivative completely modified at every amide bond with a methyleneamino isostere," Proceedings of the 11th American Peptide Symposium. Peptides: Chemistry, Structure and Biology. 1:969-970, 1990. (5 pages).
Karam et al., "The precise location and nature of the nerves to the male human urethra: histological and immunohistochemical studies with three-dimensional reconstruction," *Eur Urol* 48:858-864, Mar. 2005.
Köbbert et al., "Current concepts in neuroanatomical tracing," *Progress in Neurobiology* 62(4):327-351, 2000.
Koehler et al., "Erectile dysfunction after radical prostatectomy: the impact of nerve-sparing status and surgical approach," *International Journal of Impotence Research*. 24:155-160, May 3, 2012.
Kübler et al., "Impact of Nerve Sparing Technique on Patient Self-Assessed Outcomes After Radical Perineal Prostatectomy," *The Journal of Urology* 178:488-492, Aug. 2007.
Lineaweaver et al., "Microsurgical Anatomy of the Facial Nerve," *J Craniofac Surg* 8(1):6-10, Jan. 1997.
Marangos et al., "In vivo visualization of the cochlear nerve and nuclei with fluorescent axonal tracers," *Hearing Research* 162:48-52, 2001.
Miller et al., "Identification and Monitoring of the Recurrent Laryngeal Nerve During Thyroidectomy," *Surgical Oncology Clinics of North America* 17:121-144, 2008.
Nandipati et al., "Nerve-Sparing Surgery Significantly Affects Long-Term Continence After Radical Prostatectomy," *Urology* 70(6):1127-1130, 2007.
Nason et al., "Clinical observations of the anatomy and function of the marginal mandibular nerve," *International Journal of Oral and Maxillofacial Surgery* 36:712-715, Mar. 2007.
Nguyen et al., "Fluorescence-guided surgery with live molecular navigation—a new cutting edge," *Nature Reviews Cancer* 13(9):653-662, Sep. 2013. (HHS Public Access Author Manuscript, available in PMC May 11, 2015) (23 pages).
O'Malley et al., "Fluorescent Retrograde Axonal Tracing of the Facial Nerve," *Laryngoscope* 116:1792-1797, Oct. 2006.
Richmond et al., "Efficacy of seven retrograde tracers, compared in multiple-labelling studies of feline motoneurones," *Journal of Neuroscience Methods* 53:35-46, 1994.
Rosenthal et al., "Vocal Fold Immobility: A Longitudinal Analysis of Etiology Over 20 years," *Laryngoscope* 117:1864-1870, Oct. 2007.
Schaumburg et al., "Structural and functional investigations of the murine cavernosal nerve: a model system for serial spatio-temporal study of autonomic neuropathy," *BJU Int.* 99:916-924, 2007.
Stanford et al., "Urinary and Sexual Function After Radical Prostatectomy for Clinically Localized Prostate Cancer: the Prostate Cancer Outcomes Study," *Jama* 283(3):354-360, Jan. 19, 2000.
Tewari et al., "An Operative and Anatomic Study to Help in Nerve Sparing During Laparoscopic and Robotic Radical Prostatectomy," *Eur Urol.* 43:444-454, 2003.
Tzafetta et al., "Essays on the Facial Nerve: Part I. Microanatomy," *Plast Reconstr Surg.* 125:879-889, Mar. 2010.
Wagner et al., "Near-Infrared Fluorescence Imaging Can Help Identify the Contralateral Phrenic Nerve During Robotic Thymectomy," *Ann Thorac Surg.* 94:622-625, 2012.
Walsh "Radical Prostatectomy for Localized Prostate Cancer Provides Durable Cancer Control With Excellent Quality of Life: a Structured Debate," *The Journal of Urology.* 163:1802-1807, Jun. 2000.
Walsh et al., "Fluorescence Imaging of Nerves During Surgery," *Annals of Surgery*, 2019. (8 pages).
Walz et al., "A Critical Analysis of the Current Knowledge of Surgical Anatomy Related to Optimization of Cancer Control and Preservation of Continence and Erection in Candidates for Radical Prostatectomy," *European Urology* 57:179-192, 2010.
Walz et al., "Basic principles of anatomy for optimal surgical treatment of prostate cancer," *World J Urol.* 25:31-38, Feb. 2007.
Whitney "Fluorescent peptides highlight peripheral nerves during surgery in mice," *Nature Biotechnology* 29(4):352-356, Apr. 2011. (HHS Public Access Author Manuscript, available in PMC May 30, 2012 ) (12 pages).
Witt "Comparing the Long-Term Outcome of Immediate Postoperative Facial Nerve Dysfunction and Vocal Fold Immobility After Parotid and Thyroid Surgery," *J Voice* 20(3):461-465, 2006.
Yamashita et al., "Nerve injury-related erectile dysfunction following nerve-sparing radical prostatectomy: A novel experimental dissection model," *Int J Urol.* 16:905-911, Sep. 22, 2009.
Zhao et al., "Robotics in urologic surgery," *Minerva Urol Nefrol* 61(4):331-339, 2009.
Zhivov et al., "Real-time mapping of the subepithelial nerve plexus by in vivo confocal laser scanning microscopy," *Br J Ophthalmol* 94:1133-1135, 2010.
U.S. Appl. No. 17/767,847, filed Apr. 8, 2022.
U.S. Appl. No. 18/254,565, filed May 25, 2023.

\* cited by examiner

Rodent model 2 hours post intravenous administration of fluorescent conjugate
(SEQ ID NO:747)
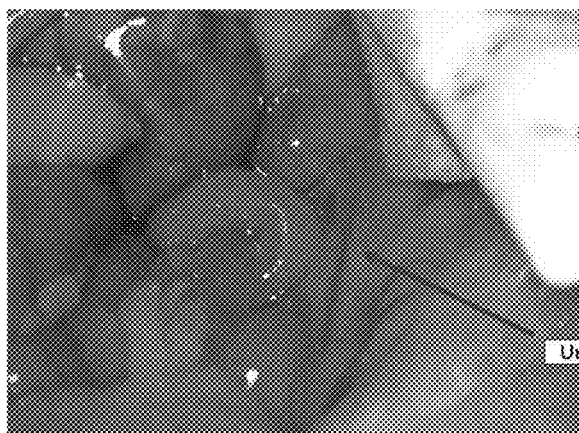
White Light Image            Fluorescent Contrast Overlay

METHODS AND COMPOSITIONS FOR VISUALIZING A URETER IN A SURGICAL PROCEDURE

REFERENCE TO AN ELECTRONIC SEQUENCE LISTING

The contents of the electronic sequence listing (405C1_SeqListing.xml; Size: 915 kilobytes; and Date of Creation: Jun. 29, 2023) is herein incorporated by reference in its entirety.

FIELD

The present invention relates generally to intraoperative imaging methods, and more particularly, to fluorescent visualization of ureters, as well as nerves, during surgical procedures.

BACKGROUND

Ureters comprise a pair of multilayer muscular tubes—each about 10 to 12 inches long in an average adult—that transport urine from the kidneys to the bladder. Transport relies on peristaltic motion, arising from contractions in the muscular layer of the ureteral wall initiated by pacemakers. As the walls rhythmically tighten and relax, urine flows in a pulsatile motion through the ureters to the bladder.

Because they extend from the abdomen to the pelvis, ureters are in close proximity to many structures in the abdominopelvic cavity, such as gonadal and uterine vessels, iliac arteries, inferior mesenteric and sigmoid vessels, as well as the cervix, colon, and rectum. In addition, ureters are thin-walled tubes that are often in a collapsed state and are difficult to distinguish from surrounding tissue. Given their location and physical attributes, ureters are at significant risk of injury in many surgeries, including gynecological, urological, colorectal, and cardiovascular surgical procedures. See, e.g., Engelsgjerd and LaGrange, 2020, StatPearls, *Treasure Island (FL): StatPearls Publishing;* 2020 Jul. 10; Ferrara and Kann, 2019, *Clin. Colon Rectal Surg.* 32, 196-203; Ahn et al., 2019, *Quant. Imaging Med. Surg.* 9,1056-1065; Gild et al., 2018, *Asian J. Urol.* 5, 101-106. Indeed, ureteral injuries are often not noticed intraoperatively, resulting in delayed diagnoses and late treatments that in some cases can lead to long term complications such as kidney failure. Tan-Kim et al. 2015, *J. Minimally Invasive Gynecol.* 22, 1278-1286; Al-Awadi et al. 2005, *Int. Urol. Nephrol.* 37, 235-241.

Consequently, ureteral injuries significantly impact patient morbidity and concomitant healthcare costs. In the United States, about 600 thousand hysterectomies and 300 thousand colon surgeries are performed annually, with a ureteral injury rate as high as 2.5% and 7.6%, respectively. See Gild et al. 2018, *Asian J. Urol.* 5, 101-106; Doll et al. 2016, *JAMA Surg.* 151, 876-877; Teeluckdharry et al. 2015, *Obstet. Gynecol.* 126, 1161-1169; Briggs and Goldberg, 2011, *Clin. Colon. Rectal Surg.* 30, 130-135. In lower abdominal surgical procedures, iatrogenic ureteral injuries (IUIs) have estimated incidence rates ranging from 0.5-1% for cancer surgery, 0.3% to 2.5% for laparoscopic gynecological surgery, and up to 10% for gynecologic oncologic surgery. See, e.g., de Valk et al. 2019, *Nat. Commun.* 16, 3118; Anderson et al. 2015, *Surg. Endosc.* 29, 1406-1412; Engel et al. 2015, *Curr. Opin. Urol.* 25, 331-335; Minas et al. 2014, *Obstet. Gynecol.* 16, 19-28; Zafar et al. 2014, *JSLS.* 18, e2014.00158; Silva et al. 2012, *Asian J. Endosc. Surg.* 5, 1050110; Delacroix and Winters, 2010, *Clin. Colon Rectal Surg.* 23,104-112. The collective economic impact of ureteral injuries in just the United States alone exceeds $1 billion, reflecting an average hospital stay of 4 days and costs exceeding $30,000 per injury.

Several approaches have been explored to help reduce the risk of ureteral injuries during surgery. These include urological procedures, such as inserting a stent or an illuminated catheter into a ureter, but these can disrupt the workflow of surgery and introduce unwanted delays, for example by requiring intraoperative consultation with urologists or other specialists. See e.g., Wood et al. 1996, *J. Am. Assoc. Gynecol. Laparosc*, 3, 393-397; Chahin et al. 2002, *JSLS* 6, 49-52. Other approaches include administering or injecting radioactive dyes or fluorophores (or certain conjugates) to visualize the ureters. Such injection procedures, however, can present additional risks and complexities, and some agents can have limited sensitivity, intensity, and duration of action. See, e.g., Ikeda et al., 2017, *Am. J. Physiol. Renal Physiol.* 312, F629-F639; Al-Taher et al., 2016, *J. Laparoendosc. Adv. Surg. Tech. A.* 26, 870-875; Verbeek et al., 2014, *Ann. Surg. Oncol.* 21, S528-5537; Hyun et al. 2012, *Contrast Media Mol. Imaging* 7, 516-524; Choi et al., 2011, *Angew Chem.* Int. Ed. Engl. 50, 6258-6263; Tanaka, et al. 2007, *J. Urol.* 178, 2197-2201; Cadeddu et al., 2001, *J. Endourology* 15, 111-116.

There remains a need in the art to identify compositions with desirable properties that include the visualization of a ureter during surgical procedures. The present invention meets these and other needs in the art by providing peptide compositions, particularly fluorescent peptide conjugates, which allow sensitive and prolonged ureter visualization following administration, and can further support nerve visualization, including concurrent nerve and ureter visualization.

SUMMARY

Disclosed herein are methods for visualizing a ureter, including methods for fluorescent visualization of a ureter during a surgical procedure.

In one aspect, the disclosure is directed to a method for visualizing a ureter in a subject, the method comprising: (a) administering to the subject an effective amount of a fluorescent conjugate, wherein the fluorescent conjugate comprises a peptide and a fluorescent moiety, and (b) detecting fluorescence of the fluorescent moiety in the ureter following administration. In embodiments, the subject is undergoing a surgical procedure.

In another aspect, the disclosure is directed to a method comprising: (a) administering to a subject undergoing a surgical procedure an effective amount of a fluorescent conjugate, wherein the fluorescent conjugate comprises a peptide and a fluorescent moiety; and (b) visualizing a ureter in the subject by detecting fluorescence of the fluorescent moiety in the ureter.

In another aspect, the disclosure is directed to a method of reducing injury to a ureter, the method comprising: (a) identifying a subject at a risk of a ureteral injury prior to a surgical procedure; (b) administering to the subject undergoing the surgical procedure an effective amount of a fluorescent conjugate, wherein the fluorescent conjugate comprises a peptide and a fluorescent moiety; and (c) visualizing the ureter by detecting fluorescence of the fluorescent moiety in the ureter. In embodiments, the ureteral injury arises from ligation, angulation, transection, laceration, crush, ischemia, or resection.

In embodiments of the methods, the peptide can be a nerve targeting peptide. In any of the methods, the peptide can consist of or comprise any of the amino acid sequences disclosed herein, including those set forth in International Patent Application No. PCT/US2018/045054 and International Patent Application No. PCT/US21/61821. In embodiments, the peptide of the fluorescent conjugate comprises an amino acid sequence selected from the group consisting of SEQ ID NOS: 1-14, 16, 18-82, and 84-748.

In embodiments of any of the methods, the fluorescent moiety can be conjugated directly or indirectly via a linker to the N-terminus, C-terminus, or both N-terminus and C-terminus of the peptide. In embodiments of any of the methods, the fluorescent moiety is selected from the group consisting of a fluorescent protein, a fluorescent peptide, a fluorescent dye, or combinations thereof, as disclosed herein.

In embodiments, any of the methods can further comprise detecting fluorescence of the fluorescent moiety within a period of at least 1 hour, at least 2 hours, at least 3 hours, at least 4 hours, at least 5 hours, at least 6 hours, at least 7 hours, or at least 8 hours, following administration. In embodiments, the methods can further comprise detecting fluorescence of the fluorescent moiety for a period of more than 1 hour, more than 2 hours, more than 3 hours, more than 4 hours, more than 5 hours, more than 6 hours, more than 7 hours, or more than 8 hours, following administration.

In embodiments, the fluorescent conjugate in any of the methods is not further administered to the subject following initial administration. In any of the methods, detecting fluorescence of the fluorescent moiety in the ureter can comprise detecting urine flow in the ureter, and more particularly detecting peristaltic flow of urine in the ureter. In any of any of the methods, the fluorescent conjugate may be administered intravenously. In any of any of the methods, the fluorescent conjugate may be administered orally. In any of the methods, the fluorescent conjugate can be administered to a subject prior to a surgical procedure.

In embodiments, the surgical procedure in any of the methods can comprise a gynecological, urological, colorectal, or cardiovascular surgical procedure; can involve the abdomen or pelvis; can be performed on a kidney, bladder, prostate, uterus, male or female reproductive system, rectum, colon, small intestine, or large intestine; can be an open surgical procedure, a laparoscopic surgical procedure, a microscopic procedure, or an endoscopic procedure; or can be a cancer surgical procedure, and more particularly, a prostate cancer surgical procedure or a colorectal cancer procedure.

In embodiments, the fluorescent conjugate in any of the methods comprises a fluorescent moiety selected from the group consisting of: a fluorescent protein, a fluorescent peptide, a fluorescent dye, or combinations thereof, as disclosed herein.

In embodiments, any of the methods comprise administering the fluorescent conjugate in a pharmaceutical composition, which can comprise a pharmaceutically acceptable excipient.

In embodiments, the fluorescent conjugates can allow nerve visualization, as well as concomitant (or concurrent) nerve and ureter visualization in a subject. In embodiments, the fluorescent conjugates can confer nerve visualization and ureter visualization in a subject at different times during a surgical procedure.

BRIEF DESCRIPTION OF THE DRAWING

FIG. 1: Bright field and fluorescence overlay image of a ureter in a living wild type mouse following intravenous administration of about 2000 nanomoles of a fluorescent conjugate (SEQ ID NO:747). Images were obtained 2 hours following administration using a customized fluorescence detection microscope. Left panel: White reflectance image. Right panel: fluorescence overlay.

DETAILED DESCRIPTION

Disclosed herein are methods for visualization of a ureter, and more particularly, methods for fluorescent visualization of a ureter, by administering a fluorescent conjugate (also referred to herein as a "conjugate") comprising a peptide and a fluorescent moiety. It has been discovered that metabolism and elimination of certain fluorescent conjugates, including ones comprising a nerve targeting peptide, support sensitive and prolonged detection of fluorescence during passage in the ureter from the kidneys to the bladder. Advantageously, use of the fluorescent conjugates herein allows ureter detection both early and later after administration. These properties underscore the broad utility of such conjugates, conferring ureter visualization for shorter periods, as well as longer periods, following administration.

Accordingly, in embodiments, the methods comprise visualizing a ureter in a subject by detecting the fluorescent moiety in the ureteral flow of urine, and more particularly in the peristaltic ureteral flow of urine. The fluorescent conjugate can be administered intravenously, and can be administered to a subject prior to a surgical procedure.

In embodiments, the peptide in the fluorescent conjugate comprises a nerve targeting peptide, and more particularly, comprises a nerve targeting peptide disclosed in International Patent Application No. PCT/US2018/045054 or in International Patent Application No. PCT/US21/61821, both of which are incorporated herein in their entirety. Accordingly, in embodiments, fluorescent conjugates disclosed herein can allow concurrent detection of ureters and nerves.

In embodiments, the peptide in the fluorescent conjugate comprises the amino acid sequence QVP-WEEPYYVVKKSSGG (HNP401-N-2 with GG linker; SEQ ID NO:21), as disclosed in International Patent Publication No. WO2019028281A2. In embodiments, the fluorescent conjugate is 5FAM-QVPWEEPYYVVKKSSGG-NH2 (HNP401-N-2 with GG linker; SEQ ID NO:747).

The invention may be more fully appreciated by reference to the following description, including the examples. Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described herein. In addition, the materials, methods, and examples are illustrative only and not intended to be limiting.

For the sake of brevity, all documents, or portions of documents, cited in this application including, without limitation, patents, patent applications, articles, books, manuals, and treatises are hereby expressly incorporated by reference in their entirety for any purpose. Citation of any such publication, however, shall not be construed as an admission that it is prior art to the present invention The use of heading and subheadings in sections of this specification is solely for organizational purposes and convenience of reference and is not to be construed as limiting the subject matter described, which is to be construed by reference to the specification as a whole. For example, those of skill in the art will appreciate the usefulness of combining various aspects from different headings and sections as appropriate according to the spirit and scope of the invention described herein.

As will become apparent to one of ordinary skill in the art after reading this document, the illustrated embodiments and their various alternatives may be implemented without confinement to the illustrated examples

I. Definitions

As used herein, the terms "a" and "an" refer to "one or more" of the enumerated components. The use of the alternative (e.g., "or") should be understood to mean either one, both, or any combination thereof of the alternatives. In addition, it should be understood that the individual compounds, or groups of compounds, derived from the various combinations of the structures and substituents described herein, are disclosed by the present application to the same extent as if each compound or group of compounds were set forth individually. Thus, selection of particular structures or particular substituents is within the scope of the present disclosure.

As used herein, the term "about" or "approximately" means a range of values including the specified value, which a person of ordinary skill in the art would consider reasonably similar to the specified value. In embodiments, "about" means within a standard deviation using measurements generally acceptable in the art. In embodiments, "about" means a range extending to +/−10% of the specified value. In embodiments, "about" means the specified value.

It is understood that, whether the term "about" is used explicitly or not, every quantity given herein is meant to refer to both the actual given value and the approximation of such given value that would reasonably be inferred based on the ordinary skill in the art, including equivalents and approximations due to the experimental and/or measurement conditions for such given value. Accordingly, for any embodiment of the disclosure in which a numerical value is prefaced by "about" or "approximately," the disclosure includes an embodiment in which the exact value is recited. Conversely, for any embodiment of the disclosure in which a numerical value is not prefaced by "about" or "approximately", the disclosure includes an embodiment in which the value is prefaced by "about" or "approximately".

The terms "comprising" and "including" are used herein in their open, non-limiting sense. Other terms and phrases used in this document, and variations thereof, unless otherwise expressly stated, should be construed as open ended, as opposed to limiting. As examples of the foregoing: the term "example" is used to provide exemplary instances of the item in discussion, not an exhaustive or limiting list thereof. Adjectives such as "conventional," "normal," "known" and terms of similar meaning should not be construed as limiting the item described to a given time period or to an item available as of a given time, but instead should be read to encompass conventional, or normal technologies that may be available or known now or at any time in the future. Likewise, where this document refers to technologies that would be apparent or known to one of ordinary skill in the art, such technologies encompass those apparent or known to the skilled artisan now or at any time in the future.

As used herein, the following terms have the meanings ascribed to them unless specified otherwise.

The terms "polypeptide," "peptide," and "protein" are used interchangeably herein to refer to a polymer of amino acid residues. The terms apply to naturally occurring amino acid polymers as well as amino acid polymers in which one or more amino acid residues is a non-naturally occurring amino acid (e.g., an amino acid analog). The terms encompass amino acid chains of any length, including full length proteins (i.e., nerve targeting molecules), wherein the amino acid residues are linked by covalent peptide bonds. As used herein, the term "peptide" refers to a polymer of amino acid residues typically ranging in length from 2 to about 50 residues. In certain embodiments the peptide ranges in length from about 2, 3, 4, 5, 7, 9, 10, or 11 residues to about 50, 45, 40, 45, 30, 25, 20, or 15 residues. In certain embodiments the peptide ranges in length from about 8, 9, 10, 11, or 12 residues to about 15, 20 or 25 residues. Where an amino acid sequence is provided herein, L-, D-, or beta amino acid versions of the sequence are also contemplated as well as retro, inversion, and retro-inversion isoforms. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other modified linkages (e.g., where the peptide bond is replaced by an α-ester, a /3-ester, a thioamide, phosphonamide, carbamate, hydroxylate, and the like (see, e.g., Spatola 1983, *Chem. Biochem. Amino Acids and Proteins* 7: 267-357), where the amide is replaced with a saturated amine (see, e.g., Skiles et al., U.S. Pat. No. 4,496,542, which is incorporated herein by reference, and Kaltenbronn et al., 1990, pp. 969-970 in *Proc.* 11*th American Peptide Symposium*, ESCOM Science Publishers, The Netherlands, and the like)).

Accordingly, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. An amino acid may be an L- or D-amino acid. Amino acid analogs refer to compounds that have the same basic chemical structure as a naturally occurring amino acid, i.e., a carbon that is bound to a hydrogen, a carboxyl group, an amino group, and an R group, e.g., homoserine, norleucine, methionine sulfoxide. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUP AC-IUB Biochemical Nomenclature Commission. Nucleotides, likewise, may be referred to by their commonly accepted single-letter codes.

One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Sequence identity" (or "identity") as used herein, refers to the percentage of amino acid residues in a single given sequence that are identical with the amino acid residues in another reference polypeptide sequence after aligning the sequences and introducing gaps, if necessary, to achieve the maximum percent sequence identity, and not considering any conservative substitutions as part of the sequence identity. "Sequence homology" (or "homology"), as used herein, refers to the percentage of amino acid residues in a single given sequence that are identical or have similar chemical properties to the amino acid residues in another reference polypeptide sequence after aligning the sequences and introducing gaps, if necessary, to achieve the maximum percent sequence homology. Thus, in contrast to sequence identity, sequence homology considers any conservative substitutions (as described herein) as part of the sequence alignment. Sequence identity or sequence homology can be determined using well known methods, including publicly available computer programs such as the NCBI BLAST 2.0 software as defined by Altschul et al. 1997, *Nucl. Acids Res.* 25, 3389-3402. These programs optimally align sequences using default gap weights in order to produce the highest level of sequence identity or sequence homology between the given and reference sequences.

As used herein, the terms "label" refers to a molecule that facilitates the visualization and/or detection of a targeting molecule disclosed herein. In embodiments, the label is a fluorescent moiety.

The terms "individual," "patient," or "subject" are used interchangeably. As used herein, they mean any mammal (i.e. species of any orders, families, and genus within the taxonomic classification animalia: chordata: vertebrata: mammalia). In embodiments, the mammal is a cow, horse, sheep, pig, cat, dog, goat, mouse, rat, rabbit, guinea pig, non-human primate, or human. In embodiments, the mammal is a human subject, and more particularly, a human subject undergoing a surgical procedure. None of the terms require or are limited to situations characterized by the supervision (e.g. constant or intermittent) of a health care worker (e.g. a doctor, a registered nurse, a nurse practitioner, a physician's assistant, an orderly, or a hospice worker).

The terms "administer," "administering", "administration," and the like, as used herein, refer to the methods that may be used to enable delivery of agents or compositions to the desired site of biological action. These methods include, but are not limited to parenteral injection (e.g., intravenous, subcutaneous, intraperitoneal, intramuscular, intravascular, intrathecal, intravitreal, infusion, or local). Administration techniques that are optionally employed with the agents and methods described herein, include e.g., those discussed in in Gennaro: *Remington: The Science and Practice of Pharmacy*, 21$^{st}$ Ed. (Lippincott Williams & Wilkins, 2005) and in *Goodman & Gilman's The Pharmacological Basis of Therapeutics* (McGraw-Hill Professional, 2005). In embodiments, administration is via systemic intravenous injection into human patients.

The term "effective amount" is interchangeable with a "therapeutically effective amount" and means an amount sufficient to accomplish a stated purpose, e.g., to achieve the effect for which it is administered, such as allowing fluorescent visualization of a ureter intraoperatively (during the course of surgery, a surgical procedure, a surgical method, or an operation). An example of an "effective amount" is an amount sufficient to contribute to the treatment, prevention, or reduction of an adverse event caused by a surgical or medical procedure, such as an iatrogenic ureteral injury (IUI) during an abdominal surgical procedure. The desired effect may, but does not necessarily, occur by administration of one dose. It may also occur after administration of a series of doses. Thus, an effective amount may be administered in one or more administrations. Determination of a therapeutically effective amount of a composition is within the capabilities of a skilled artisan, particularly in light of the detailed disclosure herein. For example, a dose for humans can be formulated to achieve a concentration that has been found to be effective in animals. The dosage in humans can be adjusted by monitoring the effectiveness of an agent or composition disclosed herein and adjusting the dosage upwards or downwards. Adjusting the dose to achieve maximal efficacy in humans based on the methods described herein and other methods is well within the capabilities of the ordinarily skilled artisan.

The term "pharmaceutically acceptable" as used herein, refers to a material that does not abrogate the biological activity or properties of the agents and compositions described herein, and is relatively nontoxic (i.e., the toxicity of the material significantly outweighs the benefit of the material). In some instances, a pharmaceutically acceptable material may be administered to an individual without causing significant undesirable biological effects or significantly interacting in a deleterious manner with any of the components of the composition in which it is contained.

The term "surgery" as used herein, refers to any methods or procedures that may be used to manipulate, change, or cause an effect by a physical intervention. Surgical methods and procedures include, but are not limited to, open surgery, microscopic surgery, endoscopic surgery, laparoscopic surgery, minimally invasive surgery, robotic surgery. In some instances, the subject of the surgery is a human subject or human patient. A surgical procedure may include a gynecological, urological, colorectal, or cardiovascular surgical procedure. A surgical procedure may also include, but is not limited to, an abdominal or pelvic procedure. In certain instances, the surgical procedure is performed on a kidney, bladder, prostate, uterus, male or female reproductive system, rectum, colon, small intestine, or large intestine. A surgical procedure may be a cancer surgical procedure, including, for example, a prostate cancer surgical procedure or a colorectal procedure. A surgical procedure may also include a procedure that presents a risk of ureter injury, and that in some cases, may affect nerves as well, as the compositions and methods described herein can support intraoperative nerve visualization, including concurrent nerve and ureter visualization in a subject during surgery.

II. Methods

The present disclosure provides methods of visualizing a ureter, particularly during surgery, with the use of a fluorescent conjugate that comprises a peptide linked to a fluorescent moiety, i.e., a labeled peptide. In embodiments, the peptide comprises a nerve targeting peptide. In embodiments, the fluorescent conjugates (and compositions thereof) described herein are useful as surgical adjuncts in such methods to reduce the likelihood of ureter injuries, and in particular iatrogenic ureteral injuries (IUI), during surgical procedures.

As described further herein, it has been observed that nerve-targeting fluorescent conjugates can be cleared by renal excretion under conditions that allow significant and extended fluorescence during passage through the ureter. Consequently, ureter visualization can be achieved by detecting the fluorescent moiety in the flow of urine through a ureter, and more particularly, the peristaltic flow of urine through a ureter. Ureter visualization can persist for an extended period, lasting several hours or more after administration of certain fluorescent conjugates.

Accordingly, in embodiments, the disclosure provides methods of visualizing a ureter in a subject using any of the molecules and compositions described herein. In embodiments, the subject is undergoing a procedure, such as a diagnostic procedure, a medical procedure, or a surgical procedure.

In one aspect, the methods comprise: (a) administering to a subject an effective amount of a fluorescent conjugate, wherein the fluorescent conjugate comprises a peptide and a fluorescent moiety; and (b) detecting fluorescence of the fluorescent moiety in the ureter of the subject following administration.

In another aspect, the methods comprise: (a) administering to a subject undergoing a surgical procedure an effective amount of a fluorescent conjugate, wherein the fluorescent conjugate comprises a peptide and a fluorescent moiety; and (b) visualizing a ureter in the subject by detecting fluorescence of the fluorescent moiety in the ureter.

In another aspect, the methods comprise: (a) identifying a subject at a risk of a ureteral injury prior to a surgical procedure; (b) administering to the subject undergoing the surgical procedure an effective amount of a fluorescent conjugate, wherein the fluorescent conjugate comprises a peptide and a fluorescent moiety; and (c) visualizing the ureter by detecting fluorescence of the fluorescent moiety in the ureter. As used herein, a subject at risk of ureteral injury includes a subject that is in need of a diagnostic, medical, or surgical procedure described herein.

In embodiments, the fluorescent conjugate is initially administered prior to the surgical procedure. In embodiments, the fluorescent conjugate is not administered following the initial administration. In embodiments, the fluorescent conjugate is administered during the surgical procedure. In embodiments, the fluorescent conjugate is administered prior to and during the surgical procedure.

In embodiments, a surgical procedure comprises a gynecological, urological, colorectal, or cardiovascular surgical procedure. In embodiments, the surgical procedure comprises an abdominal or pelvic procedure. In embodiments, the surgical procedure is performed on a kidney, bladder, prostate, uterus, male or female reproductive system, rectum, colon, small intestine, or large intestine. In embodiments, the surgical procedure is an open surgical procedure, a laparoscopic surgical procedure, a microscopic procedure, or an endoscopic procedure. In embodiments, the surgical procedure is a cancer surgical procedure, and more particularly, a prostate cancer surgical procedure.

In embodiments of any of these methods, the fluorescent conjugate is administered to a subject, as described herein, including humans and mammals (e.g., mice, rats, pigs, cats, dogs, and horses). In embodiments, the subject is are mammal. In embodiments, the subject is a primate. In embodiments, the subject is a human. In embodiments, the human subject is a pediatric subject (21 years and younger), an adult subject (22 years to 65 years), or a geriatric subject (65 years and above).

The fluorescent conjugate can be administered by any route, as described further herein. In embodiments, the fluorescent conjugate is administered intravenously. In embodiments, the fluorescent conjugate is administered orally. In embodiments, a fluorescent conjugate administered by any route may be administered as a pharmaceutical composition, as described herein, which may include a pharmaceutically acceptable excipient.

A fluorescent moiety of a fluorescent conjugate can be detected in a ureter by any suitable method known in the art. For example, a fluorescent moiety may be detected by exciting the fluorophore in the surgical field with the appropriate wavelength of light and detecting the resulting fluorescence (and surgical field) using a combination of filters, lenses and cameras.

In embodiments of the methods, the fluorescent moiety is detected in a ureter by a medical device adapted for fluorescence guided surgery (FGS). Such adapted devices may include, but are not limited to, hand held or mounted devices used in open surgery; minimally invasive devices, such as laparoscopes and endoscopes used in abdominal and pelvic procedures; robotic surgical systems used in prostate surgeries; and other devices, such as surgical loupes. Devices may provide real time synchronous information from bright field illumination and fluorescence emission. One or more light sources can be used to excite and illuminate the sample or surgical field. Light can be collected to produce final images, using optical filters customized to the emission spectrum of the fluorescent moiety, imaging lenses, and digital cameras (such as CCD and CMOS detector systems). Live video processing can also be performed to enhance contrast during fluorescence detection and improve the sensitivity of the fluorescent signal.

In embodiments of the methods, fluorescence of the fluorescent moiety is detected in a ureter within a period of at least 1 hour, at least 2 hours, at least 3 hours, at least 4 hours, at least 5 hours, at least 6 hours, at least 7 hours, or at least 8 hours, following administration.

In embodiments of the methods, fluorescence of the fluorescent moiety is detected in a ureter for a period of more than 1 hour, more than 2 hours, more than 3 hours, more than 4 hours, more than 5 hours, more than 6 hours, more than 7 hours, or more than 8 hours, following administration.

In embodiments of the methods, fluorescence of the fluorescent moiety is detected in a ureter after 30 minutes, after 1 hour, after 2 hours, after 3 hours, after 4 hours, after 5 hours, after 6 hours, after 7 hours, or after more than 8 hours, following administration.

In embodiments of the methods, the fluorescent conjugates can allow concomitant nerve detection, as well as ureter visualization, including intraoperative nerve and ureter visualization. Such a nerve can include a human nerve, as disclosed, for example, in the '054 Application, such as motor nerves, sensory nerves, sympathetic and parasympathetic nerves, peripheral nerves, and autonomic nerves.

More generally, the methods, conjugates, and compositions described herein can also encompass open surgical procedures, laparoscopic surgical procedures, microscopic procedures, and endoscopic procedure.

In addition, the methods, conjugates, and compositions described herein can also be used in surgical procedures, in which visualization of nerves, as well as ureters, is desirable.

III. Fluorescent Conjugates

Fluorescent conjugates for use in the present methods comprise peptides, and more particularly, nerve-targeting peptides, linked to fluorescent moieties (or a peptide otherwise comprising a fluorescent label).

Peptides

In embodiments, the nerve targeting peptide is any peptide, including any deletion or linker variant, as disclosed in International Patent Application No. PCT/US2018/045054 ("the '054 Application," published as WO2019028281A2), which is incorporated herein in its entirety). Accordingly, such peptides comprise, or consist of, any one of the following amino acid sequences (peptide sequences) listed in Table 1 (SEQ ID NOS:1-17, 20-28, and 96-102):

TABLE 1

| Name | SEQ ID NO: | Amino Acid Sequence |
|---|---|---|
| HNP401 | 1 | SGQVPWEEPYYVVKKSS (SEQ ID NO: 1) |
| HNP402 | 2 | WEYHYVDLNWTSQHPQ (SEQ ID NO: 2) |
| HNP403 | 3 | DLPDIIWDENWETA (SEQ ID NO: 3) |
| HNP401 with GGC linker | 4 | Ac-SGQVPWEEPYYVVKKSSGGC (SEQ ID NO: 4) |
| HNP402 with GGC linker | 5 | Ac-WEYHYVDLNWTSQHPQGGC (SEQ ID NO: 5) |
| HNP403 with GGC linker | 6 | Ac-DLPDIIWDFNWETAGGC (SEQ ID NO: 6) |
| HNP401-N-2 with GGC linker | 7 | Ac-QVPWEEPYYVVKKSSGGC (SEQ ID NO: 7) |
| HNP401-N-4 with GGC linker | 8 | Ac-PWEEPYYVVKKSSGGC (SEQ ID NO: 8) |
| HNP401-N-6 with GGC linker | 9 | Ac-EEPYYVVKKSSGGC (SEQ ID NO: 9) |
| HNP401-N-8 with GGC linker | 10 | Ac-PYYVVKKSSGGC (SEQ ID NO: 10) |
| HNP401-C-2 with GGC linker | 11 | Ac-SGQVPWEEPYYVVKKGGC (SEQ ID NO: 11) |
| HNP401-C-4 with GGC linker | 12 | Ac-SGQVPWEEPYYVGGC (SEQ ID NO: 12) |
| HNP401-C-6 with GGC linker | 13 | Ac-SGQVPWEEPYYGGC (SEQ ID NO: 13) |
| HNP401-C-8 with GGC linker | 14 | Ac-SGQVPWEEPGGC (SEQ ID NO: 14) |
| HNP404 | 16 | DTHAHAKPRVPAFKSV (SEQ ID NO: 16) |
| NP41 | 17 | Ac-SHSNTQTLAKAPEHTGC (SEQ ID NO: 17) |
| HNP401-N-2 | 20 | QVPWEEPYYVVKKSS (SEQ ID NO: 20) |

TABLE 1-continued

| Name | SEQ ID NO: | Amino Acid Sequence |
|---|---|---|
| HNP401-N-2 (with GG linker) | 21 | QVPWEEPYYVVKKSSGG (SEQ ID NO: 21) |
| HNP401-N-4 | 22 | PWEEPYYVVKKSS (SEQ ID NO: 22) |
| HNP401-N-6 | 23 | EEPYYVVKKSS (SEQ ID NO: 23) |
| HNP401-N-8 | 24 | PYYVVKKSS (SEQ ID NO: 24) |
| HNP401-C-2 | 25 | SGQVPWEEPYYVVKK (SEQ ID NO: 25) |
| HNP401-C-4 | 26 | SGQVPWEEPYYVV (SEQ ID NO: 26) |
| HNP401-C-6 | 27 | SGQVPWEEPYY (SEQ ID NO: 27) |
| HNP401-C-8 | 28 | SGQVPWEEP (SEQ ID NO: 28) |
| HNP401-N-4 (with GG linker) | 102 | PWEEPYYVVKKSSGG (SEQ ID NO: 102) |
| HNP401-N-6 (with GG linker) | 101 | EEPYYVVKKSSGG (SEQ ID NO: 101) |
| HNP401-N-8 (with GG linker) | 100 | PYYVVKKSSGG (SEQ ID NO: 100) |
| HNP401-C-2 (with GG linker) | 99 | SGQVPWEEPYYVVKKGG (SEQ ID NO: 99) |
| HNP401-C-4 (with GG linker) | 98 | SGQVPWEEPYYVGG (SEQ ID NO: 98) |
| HNP401-C-6 (with GG linker) | 97 | SGQVPWEEPYYGG (SEQ ID NO: 97) |
| HNP401-C-8 (with GG linker) | 96 | SGQVPWEEPGG (SEQ ID NO: 96) |

In embodiments, a peptide comprises, or consists of, any of SEQ ID NOS:1-14, 16, 20-28, and 96-102.

In addition, a peptide can comprise, or consist of, any variant of the amino acid sequences described in the '054 Application. Such variants can include, without limitation, peptides comprising or consisting of amino acid sequences that share 75%-99% identity or 75%-99% homology with an amino acid sequence in Table 1 (or as otherwise disclosed in the '054 Application).

In embodiments, a peptide comprises, or consists of, an amino acid sequence having at least 75% identity to any one of SEQ ID NOS:1-14, 16, 20-28, and 96-102. In embodiments, the peptide comprises, or consists of, an amino acid sequence having at least 80% identity to any one of SEQ ID NOS:1-14, 16, 20-28, and 96-102. In embodiments, the peptide comprises, or consists of, an amino acid sequence having at least 85% identity to any one of SEQ ID NOS:1-14, 16, 20-28, and 96-102. In embodiments, the peptide comprises, or consists of, an amino acid sequence having at least 90% identity to any one of SEQ ID NOS:1-14, 16, 20-28, and 96-102. In embodiments, the peptide comprises, or consists of, an amino acid sequence having at least 95% identity to any one of SEQ ID NOS:1-14, 16, 20-28, and 96-102. In embodiments, the peptide comprises, or consists of, an amino acid sequence having at least 97% identity to any one of SEQ ID NOS:1-14, 16, 20-28, and 96-102.

In embodiments, a peptide consists of or comprises a peptide sequence sharing at least 80% homology with any one of SEQ ID NOS:1-14, 16, 20-28, and 96-102. In embodiments, a peptide consists of or comprises a peptide sequence sharing at least 80% homology with any one of SEQ ID NOS:1-14, 16, 20-28, and 96-102. In embodiments, a peptide comprises, or consists of, an amino acid sequence sharing at least 85% homology with any one of SEQ ID NOS:1-14, 16, 20-28, and 96-102. In embodiments, a peptide comprises, or consists of, an amino acid sequence sharing at least 90% homology any one of SEQ ID NOS: 1-14, 16, 20-28, and 96-102. In embodiments, a peptide comprises, or consists of, an amino acid sequence sharing at least 95% homology with any one of SEQ ID NOS:1-14, 16, 20-28, and 96-102. In embodiments, a peptide comprises, or consists of, an amino acid sequence sharing at least 99% homology any one of SEQ ID NOS:1-14, 16, 20-28, and 96-102.

In embodiments, a peptide comprises, or consists of, an amino acid sequence of about 13 to about 25 amino acids comprising a core binding domain, PYYVVKK (SEQ ID NO:40), and an N-terminal sequence of QVPWEE (SEQ ID NO:41).

In embodiments, a peptide comprises an amino acid core binding domain of PYY or PYYVV (SEQ ID NO:83) and an N-terminal sequence of QVPWEE (SEQ ID NO:41). In embodiments, a peptide comprises an amino acid core binding domain of PYY and an N-terminal sequence of QVPWEE (SEQ ID NO:41). In embodiments, a peptide comprises an amino acid core binding domain of PYYVV (SEQ ID NO:83) and an N-terminal sequence of QVPWEE (SEQ ID NO:41).

In embodiments, a peptide comprises, or consists of, QVPWEEPYYVVKKSSGG (HNP401-N-2 with GG linker; SEQ ID NO:21)

In embodiments, a peptide comprises, or consists of, an amino acid sequence selected from the group consisting of:

```
                            (HNP401; SEQ ID NO: 1)
SGQVPWEEPYYVVKKSS, (HNP402; SEQ ID NO: 2)
WEYHYVDLNWTSQHPQ,
and (HNP403; SEQ ID NO: 3)
DLPDIIWDFNWETA.
```

In embodiments, a peptide comprises, or consists of, an amino acid sequence selected from the group consisting of:

```
                            (HNP401; SEQ ID NO: 1)
SGQVPWEEPYYVVKKSS, (HNP401-N-2 with GGC linker; SEQ ID NO: 7)
Ac-QVPWEEPYYVVKKSSGGC, (HNP401-C-2 with GGC linker; SEQ ID NO: 11)
Ac-SGQVPWEEPYYVVKKGGC,
```

```
                            (HNP401-N-2; SEQ ID NO: 20)
QVPWEEPYYVVKKSS, (HNP401-N-2 with GG linker; SEQ ID NO: 21)
QVPWEEPYYVVKKSSGG,
and (HNP401-C-2; SEQ ID NO: 25)
SGQVPWEEPYYVVKK,
and (HNP401-C-2 with GG linker; SEQ ID NO: 99)
SGQVPWEEPYYVVKKGG.
```

In embodiments, a peptide comprises, or consists of, the amino sequence of any one of SEQ ID NOS:1, 4, 7-14, 20-28, and 96-102.

In embodiments, a peptide comprises, or consists of, the amino sequence of any one of SEQ ID NOS:1, 20, and 22-24.

In embodiments, a peptide comprises, or consists of, the amino sequence of any one of SEQ ID NOS:1 and 25-28.

In embodiments, a peptide comprises, or consists of, the amino sequence of any one of SEQ ID NOS:4 and 7-10.

In embodiments, a peptide comprises, or consists of, the amino sequence of any one of SEQ ID NOS:4 and 11-14.

In embodiments, a peptide comprises, or consists of, the amino sequence of any one of SEQ ID NOS:21 and 100-102.

In embodiments, a peptide comprises, or consists of, the amino sequence of any one of SEQ ID NOS:96-99.

In embodiments, a peptide is a nerve targeting peptide disclosed in PCT Application No. PCT/US21/61821 ("the '821 Application"), which is incorporated herein in its entirety. In some embodiments, these peptides were derived from phage display library screens based on selective binding to one of four different nerve target proteins: Human Myelin Protein Zero (MPZ), Myelin Basic Protein, Myelin Proteolipid Protein (Myelin PLP), and Nidogen-2. Such peptides comprise, or consist of, any of the amino acid sequences (SEQ ID NOS:18, 19, 29-82, 84-95, and 103-471) listed in Table 2. In some embodiments, these peptides were derived from phage display screens based on selective binding to laminin trimers 421, 521, or both. Such peptides comprise, or consist of, any of the amino acid sequences listed in Table 3 (SEQ ID NOS:472-678). In some embodiments, these peptides were derived from phage display screens based on selective binding to neuron and nerve extracts but not muscle extracts. Such peptides comprise, or consist of, any of the amino acid sequences listed in Table 4 (SEQ ID NOS:679-746).

TABLE 2

| Nerve Target Protein | Amino Acid Sequence | SEQ ID NO: |
|---|---|---|
| R3 Human MPZ | ALPLSAS | 95 |
|  | TSPWELR | 94 |
|  | SHLASRP | 93 |
|  | DPITRLK | 92 |
|  | VLKNNPT | 91 |
|  | IKPPYTH | 90 |
|  | ETTRNYG | 89 |
|  | SHSPGNK | 88 |
|  | WPSISRP | 87 |
|  | LSSPLSL | 86 |
|  | VLTKPMP | 85 |
|  | TMASPAK | 84 |
|  | KMAGHTV | 82 |
|  | SAHAKHH | 81 |
|  | DRNSVFW | 80 |
|  | GPLRMAT | 79 |

TABLE 2-continued

| Nerve Target Protein | Amino Acid Sequence | SEQ ID NO: |
|---|---|---|
| | TESLFPH | 78 |
| | RVPHSRT | 77 |
| | GLTPKLF | 76 |
| | GDERIVRTLSHN | 75 |
| | CLKQQTGDC | 103 |
| | EGHVWSEYTWGT | 104 |
| | FMSDVDH | 105 |
| | ISSVTVV | 106 |
| | KQPAMFN | 107 |
| | LISPTAR | 108 |
| | LVLQTTP | 109 |
| | NPTSEGA | 110 |
| | THSTDLS | 111 |
| | TTNVTEIERESY | 112 |
| | YAPWRVF | 113 |
| | YGQSITE | 114 |
| | CDIKDANSC | 115 |
| | CIKGEDNQC | 116 |
| | HNQLLYT | 117 |
| | IEQVGWR | 118 |
| | KTPILAS | 119 |
| | LWAKRDA | 120 |
| | NPISPRN | 121 |
| | NTASMTT | 122 |
| | SAHSVVE | 123 |
| | YSSLTSN | 124 |
| | AWTMRAS | 125 |
| | CERIGPREC | 126 |
| | CQKWFTFAC | 127 |
| | CSNALNKAC | 128 |
| | FSPRDVS | 129 |
| | FSTTGRG | 130 |
| | HHPLFID | 131 |
| | LVNPFPE | 132 |
| | YEGERGA | 133 |
| | CEDRQRSMC | 134 |
| | CGEKIMSLC | 135 |
| | DRYLLNQ | 136 |
| | FPSYTIS | 137 |
| | GGSKVWG | 138 |
| | GLWRHTM | 139 |
| | KRNLWDI | 140 |
| | SPNTNSH | 141 |
| | TLLHYSA | 142 |
| | VPLAYLR | 143 |
| | VVPLKWI | 144 |
| | CRVGVTSAC | 145 |
| | FALPAGL | 146 |
| | FRVTQTA | 147 |
| | HPLMVPS | 148 |
| | LPNANNL | 149 |
| | MIHTRQT | 150 |
| | SETESYM | 151 |
| | SNALSYF | 152 |
| | SYLPPFI | 153 |
| | VHTPYRS | 154 |
| | WPRPIQI | 155 |
| | WTSVATA | 156 |
| | ALPISYL | 157 |
| | FEHMAVT | 158 |
| | NASVPPK | 159 |
| | SGHGAFR | 160 |
| | TTLVVTA | 161 |
| | CPDAARNSC | 162 |
| | CYSSVADMC | 163 |
| | LSPPRIM | 164 |
| | WMTNLDP | 165 |
| | KLPTLSV | 166 |
| | AMSNLSY | 167 |
| | HPFPRFD | 168 |
| | LPAESHW | 169 |
| | STHEWRT | 170 |
| | TTWPNTA | 171 |
| | YMKHSPG | 172 |
| | AYLEDWRSMSTR | 173 |
| | GPVVSGM | 174 |
| | HLDSRRH | 175 |
| | LVLSNPR | 176 |
| | NMSHSNR | 177 |
| | SVAYVPV | 178 |
| | YPQARTS | 179 |
| | MYHDSVS | 180 |
| | ADNVLRRALENI | 181 |
| | QIAHLEY | 182 |
| | GMVSPHHSVYRH | 183 |
| | GSWSSGF | 184 |
| | NGAYSLAIRYTS | 185 |
| | YTPNWHFRWMPA | 186 |
| | GEWRARIDQDVS | 187 |
| R3 Myelin Basic Protein | NDTKTPS | 74 |
| | HPSTWHK | 73 |
| | EHGYYKV | 72 |
| | LPMRILT | 71 |
| | SVLRMLN | 70 |
| | AITSRNA | 69 |
| | SKSDAWR | 68 |
| | ILLPSLN | 67 |
| | WTMKPNY | 66 |
| | AGQLMRCANC | 65 |
| | AWSTSSV | 64 |
| | LRPISHE | 63 |
| | MQTQGRV | 62 |
| | SPDRTSL | 61 |
| | DPWVMLR | 60 |
| | QIGVLPS | 59 |
| | QNTGLKW | 58 |
| | AGFPPNT | 57 |
| | DGKNTSN | 56 |
| | HRLPWHH | 55 |
| | AGSLLSL | 188 |
| | AIPPRKL | 189 |
| | AISWKGF | 190 |
| | AKFTMWV | 191 |
| | ALRDTRV | 192 |
| | ALYNQMT | 193 |
| | AQFLTIY | 194 |
| | AQLGAFR | 195 |
| | ARVPNPL | 196 |
| | CTMTNQYDC | 197 |
| | DSQEKSV | 198 |
| | DVRIWTL | 199 |
| | ELKSLRF | 200 |
| | ESKSPRE | 201 |
| | ETHYKIA | 202 |
| | FDLLARK | 203 |
| | FQLSYET | 204 |
| | GEPALVT | 205 |
| | GPRVTPH | 206 |
| | GQWWKML | 207 |
| | GRHTDVV | 208 |
| | GSPYGWG | 209 |
| | GVAEVGL | 210 |
| | HAHWARL | 211 |
| | HFTFFPI | 212 |
| | HPWSHPN | 213 |
| | HQMRTML | 214 |
| | HQPLFPR | 215 |
| | HRTHLHQ | 216 |
| | HSGPLLP | 217 |
| | HSSATMS | 218 |
| | IGTRWHQ | 219 |
| | INFPFAV | 220 |
| | IPIPYRT | 221 |
| | IPYSQMP | 222 |
| | KIITTKS | 223 |
| | KMSLAPP | 224 |
| | KVHHLAR | 225 |
| | LELHQNV | 226 |
| | LITHPQL | 227 |
| | LMLPQLE | 228 |
| | LVPPVNH | 229 |
| | MNSPLAQ | 230 |
| | MQRLGAD | 231 |
| | NGPNSLQ | 232 |
| | NGVSSSL | 233 |

TABLE 2-continued

| Nerve Target Protein | Amino Acid Sequence | SEQ ID NO: |
|---|---|---|
| | NLTYLRF | 234 |
| | QGAYVRP | 235 |
| | QKALPQT | 236 |
| | QTSIMSG | 237 |
| | QYWDILG | 238 |
| | RGHPSQL | 239 |
| | RSRKHRP | 240 |
| | RTTDWWT | 241 |
| | RVIPSTT | 242 |
| | SAVLMPP | 243 |
| | SEGLTLL | 244 |
| | SGPFPLV | 245 |
| | SIQTSAM | 246 |
| | SKLAGFP | 247 |
| | SKPHASH | 248 |
| | SLDHLRL | 249 |
| | SLKTTNP | 250 |
| | SLWQTLR | 251 |
| | SLWTHRT | 252 |
| | SNAHTLP | 253 |
| | SPKPDIP | 254 |
| | SRHLPPL | 255 |
| | SSFYVAY | 256 |
| | SSMRYNS | 257 |
| | SVGLPTK | 258 |
| | SYRSMAP | 259 |
| | SYVTVFR | 260 |
| | TGPSSAV | 261 |
| | TGSVSKQ | 262 |
| | THKHMMT | 263 |
| | TIRVAHT | 264 |
| | TPGRATL | 265 |
| | TPVLWLP | 266 |
| | TPVRLNT | 267 |
| | TRIPILL | 268 |
| | TTTQGHP | 269 |
| | VGTFWTR | 270 |
| | VIRTAAM | 271 |
| | VLSPYHN | 272 |
| | VRGTPNH | 273 |
| | WDLPQNR | 274 |
| | WDLRHSK | 275 |
| | WTYHPTT | 276 |
| | WVPDRSL | 277 |
| | YPTYLSY | 278 |
| | YPYVPIY | 279 |
| | YSSRLND | 280 |
| | YTASPRW | 281 |
| | YVNRVKQ | 282 |
| | AAGQRSF | 283 |
| | AILTRPP | 284 |
| | ALGTRPL | 285 |
| | ASNTSKG | 286 |
| | AVRQTTM | 287 |
| | CEDSDKSVC | 288 |
| | CNRVPFKQC | 289 |
| | CPRMNNPLC | 290 |
| | DVVKDVI | 291 |
| | ESPYPHS | 292 |
| | FKLPWAS | 293 |
| | FLNQAPT | 294 |
| | FSAGVGK | 295 |
| | GHSYILGKPTA | 296 |
| | GPITHAI | 297 |
| | HFLRPSD | 298 |
| | HLLKTHS | 299 |
| | HMAGVNQ | 300 |
| | HPDTLPQ | 301 |
| | HPTGTPT | 302 |
| | HTGLRSL | 303 |
| | KGQPLFR | 304 |
| | KYRHGAE | 305 |
| | LFRRVTE | 306 |
| | LTKSLNH | 307 |
| | MPLLELP | 308 |
| | MTNHGNA | 309 |
| | NLKLWTR | 310 |
| | NLLQGVM | 311 |
| | NMYPRVT | 312 |
| | NSSPHQI | 313 |
| | QGTLFDT | 314 |
| | QPIDSTS | 315 |
| | SEPGTVR | 316 |
| | SGNLKKA | 317 |
| | SIAEVLGLWRNV | 318 |
| | SIRMTEI | 319 |
| | SISKIRT | 320 |
| | SLRSVGA | 321 |
| | SSGMLSK | 322 |
| | SYTLSRS | 323 |
| | TLLTALT | 324 |
| | TPLYLSS | 325 |
| | VSFTLEP | 326 |
| | VVDMSTY | 327 |
| | WPDLRIL | 328 |
| | WSLPLLS | 329 |
| | WSPRWPS | 330 |
| | YLPPPLP | 331 |
| | DSYLLSA | 332 |
| | FVLPNKN | 333 |
| | IILPSAQ | 334 |
| | KNSIAPR | 335 |
| | LPPQISR | 336 |
| | MPSLKHQ | 337 |
| | NPTDTNK | 338 |
| | NTSLSFK | 339 |
| | QNSYLSN | 340 |
| | QQAHLQS | 341 |
| | SPPRFIP | 342 |
| | SWFESHN | 343 |
| | TPQVMLK | 344 |
| | TSPPLAH | 345 |
| | TSRLVST | 346 |
| | VAHQRVS | 347 |
| | VPTLRIP | 348 |
| | YATATPS | 349 |
| | ANLSRSV | 350 |
| | FSARTNT | 351 |
| | HFYGPGP | 352 |
| | HPWLGNR | 353 |
| | HYSPNVM | 354 |
| | NFAQHMQ | 355 |
| | SNAERWR | 356 |
| | SRPTRVP | 357 |
| | SVEYGQL | 358 |
| | TGNLRLY | 359 |
| | MDLSLKP | 360 |
| | NTPKVLA | 361 |
| | TQMTMDS | 362 |
| R3 Myelin PLP | ATLKPYR | 54 |
| | GLIRHYT | 53 |
| | MTPHTSC | 52 |
| | TNPWKPH | 51 |
| | HQGSRTY | 50 |
| | RFELPAP | 49 |
| | YTPMGTG | 48 |
| | GPFLFTV | 47 |
| | LALYARM | 46 |
| | LRFQIPP | 45 |
| | FPVVTRN | 44 |
| | RHNVEFS | 43 |
| | LTHHFAP | 42 |
| | NPSHHPR | 39 |
| | YPKLWTY | 38 |
| | FKMPIPT | 37 |
| | NPNWRTI | 36 |
| | SMWSQFR | 35 |
| | DTSRTME | 34 |
| | EKPSWTR | 33 |
| | ASLTLAL | 363 |
| | DRHEGHR | 364 |
| | FRIDKSM | 365 |
| | GHLQSLF | 366 |
| | GLWGPSL | 367 |
| | KPSASIY | 368 |

TABLE 2-continued

| Nerve Target Protein | Amino Acid Sequence | SEQ ID NO: |
|---|---|---|
| | LPSHASI | 369 |
| | LPVKNLL | 370 |
| | MKIMPMD | 371 |
| | SAQSRSF | 372 |
| | SLPSLLP | 373 |
| | SVVYQNS | 374 |
| | TTTIADM | 375 |
| | VTGPGTP | 376 |
| | VTPNKAR | 377 |
| | WHYTPSM | 378 |
| | WSRISVD | 379 |
| | ALFQERK | 380 |
| | AQASSAR | 381 |
| | EVLYPNN | 382 |
| | HLHTRPT | 383 |
| | IRPTHNG | 384 |
| | KGVIPAT | 385 |
| | LHQTYRP | 386 |
| | LPHRLNP | 387 |
| | TGISSTP | 388 |
| | TMPIKAM | 389 |
| | VPGHISG | 390 |
| | VSASWMP | 391 |
| | WSPHGYK | 392 |
| | YSQAISA | 393 |
| | AVVAMNK | 394 |
| | GIPSSKN | 395 |
| | NDASTVS | 396 |
| | QLPRNNL | 397 |
| | SLNRGGA | 398 |
| | SLPGYRH | 399 |
| | SVLPDKL | 400 |
| | TLWAQKT | 401 |
| | TQPRYPS | 402 |
| | VFPERRV | 403 |
| | VGYRSAS | 404 |
| | VRTSMNH | 405 |
| | YTWTPSR | 406 |
| | FSLDRDG | 407 |
| | FSTPTNV | 408 |
| | GPAAVII | 409 |
| | GWSTAIR | 410 |
| | HKAPLGT | 411 |
| | IDRVRGL | 412 |
| | LMQKPSI | 413 |
| | SVMWMTP | 414 |
| | TKITPHR | 415 |
| | YSSRLTA | 416 |
| | ARFVPLT | 417 |
| | DGSRDLV | 418 |
| | EKSTTVA | 419 |
| | YSDTYKH | 420 |
| | EPSSFTF | 421 |
| | GKSYSQI | 422 |
| | GNVFQTS | 423 |
| | IIPPTSV | 424 |
| | LPLRLHA | 425 |
| | NVFSATP | 426 |
| | QRRSVIL | 427 |
| | SGVATYT | 428 |
| | SWDVLEL | 429 |
| | TFPERLR | 430 |
| | WSPHRSF | 431 |
| | IHHLESS | 432 |
| | LNGISAL | 433 |
| | SALISTR | 434 |
| | SGLHYAL | 435 |
| | TRASYPQ | 436 |
| | NIPSSIL | 437 |
| | QPNMLKP | 438 |
| | RLQPEPT | 439 |
| | SVEKYSK | 440 |
| | VSSQEQA | 441 |
| | WNTADRL | 442 |
| | MPHAPVQ | 443 |
| | TDVEMVP | 444 |
| | AHQSSVT | 445 |
| | GSAWKKH | 446 |

TABLE 2-continued

| Nerve Target Protein | Amino Acid Sequence | SEQ ID NO: |
|---|---|---|
| R3 Nidogen-2 | ACGEGEADVC | 32 |
| | ACPENKSKHC | 31 |
| | ACEPRSLANC | 30 |
| | ACTVHKWDNC | 29 |
| | GYWRNAL | 19 |
| | KAIHPMRG | 18 |
| | CIHHKGVLC | 447 |
| | CKDGHIRHC | 448 |
| | CNLATSLQC | 449 |
| | CRSPHEPMC | 450 |
| | CVDKMASVC | 451 |
| | CYSAPTKSC | 452 |
| | EAMMHRN | 453 |
| | LHITPEV | 454 |
| | LSIRGLT | 455 |
| | NILSQVN | 456 |
| | QLLESRT | 457 |
| | QMDAKHM | 458 |
| | QTLRPKQ | 459 |
| | TIASLLV | 460 |
| | WLAAGSQ | 461 |
| | ALYLPGR | 462 |
| | ARMAFSL | 463 |
| | ATYNMSQ | 464 |
| | GLRTMEP | 465 |
| | TPWLPTI | 466 |
| | YNHTMMY | 467 |
| | CSFKMNQKC | 468 |
| | LVHPFHG | 469 |
| | CSSSAPRIC | 470 |
| | HSRLPTP | 471 |

TABLE 3

| Target Protein | Amino Acid Sequence | SEQ ID NO: |
|---|---|---|
| Laminin 421/521 | CKSPIKGTC | 472 |
| | CLQKNHKFC | 473 |
| | CVLKCEDQKYRG | 474 |
| | DGANMFNIAPAN | 475 |
| | DRMYSTVPAEGL | 476 |
| | EAVSTQI | 477 |
| | GINLRALDLHAN | 478 |
| | HQSVTGVRSHFH | 479 |
| | SVVGWAAPRTAQ | 480 |
| | TILKPAAQGFAD | 481 |
| | TSAVSLR | 482 |
| | TTLWLDRDEALK | 483 |
| | VIADQSKSAVAV | 484 |
| | AQNLRVHAWASL | 485 |
| | CPMHQSKTC | 486 |
| | CTDGRNFVC | 487 |
| | CTGETLLTC | 488 |
| | CTSSSHQTC | 489 |
| | ETGGLAYGSGQK | 490 |

TABLE 3-continued

| Target Protein | Amino Acid Sequence | SEQ ID NO: |
|---|---|---|
| | GIVPSRHTTGLG | 491 |
| | GWTSDLSRNVRG | 492 |
| | HTQIHRL | 493 |
| | KFADTKLTSLRY | 494 |
| | QLQHVHL | 495 |
| | QPTPSQIKFTRT | 496 |
| | RALDRYLPWSPH | 497 |
| | SLPYAASLNSVE | 498 |
| | STNVQRA | 499 |
| | SVLSTGTANQRH | 500 |
| | SVQTPMWRSLVG | 501 |
| | SWHFTGTPFMNR | 502 |
| | SYTATWSEMSRS | 503 |
| | TALSHRHEAMRW | 504 |
| | TKGIAPK | 505 |
| | TVARSTAQERSI | 506 |
| | AVRPLGLPDNHR | 507 |
| | CIGGPHRNC | 508 |
| | CKSPAIKGC | 509 |
| | CNSWKAAKC | 510 |
| | DSLYRGMHQPRI | 511 |
| | EDRMMTYRYTST | 512 |
| | EVERILTPHVNN | 513 |
| | FNSDSRSTHQED | 514 |
| | HPAWADFFTMSS | 515 |
| | IDLSLRS | 516 |
| | IDQSGLQKSGMK | 517 |
| | LGSSRSPSSFLG | 518 |
| | NGHEVQSRAANR | 519 |
| | QGWKDRLPIWRY | 520 |
| | SHDVANGTSVRT | 521 |
| | SPDRTNWGWQTN | 522 |
| | SVESNSKLTMPR | 523 |
| | WPMMQTR | 524 |
| | CKSERGPEC | 525 |
| | CQGWPRPMC | 526 |
| | CSRAGLSAC | 527 |
| | CTWKHRDNC | 528 |
| | GLLDWGSLQGGN | 529 |

TABLE 3-continued

| Target Protein | Amino Acid Sequence | SEQ ID NO: |
|---|---|---|
| | GPLLFRG | 530 |
| | GSPEKRT | 531 |
| | KASIAYD | 532 |
| | LGYGQGTPHRSN | 533 |
| | QGWEFQVPARHS | 534 |
| | QTFGYSMFNVRT | 535 |
| | RNLHYPLNHPFM | 536 |
| | TAPRWTQ | 537 |
| | VPSYILR | 538 |
| | WRSPLTT | 539 |
| | CQTSGHHQC | 540 |
| | CSSQAKRSC | 541 |
| | CTAWTRQEC | 542 |
| | EYVKFSHSPRTY | 543 |
| | GGWQSLWDKPEH | 544 |
| | GPMLKNLSDAVT | 545 |
| | NHDQGSLTRWRS | 546 |
| | SLLSVVNTSSKS | 547 |
| | VVPSWPSVHRPP | 548 |
| | WGWNGANMSPRG | 549 |
| | CHNADNNGC | 550 |
| | LPMLRHS | 551 |
| | NDTGRHASGISK | 552 |
| | QALRTNYSPLNS | 553 |
| | TLKAGTRANDGV | 554 |
| | CGETTAGKC | 555 |
| | HSTYAPG | 556 |
| | QINWKQADKNAD | 557 |
| | ALPWQSGVHGTK | 558 |
| | TFGSGRSMPIQY | 559 |
| | VYRNGGGLPLTA | 560 |
| | ALKIGPETTIYM | 561 |
| | DWTQVRVTNWFL | 562 |
| | LGHQNGGRADMW | 563 |
| | MTNSGAK | 564 |
| | WAYTDYM | 565 |
| | AHAAGRDMRQGT | 566 |
| | DVIHSSRGAYFE | 567 |
| | NWTHLGVARLQP | 568 |

TABLE 3-continued

| Target Protein | Amino Acid Sequence | SEQ ID NO: |
|---|---|---|
| | SYDGTMLKQVRL | 569 |
| | WQWRSTELGYRY | 570 |
| | WSPANGWRHQTI | 571 |
| | CLHNGQRSC | 572 |
| | CTPRSATLC | 573 |
| | DIMKSPRSNLRS | 574 |
| | QTFHEYLNPARG | 575 |
| | SLNTTWVSPMMK | 576 |
| | AQRMNQA | 577 |
| | GDAQILM | 578 |
| | GHRTLVTSERYL | 579 |
| | LGPSTQGAGQTR | 580 |
| | TFAAAQAELIMV | 581 |
| | WEEHRVEILPDV | 582 |
| | AGAYTSRHAFDE | 583 |
| | CGLATNKSC | 584 |
| | GDVITAYINPWP | 585 |
| | GYDLSRLWGMAS | 586 |
| | ANRYLAS | 587 |
| | CKWTQLWGC | 588 |
| | CLKDTHLNC | 589 |
| | GQPRNIHLPGTH | 590 |
| | GSTTHPHFGLPG | 591 |
| | GWIQDTFVLGRS | 592 |
| | QGHPFIY | 593 |
| | SNPKHVSSLGQM | 594 |
| | WGANTTGRTHGG | 595 |
| | AQGVWWSEWFAP | 596 |
| | CFQPKMNSC | 597 |
| | CWSGNSRSC | 598 |
| | FPLKIRT | 599 |
| | LARSSIMAANNV | 600 |
| | AKTQAPSNWSGV | 601 |
| | CSVWNSGNC | 602 |
| | CTGRISKHC | 603 |
| | GAMMNSNNLVAR | 604 |
| | GGGYHIFGPLVT | 605 |
| | HSFLGAR | 606 |
| | LLAGPFR | 607 |

TABLE 3-continued

| Target Protein | Amino Acid Sequence | SEQ ID NO: |
|---|---|---|
| | QTLQTRH | 608 |
| | ALGGEPRKAYQR | 609 |
| | CNHLTQKLC | 610 |
| | CTSKLARHC | 611 |
| | AVYPLDLGAGMR | 612 |
| | CHRTYNSTC | 613 |
| | LDRNADSVRAVL | 614 |
| | TTNGVPGHDRSP | 615 |
| | ADMPQMTLKYGV | 616 |
| | AWNGNRS | 617 |
| | GDLLLKR | 618 |
| | VPQIRIK | 619 |
| | SWQMRSY | 620 |
| | YHLGPNQKMRTS | 621 |
| | ASHSRPLMNYAP | 622 |
| | QTRWDDGSYQIS | 623 |
| | SLAVANTRFMIR | 624 |
| | EGHVWSEYTWGT | 625 |
| | ETYKVTRVISPW | 626 |
| | GHPWTEIDFMSS | 627 |
| | KQELSDNLASHR | 628 |
| | SFRNLEKLSLWS | 629 |
| | GDLWNVP | 630 |
| | GPKNHHQ | 631 |
| | GSGFRNEEHSAH | 632 |
| | NNNAAMQNHGVR | 633 |
| | RAQAHQV | 634 |
| | CSLANPATC | 635 |
| | GEPLTRFPNSDS | 636 |
| | KPILWNRSLNAL | 637 |
| | GFADVIHRKWSS | 638 |
| | HQSLAGVPWSRH | 639 |
| | VPVFLDQARVMK | 640 |
| | DDLLTAPRLGVW | 641 |
| | SDRGKTVLHGQI | 642 |
| | CGITQTTTC | 643 |
| | CHQRQQTYC | 644 |
| | EYWHQRGSWFHR | 645 |
| | YTPRNQL | 646 |

TABLE 3-continued

| Target Protein | Amino Acid Sequence | SEQ ID NO: |
|---|---|---|
| | CTKSPSNSC | 647 |
| | WAFKAPQ | 648 |
| | GSLDMGNNKQPV | 649 |
| | AVVSQNQMSQQK | 650 |
| | CLNQKWEAC | 651 |
| | WPVRNLL | 652 |
| | GYRSFIHENWSI | 653 |
| | SGWEGKTHQGVR | 654 |
| | LQSNAADHHQGM | 655 |
| | ATSKYPNSWAQT | 656 |
| | DRLTPITWDWSR | 657 |
| | WTKHNTPAHHLS | 658 |
| | WNANYGTMTRHA | 659 |
| | HASNQRV | 660 |
| | GRTIHSM | 661 |
| | RLVTASMVSPSF | 662 |
| | DGQVSDHSYVQW | 663 |
| | KISMNRLHANFT | 664 |
| | WDLPTLRKTKQA | 665 |
| | WVAAERR | 666 |
| | MTHSAHNSQKTN | 667 |
| | WGLKLPH | 668 |
| | QGWFRHS | 669 |
| | IPVGERK | 670 |
| | CMNKIQRDC | 671 |
| | KALGYSLVGGEW | 672 |
| | APKVTNARPTQL | 673 |
| | AWVEAQNASNPS | 674 |
| | CSKHNHSRC | 675 |
| | GKPDHRLVSLWR | 676 |
| | CSHHKLKQC | 677 |
| | GGYDLPWANWQN | 678 |

TABLE 4

| Peptide | SEQ ID NO: |
|---|---|
| GWQMFPPMQNTR | 679 |
| SSLYMNGWSRDQ | 680 |
| YAGQNGWMRSDL | 681 |
| VERLNWPKRMQS | 682 |

TABLE 4-continued

| Peptide | SEQ ID NO: |
|---|---|
| WDVAWLERRALH | 683 |
| VRLPMLASMGHQ | 684 |
| DRGLTILTDDLR | 685 |
| GWNEATNSARHT | 686 |
| EFARFRVFGVAE | 687 |
| NRIGHGTATGTL | 688 |
| VTDMLGIPKLHA | 689 |
| DELVGGAPWYKS | 690 |
| GLLREPDELMFL | 691 |
| QNIVENFIDNER | 692 |
| SGEYNLIKPNLL | 693 |
| EESNAKLELLSR | 694 |
| GWANSITYRNLY | 695 |
| NYAVGDRITKNI | 696 |
| HGIVFSKRPFSN | 697 |
| FDPLSRNVPHKT | 698 |
| NAVHRPDLNLLA | 699 |
| GMRTGDDSPKYP | 700 |
| IPGQTPRMPHSK | 701 |
| KTTSMTALTMGL | 702 |
| VNYQTPWNKHWY | 703 |
| VESGHAYSVSSW | 704 |
| VRSDMVSGGLQK | 705 |
| YANGIEAKDSSR | 706 |
| YAWDTVASRNYK | 707 |
| LQTHSITYRHER | 708 |
| SLGSSFVQGGEL | 709 |
| WEKHTGPLSRYL | 710 |
| AFRFEFQVPDSH | 711 |
| GHAHSLTQNPLF | 712 |
| GLTIMSSRHSLQ | 713 |
| NGMNWLQVHQLS | 714 |
| WSGGMEDNSNRL | 715 |
| AIMSYNSPWIQG | 716 |
| DVMQMFHQVHFY | 717 |
| QANLYYWDPSDL | 718 |
| QRATNDILIRGW | 719 |
| SPMANVWFNRLS | 720 |
| YSANSNPKKSLM | 721 |

TABLE 4-continued

| Peptide | SEQ ID NO: |
| --- | --- |
| ALNHNGPVKTGL | 722 |
| DASQYPLVSGLW | 723 |
| EPWQSRDKVIEE | 724 |
| GLWDGKGRIVEV | 725 |
| GTVSYMVKMDNN | 726 |
| SLQLWNSEKVTT | 727 |
| WVGPDIIAQMRI | 728 |
| EIIVMSGSNVTN | 729 |
| HSGAYTIQASYK | 730 |
| MLKMERPGRMAY | 731 |
| SDHTFKRVMFRW | 732 |
| EMVPMKFLMMAK | 733 |
| NTEYSRYTSIWK | 734 |
| TDNGSFLGKLTS | 735 |
| TEWMVRASSIGE | 736 |
| VPVPKKMSLDPT | 737 |
| WPLKRFEQLPLK | 738 |
| MLRHVDLTEPNA | 739 |
| QSTLGVHMLRVS | 740 |
| RTVITNEMLLLV | 741 |
| SEPIEKGSRTIV | 742 |
| TLNARDQLSING | 743 |
| GTALNLQKDINK | 744 |
| SGWHLVMSMSIG | 745 |
| TSAHHDRTLAGS | 746 |

Accordingly, in embodiments, a peptide comprises, or consists of, an amino acid sequence selected from the group consisting of SEQ ID NOS:18, 19, 29-82, 84-95, and 103-746. In embodiments, a peptide comprises, or consists of, an amino acid sequence selected from the group consisting of SEQ ID NOS:18, 19, 29-82, 84-95, and 103-746. In embodiments, a peptide comprises, or consists of, an amino acid sequence selected from the group consisting of SEQ ID NOS:75-82 84-95, and 103-746. In embodiments, a peptide comprises, or consists of, an amino acid sequence selected from the group consisting of SEQ ID NOS:55-74 and 188-362. In embodiments, a peptide comprises, or consists of, an amino acid sequence selected from the group consisting of SEQ ID NOS:75-82, 84-95, and 103-187. In embodiments, a peptide comprises, or consists of, an amino acid sequence selected from the group consisting of SEQ ID NOS:33-54 and 363-446. In embodiments, a peptide comprises, or consists of, an amino acid sequence selected from the group consisting of SEQ ID NOS:18, 19, 29-32, and 447-471. In embodiments, a peptide comprises, or consists of, an amino acid sequence selected from the group consisting of SEQ ID NOS:472-678. In embodiments, a peptide comprises, or consists of, an amino acid sequence selected from the group consisting of SEQ ID NOS:679-746.

In embodiments, a peptide comprises, or consists of, a variant of an amino acid sequence described in International Patent Application No. PCT/US21/61821 ("the '821 Application"). Such variants therefore include, without limitation, peptides comprising or consisting of amino acid sequences that share 75%-99% identity or 75%-99% homology with any one of SEQ ID NOS:18, 19, 29-82, 84-95, and 103-746.

In embodiments, a peptide comprises, or consists of, an amino acid sequence having at least 75% identity to any one of SEQ ID NOS:18, 19, 29-82, 84-95, and 103-746. In embodiments, the peptide comprises, or consists of, an amino acid sequence having at least 80% identity to any one of SEQ ID NOS:18, 19, 29-82, 84-95, and 103-746. In embodiments, the peptide comprises, or consists of, an amino acid sequence having at least 85% identity to any one of SEQ ID NOS:18, 19, 29-82, 84-95, and 103-746. In embodiments, the peptide comprises, or consists of, an amino acid sequence having at least 90% identity to any one of SEQ ID NOS:18, 19, 29-82, 84-95, and 103-746. In embodiments, the peptide comprises, or consists of, an amino acid sequence having at least 95% identity to any one of SEQ ID NOS:18, 19, 29-82, 84-95, and 103-746.

In embodiments, a peptide consists of or comprises an amino acid sequence sharing at least 80% homology with any one of SEQ ID NOS:18, 19, 29-82, 84-95, and 103-746. In embodiments, a peptide comprises, or consists of, an amino acid sequence sharing at least 85% homology with any one of SEQ ID NOS:18, 19, 29-82, 84-95, and 103-746. In embodiments, a peptide comprises, or consists of, an amino acid sequence sharing at least 90% homology any one of SEQ ID NOS:18, 19, 29-82, 84-95, and 103-746. In embodiments, a peptide comprises, or consists of, an amino acid sequence sharing at least 95% homology with any one of SEQ ID NOS:18, 19, 29-82, 84-95, and 103-746. In embodiments, a peptide comprises, or consists of, an amino acid sequence sharing at least 99% homology any one of SEQ ID NOS:18, 19, 29-82, 84-95, and 103-746.

The peptides of the present invention are synthesized by any suitable method known to one of skill in the art, including those disclosed in the '054 and '821 Applications, as incorporated herein. For examples, peptides of the present invention can be chemically synthesized by solid phase peptide synthesis. In embodiments, peptides of the present invention are acetylated at the N-terminus ("Ac" or "acetyl"), amidated at the C-terminus ("CONH$_2$" or "NH$_2$"), or both. For example, SEQ ID NO:747 corresponds to an amidated peptide, terminating with a glycinamide.

Fluorescent Moieties

As used herein, the term "fluorescent moiety" means any fluorescent molecule, including a fluorescent protein, a fluorescent peptide, a fluorophore (such as a fluorescent dye), or any other fluorescent ligand or marker.

Specific examples of fluorescent moieties described herein are illustrative only and not meant to limit the fluorescent moieties for use with the peptides disclosed herein.

Fluorophores (or fluorescent dyes) include molecules that function in the visible, as well as near infrared (NIR) region.

Common classes of fluorophores include, but are not limited to, xanthenes, such as rhodamines, rhodols and fluoresceins, and their derivatives; bimanes; coumarins and their derivatives such as umbelliferone and aminomethyl coumarins; aromatic amines such as dansyl; squarate dyes; benzofurans; fluorescent cyanines; carbazoles; dicyanomethylene pyranes; polymethines; oxabenzanthrane; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; rare-earth metal chelate complexes; and derivatives thereof. Fluorescent dyes are discussed, for example, in U.S. Pat. Nos. 4,452,720; 5,227,487; and 5,543,295.

Typical fluorescein dyes for use with the conjugates disclosed herein include, but are not limited to, carboxyfluorescein, 5-carboxyfluorescein, 6-carboxyfluorescein, 5(6)-carboxyfluorescein, fluorescein isothiocyanate, fluorescein-5-isothiocyanate, fluorescein-6-isothiocyanate, 5,6-dicarboxyfluorescein, 5- (and 6)-sulfofluorescein, sulfonefluorescein, succinyl fluorescein, 5- (and 6)-carboxy SNARF-1, carboxyfluorescein sulfonate, carboxyfluorescein zwitterion, carboxyfluorescein quaternary ammonium, carboxyfluorescein phosphonate, carboxyfluorescein GABA, carboxyfluorescein-cys-Cy5, and fluorescein glutathione. Examples of fluorescein dyes can also be found, for example, in U.S. Pat. Nos. 6,008,379, 5,750,409, 5,066,580, and 4,439,356.

In embodiments, the fluorescent moiety comprises a carboxyfluorescein molecule (FAM), namely a fluorescein molecule with an added carboxyl group. The term "FAM" can therefore include a fluorescein molecule with a carboxyl group in the 5-position (5-FAM) or in the 6-position (6-FAM).

In embodiments, a fluorescent moiety can include IR800CW, cyan fluorescent protein (CFP); EGFP; 5-FAM; 6-FAM; FAM; fluorescein; IAEDANS; EDANS; BODIPY FL; TRITC; Cy5; Cy3; YFP; LC Red 640; Alexa Fluor 546; tetramethylrhodamine; Dabcyl; QSY 7; QSY 9; QSY 21; and BBQ-650 dyes.

In embodiments, a fluorescent moiety comprises a rhodamine dye, such as, for example, 5- (and 6)-carboxy rhodamine 110, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (TEXAS RED), and other rhodamine dyes. Other rhodamine dyes can be found, for example, in U.S. Pat. Nos. 6,080,852; 6,025,505; 5,936,087; 5,750,409.

In embodiments, a fluorescent moiety includes a cyanine dye, such as, for example, Cy2, Cy3, Cy3B, Cy3.5, Cy5, Cy5.5, Cy 7, and indocyanine green.

In embodiments, the fluorophore exhibits green fluorescence (for example 494 nm/519 nm or 494/524 nm), orange fluorescence (for example 554 nm/570 nm), red fluorescence (for example 590 nm/617 nm), or far red fluorescence (for example 651 nm/672 nm) excitation/emission spectra. In embodiments, the fluorophore is a fluorophore with excitation and emission spectra in the range of about 350 nm to about 775 nm. In embodiments the excitation and emission spectra are about 346 nm/446 nm, about 494 nm/519 nm, about 554 nm/570 nm, about 555 nm/572 nm, about 590 nm/617 nm, about 651 nm/672 nm, about 679 nm/702 nm or about 749 nm/775 nm.

In embodiments, the excitation and emission spectrum of the fluorophore are in the visible spectral region (about 380 nm to about 700 nm).

In embodiments, the excitation and emission spectrum of the fluorophore are in the near infrared (NIR) range, including the NIR-I spectral region (about 700 nm to about 900 nm) and NIR-II spectral region (about 1000 nm to about 1700 nm). See, e.g., Zhu et al. 2018, *Theranostics* 8, 4141-4151.

In embodiments, the fluorophore can include but is not limited to AlexaFluor 3, AlexaFluor 5, AlexaFluor 350, AlexaFluor 405, AlexaFluor 430, AlexaFluor 488, AlexaFluor 500, AlexaFluor 514, AlexaFluor 532, AlexaFluor 546, AlexaFluor 555, AlexaFluor 568, AlexaFluor 594, AlexaFluor 610, AlexaFluor 633, AlexaFluor 647, AlexaFluor 660, AlexaFluor 680, AlexaFluor 700, and AlexaFluor 750 (Molecular Probes AlexaFluor dyes, available from Life Technologies, Inc. (USA)). In embodiments, the fluorophore can include but is not limited to Cy dyes, including Cy2, Cy3, Cy3B, Cy3.5, Cy5, Cy5.5 and Cy7 (available from GE Life Sciences or Lumiprobes). In embodiments the fluorophore can include but is not limited to DyLight 350, DyLight 405, DyLight 488, DyLight 550, DyLight 594, DyLight 633, DyLight 650, DyLight 680, DyLight 750 and DyLight 800 (available from Thermo Scientific (USA)). In embodiments, the fluorophore can include but is not limited to a FluoProbes 390, FluoProbes 488, FluoProbes 532, FluoProbes 547H, FluoProbes 594, FluoProbes 647H, FluoProbes 682, FluoProbes 752 and FluoProbes 782, AMCA, DEAC (7-Diethylaminocoumarin-3-carboxylic acid); 7-Hydroxy-4-methylcoumarin-3; 7-Hydroxycoumarin-3; MCA (7-Methoxycoumarin-4-acetic acid); 7-Methoxycoumarin-3; AMF (4'-(Aminomethyl)fluorescein); 5-DTAF (5-(4,6-Dichlorotriazinyl)aminofluorescein); 6-DTAF (6-(4,6-Dichlorotriazinyl)aminofluorescein); FAM (Carboxyfluorescein); 6-FAM (6-Carboxyfluorescein), 5(6)-FAM cadaverine; 5-FAM cadaverine; 5(6)-FAM ethylenediamme; 5-FAM ethylenediamme; 5-FITC (FITC Isomer I; fluorescein-5-isothiocyanate); 5-FITC cadaverin; Fluorescein-5-maleimide; 5-IAF (5-Iodoacetamidofluorescein); 6-JOE (6-Carboxy-4',5'-dichloro-2',7'-dimethoxyfluorescein); 5-CR110 (5-Carboxyrhodamine 110); 6-CR110 (6-Carboxyrhodamine 110); 5-CR6G (5-Carboxyrhodamine 6G); 6-CR6G (6-Carboxyrhodamine 6G); 5(6)-Carboxyrhodamine 6G cadaverine; 5(6)-Caroxyrhodamine 6G ethylenediamme; 5-ROX (5-Carboxy-X-rhodamine); 6-ROX (6-Carboxy-X-rhodamine); 5-TAMRA (5-Carboxytetramethylrhodamine); 6-TAMRA (6-Carboxytetramethylrhodamine); 5-TAMRA cadaverine; 6-TAMRA cadaverine; 5-TAMRA ethylenediamme; 6-TAMRA ethylenediamme; 5-TMR C6 maleimide; 6-TMR C6 maleimide; TR C2 maleimide; TR cadaverine; 5-TRITC; G isomer (Tetramethylrhodamine-5-isothiocyanate); 6-TRITC; R isomer (Tetramethylrhodamine-6-isothiocyanate); Dansyl cadaverine (5-Dimethylaminonaphthalene-1-(N-(5-aminopentyl))sulfonamide); EDANS C2 maleimide; fluorescamine; NBD; and pyrromethene and derivatives thereof.

In embodiments, a fluorescent moiety comprises an environmentally sensitive fluorescent dye or fluorophore. Examples of environmentally sensitive fluorescent dyes or fluorophores include 5,6-carboxy-diethyl rhodol (pH sensitive), merocyanine (membrane potential sensitive), and Nile red carboxylic acid (lipid sensitive).

In embodiments, the fluorescent moiety is a fluorescent peptide or fluorescent protein. In embodiments, the fluorescent protein is Green Fluorescent Protein (GFP). In embodiments, the fluorescent moiety is a derivative or variant of GFP, including for example: EGFP, emerald, superfolder GFP, azami green mWasabi, TagGFP, TurboGFP, AcGFP, ZsGreen, T-Sapphire, EBFP, EBFP2, Azurite, mTagBFP, ECFP, mECFP, Cerulean, mTurquoise, CyPet, AmCyanl, Midori-Ishi Cyan, TagCFP, mTFP1 (Teal), EYFP, Topaz, Venus, mCitrine, YPet, TagYFP, PhiYFP, ZsYellowl, mBanana, Kusabira Orange, Kusbira Orange2, mOrange, mOrange2, dTomato, dTomato-Tandem, TagRFP, TagRFP-Y, DsRed, DsRed2, DsRed-Express (T1), DsRed-Monomer, mTangerine, mRuby, mApple, mStrawberry, AsRed2, mRFP1, JRed, mCherry, HcRed1, mRaspberry, dKeima-Tandem, HcRed-Tandem, mPlum, AQ143, mKalama1, YFP, and Citrine.

In embodiments, the fluorescent moiety includes a fluorescent molecule, as disclosed in the '054 and '821 Applications, which are incorporated in their entireties herein.

In embodiments, the fluorescent moiety is conjugated to high molecular weight molecule, such as water soluble polymers including, but not limited to, dextran, PEG, serum albumin, or poly(amidoamine) dendrimer.

A fluorescent moiety disclosed herein may be bound to the N-terminus, C-terminus, or an internal position (e.g., to an internal amino acid) of the peptide. In embodiments, two, three, four or more peptides are directly or indirectly bound to a fluorescent moiety. In embodiments, any peptide disclosed herein is bound to two or more fluorescent moieties, which may be the same or different.

In embodiments, a fluorescent moiety disclosed herein is bound directly to any peptide disclosed herein.

Linkers

In embodiments, the fluorescent moiety is bound indirectly to the peptide, e.g., via a linker. As used herein, a "linker" is any molecule capable of binding (e.g., covalently) to a peptide disclosed herein. Linkers include, but are not limited to, straight or branched-chain carbon-containing linkers, heterocyclic carbon-containing linkers, amino acid linkers (e.g., D- or L-amino acid), lipophilic residues, peptide linkers, peptide nucleic acid linkers, hydrazone linkers, SPDB disulfide, sulfo-SPDB, maleimidomethyl cyclohexane-1-carboxylate (MCC), aminohexanoic acid linkers, and polyether linkers (e.g., PEG). Linkers include, for example, poly(ethylene glycol) linkers available from Quanta Biodesign, Powell, OH. These linkers optionally have amide linkages, sulfhydryl linkages, or hetero functional linkages. Linkers also include other linker molecules as disclosed or described in the art, including those described in the '054 and '821 Applications, as incorporated herein.

In embodiments, the linker binds to a targeting molecule disclosed herein by a covalent linkage. A linker may connect a cargo molecule, such as a fluorescent moiety, to a peptide by forming a covalent linkage to the cargo molecule at one location and a covalent linkage to the peptide at another location. The covalent linkages can be formed by reaction between functional groups on the linker and functional groups on the peptide and on the cargo molecule. In embodiments, the covalent linkage comprises an ether bond, thioether bond, amine bond, amide bond, carbon-carbon bond, carbon-nitrogen bond, carbon-oxygen bond, or carbon-sulfur bond. For example, a covalent linkage can be formed by a condensation reaction between a carboxylic acid functional group at the 5-position of fluorescein and the primary amine at the N-terminus of a peptide, such as in the fluorescent conjugate 5-FAM-QVPWEEPYYVVKKSSGG-NH2 (HNP401-N-2 with GG linker; SEQ ID NO:747).

In embodiments, the linker is flexible. In embodiments, the linker is rigid. In embodiments, the linker has segment(s) of flexibility and segment(s) of rigidity.

In embodiments, the linker comprises a linear structure. In embodiments, the linker comprises a non-linear structure. In embodiments, the linker comprises a branched structure. In embodiments, the linker comprises a cyclic structure.

In embodiments, the linker is an alkyl. In embodiments, the linker is heteroalkyl.

In embodiments, the linker is an alkylene. In embodiments, the linker is an alkenylene. In embodiments, the linker is an alkynylene. In embodiments, the linker is a heteroalkylene.

An "alkyl" group refers to an aliphatic hydrocarbon group. The alkyl moiety may be a saturated alkyl or an unsaturated alkyl. Depending on the structure, an alkyl group can be a monoradical or a diradical (i.e., an alkylene group).

The "alkyl" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). The alkyl group could also be a "lower alkyl" having 1 to 6 carbon atoms. The alkyl group of the compounds described herein may be designated as "C1-C4 alkyl" or similar designations. By way of example only, "C1-C4 alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, ethenyl, propenyl, butenyl, and the like.

In embodiments, the linker comprises a ring structure (e.g., an aryl). As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyl groups include groups having from 3 to 10 ring atoms. Cycloalkyls include, but are not limited to, cyclopropyl, cyclobutyl, cyclopentyl, cyclohexyl, cycloheptyl, and cyclooctyl.

In embodiments, the ring is a cycloalkane. In embodiments, the ring is a cycloalkene.

In embodiments, the ring is an aromatic ring. The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

In embodiments, the ring is a heterocycle. The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and faropyridinyl. The foregoing groups, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group).

In embodiments, the ring is fused. The term "fused" refers to structures in which two or more rings share one or more bonds. In embodiments, the ring is a dimer. In embodiments, the ring is a trimer. In embodiments, the ring is a substituted.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e., a heteroatom). Heterocycle includes heteroaryl and heterocycloalkyl. Carbocycles and heterocycles can be optionally substituted.

In embodiments, the linker is substituted. The term "optionally substituted" or "substituted" means that the referenced group may be substituted with one or more additional group(s) individually and independently selected from Ci-Cealkyl, C3-Cgcycloalkyl, aryl, heteroaryl, C2-C6heteroalicyclic, hydroxy, Ci-C6alkoxy, aryloxy, Ci-C6alkylthio, arylthio, Ci-C6alkylsulfoxide, arylsulfoxide, Ci-C6alkylsulfone, arylsulfone, cyano, halo, C2-C8acyl, C2-C8acyloxy, nitro, Ci-C6haloalkyl, Ci-C6fluoroalkyl, and amino, including Ci-C6alkylamino, and the protected derivatives thereof. By way of example, an optional substituents may be LSRS, wherein each Ls is independently selected from a bond, —O—, —C(=O)—, —S—, —S(=O)—, —S(O)$_2$—, —NH—, —NHC(O)—, —C(O)NH—, S(O)2NH—, —NHS(O)2-, —OC(O)NH—, —NHC(O)O—, —(CpC6alkyl)-, or —(C2-C6alkenyl)-; and each Rs is independently selected from H, (Ci-C4alkyl), (C3-C8cycloalkyl), heteroaryl, aryl, and Ci-C6heteroalkyl. Optionally substituted non-aromatic groups may be substituted with one or more oxo (=O). The protecting groups that may form the protective derivatives of the above substituents are known to those of skill in the art.

In embodiments, a bifunctional linker having one functional group reactive with a group on one molecule (e.g., a targeting molecule), and another group reactive on the other molecule (e.g., a fluorescent moiety or a drug), is used to form the desired conjugate. Alternatively, derivatization is performed to provide functional groups. Thus, for example, procedures for the generation of free sulfhydryl groups on peptides are also known (See U.S. Pat. No. 4,659,839). A linker may alternatively comprise a heterobifunctional crosslinker comprising two or more different reactive groups that form a heterocyclic ring that can interact with a targeting molecule. For example, a heterobifunctional crosslinker such as cysteine may comprise an amine reactive group and a thiol-reactive group can interact with an aldehyde on a derivatized targeting molecule. Additional combinations of reactive groups suitable for heterobifunctional crosslinkers include, for example, amine- and sulfhydryl reactive groups; carbonyl and sulfhydryl reactive groups; amine and photoreactive groups; sulfhydryl and photoreactive groups; carbonyl and photoreactive groups; carboxylate and photoreactive groups; and arginine and photoreactive groups. Examples of a heterobifunctional crosslinker include N-Succinimidyl 4-(2-pyridyldithio)butanoate (SPDB) and maleimidomethyl cyclohexane-1-carboxylate (MCC).

In embodiments, a linker is cleavable. In embodiments, the linker is non-cleavable. A linker can be chemically stable to extracellular environments, for example, chemically stable in the blood stream, and/or may include linkages that are not stable. A linker can include linkages that are designed to cleave and/or immolate or otherwise breakdown specifically or non-specifically inside cells. A cleavable linker can be sensitive to enzymes at a specific site, such as by extracellular proteases.

A cleavable linker can include a valine-citrulline peptide, a valine-alanine peptide, a phenylalanine-lysine or other peptide, such as a peptide that forms a protease recognition and cleavage site. Such a peptide-containing linker can contain a pentafluorophenyl group. A peptide-containing linker can include a succimide or a maleimide group. A peptide-containing linker can include a para aminobenzoic acid (PABA) group. A peptide-containing linker can include an aminobenzyloxycarbonyl (PABC) group. A peptide-containing linker can include a PABA or PABC group and a pentafluorophenyl group. A peptide-containing linker can include a PABA or PABC group and a succinimide group. A peptide-containing linker can include a PABA or PABC group and a maleimide group.

A non-cleavable linker is generally protease-insensitive and insensitive to intracellular processes. A non-cleavable linker can include a maleimide group. A non-cleavable linker can include a succinimide group. A non-cleavable linker can be maleimido-alkyl-C(O)— linker. A non-cleavable linker can be maleimidocaproyl linker. A maleimidocaproyl linker can be N-maleimidomethylcyclohexane-1- carboxylate. A maleimidocaproyl linker can include a succinimide group. A maleimidocaproyl linker can include pentafluorophenyl group.

In embodiments, a peptide linker consisting of one or more amino acids is used to join the targeting molecule and a fluorescent moiety or drug. Generally the peptide linker will have no specific biological activity other than to join the molecules or to preserve some minimum distance or other spatial relationship between them. However, the constituent amino acids of the linker may be selected to influence some property of the molecule such as the folding, net charge, or hydrophobicity. In embodiments the peptide linker is relatively short, typically less than about 10 amino acids, preferably less than about 8 amino acids and more preferably less than 5 amino acids. Non-limiting illustrative examples include glycine and glycine-serine linkers which can be added to the C-terminus of a peptide. In embodiments, a peptide linker comprises a cysteine residue or an unnatural amino acid residue, e.g., selenocysteine (Sec), p-acetophenylalanine (pAcF), p-azidomethyl-L-phenylalanine (pAMF), and azido-lysine (AzK)) for site specific conjugation. In embodiments, a peptide linker is a glycine-glycine-glycine-cysteine (GGGC) (SEQ ID NO:15) linker, a glycine-glycine-cysteine (GGC) linker, a glycine-glycine (GG) linker, or a cysteine (C) linker. In embodiments, the GGGC (SEQ ID NO:15), GGC, GG, or C linker is added to the N-terminus or C-terminus of a peptide.

In embodiments, the fluorescent conjugates of the present invention may optionally be conjugated to high molecular weight molecules that increase their multivalency and avidity of binding. In embodiments, the high molecular weight molecules are water-soluble polymers. Examples of suitable water-soluble polymers include, but are not limited to, peptides, saccharides, poly(vinyls), poly(ethers), poly(amines), poly(carboxylic acids) and the like. In embodiments, the water-soluble polymers is dextran, polyethylene glycol (PEG), polyoxyalkylene, polysialic acid, starch, or hydroxyethyl starch. Any suitable method is used to conjugate peptides to water-soluble polymers (see, Hermanson G., Bioconjugate Techniques 2nd Ed., Academic Press, Inc. 2008).

In embodiments, the fluorescent conjugates of the present invention may be modified to increase solubility. Peptide modifications that increase solubility include addition of hydrophilic amino acid(s), a PEG moiety, or both. In embodiments, a PEG moiety is 8-Amino-3,6-dioxaoctanoic acid (AEEA); 12-amino-4,7,10-trioxadodecanoic acid; or 15-amino-4,7,10,13-tetraoxapenta-decanoic acid. In embodiments, approximately one to ten (e.g., one, two, three, four, five, six, seven, eight, nine, or ten) hydrophilic amino acids may be added to the N-terminus, C-terminus, an internal position, or any combination thereof, of the peptide to increase solubility. Hydrophilic amino acids include D, E, H, K, N, Q, R, S, T, and G. In embodiments, the peptide comprises a K, KK, G, or GG at the N-terminus or C-terminus.

In embodiments, the fluorescent conjugate comprises 5-FAM-QVPWEEPYYVVKKSSGG-NH2 (HNP401-N-2 with GG linker; SEQ ID NO:747) and can be used in any of the methods described herein.

In embodiments, the fluorescent conjugate comprises FAM linked to the C-terminal cysteine of HNP401 with GCC linker (Ac-SGQVPWEEPYYVVKKSSGGC-CONH$_2$; SEQ ID NO:748).

IV. Pharmaceutical Compositions

Disclosed herein, in certain embodiments, are pharmaceutical compositions comprising a fluorescent conjugate disclosed herein. Pharmaceutical compositions herein are formulated using one or more physiologically acceptable carriers, including excipients and auxiliaries, which facilitate processing of the active agents into preparations which are used pharmaceutically. Proper formulation is dependent upon the route of administration chosen. Such compositions can be prepared with methods and excipients known in the art, as found, for example, in Gennaro: *Remington: The Science and Practice of Pharmacy*, 21$^{st}$ Ed. (Lippincott Williams & Wilkins, 2005); Allen: *Ansel's Pharmaceutical Dosage Forms and Drug Delivery Systems*, 11th Ed. (Wolters Kluwer, 2018); Brunton et al.: *Goodman & Gilman's The Pharmacological Basis of Therapeutics* (McGraw-Hill Professional, 2005); and Rowe: *Handbook of Pharmaceutical Excipients* (Pharmaceutical Press, 2005).

In embodiments of pharmaceutical compositions, a peptide in a fluorescent conjugate can consist of, or comprise, any amino acid sequence, including all variants and combinations, described herein. In embodiments, a peptide consists of, or comprises. any amino acid sequence listed in Table 1, or any variant thereof, as described herein. In embodiments, a peptide comprises, or consists of, any of SEQ ID NOS:1-14, 16, 20-28, and 96-102. In embodiments, the peptide consist of, or comprises, any amino acid sequence listed in Tables 2-4, or any variant thereof. In embodiments, a peptide comprises an amino acid sequence selected from SEQ NOS:75-82 84-95, and 103-187. In embodiments, a peptide comprises an amino acid sequence selected from SEQ NOS:55-74 and 188-362. In embodiments, a peptide comprises an amino acid sequence selected from SEQ NOS:33-54 and 363-446. In embodiments, a peptide comprises an amino acid sequence selected from SEQ NOS:18, 19, and 29-32, and 447-471. In embodiments, a peptide comprises an amino acid sequence selected from SEQ ID NOS:472-678. In embodiments, a peptide comprises an amino acid sequence selected from SEQ ID NOS:679-746. In embodiments, a peptide consists or, or comprises, the amino acid sequence of SEQ ID NO:21.

In embodiments, the fluorescent conjugate in a pharmaceutical composition comprises SEQ ID NO:747.

In embodiments, a pharmaceutical composition disclosed herein further comprises a pharmaceutically acceptable diluent, excipient, carrier, or solvent. Examples of suitable aqueous and non-aqueous carriers, diluents, solvents, or vehicles include water, ethanol, polyols (propylene glycol, polyethylene-glycol, glycerol, cremophor and the like), suitable mixtures thereof, vegetable oils (such as olive oil) and injectable organic esters such as ethyl oleate. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Bioavailability enhancers may include penetration or permeation enhancers. See, e.g., Muheem et al., 2016, *Saudi Pharm. J.* 24, 413-428; Brayden et al. 2020, *Adv. Drug Deliv. Rev.* 2020 May 29:S0169-409X(20)30040-5; Ibrahim et al. 2020, *J. Pham. Sci.* 28, 403-416. In some formulations, proper fluidity can be maintained, for example, by the use of a coating such as lecithin, by the maintenance of the required particle size in the case of dispersions, and by the use of surfactants.

In embodiments, the pharmaceutical compositions include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions also contain other therapeutically valuable substances.

In embodiments, peptide conjugates disclosed herein are delivered to a subject via a drug delivery vehicle or carrier. In embodiments, a delivery vehicle is made from natural or synthetic materials or both. In embodiments, a delivery vehicle is a nanoparticle, microparticle, polymeric micelle, nanocapsule, dendrimer, large PEG, nanogel, liposome, fullerene, nanostructured lipid carrier, nanoshell, quantum dot, protein-based nanocarriers (e.g., albumin, elastin, gliadin, legumin, zein, soy protein, milk protein, whey based nanocarriers), organic nanocarrier (e.g., gelatin, dextran, guar gum, chitosan, collagen), polysaccharide based carrier (e.g., dextran, chitosan, pectin), lipid emulsion, or a combination thereof.

In embodiments, a pharmaceutical composition disclosed herein is administered to a subject by any suitable administration route, including but not limited to, topical, oral, intrarectal, intravaginal, intranasal, inhalation, parenteral (intravenous, intraarterial, subcutaneous, intraperitoneal, intramuscular, intravascular, intrathecal, intravitreal, infusion) administration. In certain embodiments, a pharmaceutical composition disclosed herein is administered to a subject is administered locally or systemically. In embodiments, a pharmaceutical composition disclosed herein is administered intravenously.

Formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Formulations suitable for subcutaneous injection also contain optional additives such as preserving, wetting, emulsifying, and dispensing agents, as are known in the art. In embodiments, formulations suitable for intravenous injection may be prepared in aqueous solutions, such as saline buffers and other physiologically compatible buffers known in the art. For intravenous injections, an active agent is optionally formulated in aqueous solutions, preferably in physiologically compatible buffers such as Hank's solution, Ringer's solution, or physiological saline buffer.

Parenteral injections optionally involve bolus injection or continuous infusion. Formulations for injection are optionally presented in unit dosage form, e.g., in ampoules or in multi dose containers, with an added preservative. In embodiments, the pharmaceutical composition described herein are in a form suitable for parenteral injection as sterile suspensions, solutions or emulsions in oily or aqueous vehicles, and contain formulation agents such as suspending, stabilizing and/or dispersing agents. Pharmaceutical formulations for parenteral administration include aqueous solutions of an active agent in water soluble form. Additionally, suspensions are optionally prepared as appropriate oily injection suspensions.

In embodiments, a pharmaceutical composition herein is administered orally. Dosage forms suitable for oral administration can be solid or liquid and may include for example, a pill, capsule, troche, tablet, caplet, gel caplet (gel cap), syrup, an aqueous suspension or solution, a chewable form, a swallowable form, a dissolvable form, an effervescent, a granulated form, and an oral liquid solution. In a specific embodiment, the dosage form is a solid dosage form, and more specifically, comprises a tablet or capsule, or is orally administered by a vehicle or carrier as disclosed herein.

In embodiments, a pharmaceutical composition described herein is in a unit dosage form suitable for single administration of precise dosages. In unit dosage form, the formulation is divided into unit doses containing appropriate quantities of an active agent disclosed herein. In embodiments, the unit dosage is in the form of a package containing discrete quantities of the formulation. Non-limiting examples are packaged tablets or capsules, and powders in vials or ampoules. In embodiments, aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

In embodiments, a pharmaceutical composition is administered via systemic intravenous to subjects, particularly, human patients, and more particularly, human patients undergoing surgery.

In embodiments, a pharmaceutical composition is administered orally to subjects, particularly, human patients, and more particularly, human patients undergoing surgery.

EXAMPLE 1

Use of Nerve Targeting Fluorescent Conjugates in Ureter Visualization

INTRODUCTION

Phage display screens were previously carried out to identify peptides that bind to human nerve homogenates or to isolated human nerve proteins. See the '054 and '821 Applications. Such peptides can be linked or tagged to cargo molecules for various applications. If tagged with a fluorescent moiety, for example, such conjugates are potentially useful for in vivo labeling of nerves during fluorescence assisted surgery, and if linked to an active agent, for example, such conjugates are potentially useful as targeted therapies.

Exemplary peptides were conjugated to fluorescent dyes to generate fluorescent conjugates (also referred to here as conjugates) and evaluated in rodent models, where they showed sensitive nerve detection following intravenous administration. These conjugates included FAM-NP41, which comprises the fluorescent dye, carboxyfluorescein (FAM), coupled to the C-terminal lysine of acetylated NP41 (Ac-SHSNTQTLAKAPEHTGK; SEQ ID NO:749) via a lysinamide linkage, as well as FAM-HNP401, which comprises FAM conjugated to the C-terminal cysteine of acetylated HNP401 with GCC linker (Ac-SGQVP-WEEPYYVVKKSSGGC-CONH$_2$; SEQ ID NO:748). See '054 Application; Hingorani et al. 2018, *Theranostics* 8, 4226-4237; Whitney et al. 2011, *Nat. Biotechnol.* 29, 352-356.

Further studies showed fluorescent labeling of human (and rodent) resected nerve tissues following topical administration of FAM-NP41, FAM-HNP401, and other conjugates, including N-terminal and C-terminal deletion variants of HNP401, corresponding to SEQ ID NOS:20, 22-24, and 25-28. Whitney et al. 2011, *Nat. Biotechnol.* 29, 352-356; Wu et al. 2011, *Laryngoscope* 121, 805-810; Hussain et al. 2015, *PloS One* 10, e0119600; Hingorani et al. 2018, *Theranostics* 8, 4226-4237.

These investigations, however, have not revealed conjugate properties, such as activity, metabolism and clearance—especially in later stages following administration. In a rodent models, for example, the serum half-life of NP41

(as measured by serum fluorescence) is about ten minutes, indicating rapid clearance of the conjugate from the blood. A similar short half-life (15 minutes) in the blood was observed for FAM-HNP401. In contrast, nerve fluorescence of NP41 has a half-life of about 50 minutes and can persist at a low level in tissues for hours. Similarly, fluorescence of FAM-HNP401 was observed in rat sciatic and prostate nerves several hours after intravenous administration. See, e.g., Whitney et al. 2011, *Nat. Biotechnol.* 29, 352-356; Hingorani et al. 2018, *Theranostics* 8, 4226-4237.

Details regarding the clearance and subsequent activity of conjugates bound to nerves (or other tissues) are unclear, and it is unknown whether such properties may support other uses for the conjugates in fluorescence guided surgery. The studies described here reveal that nerve-targeting conjugates can confer sensitive and prolonged fluorescent visualization (illumination) of ureters in conjunction with renal excretion. The results support an expanded repertoire for such conjugates as a surgical adjunct. By highlighting nerves, they are useful as guiding agents in surgeries, such as head and neck surgical procedures, where they can help prevent nerve injuries. And as described here, by highlighting ureters, they are useful in other surgeries, such as a many abdominal and pelvic surgical procedures presenting a risk of ureter injuries.

Results

A rodent model was to use to evaluate the dynamics of fluorescent visualization of 5-FAM-QVP-WEEPYYVVKKSSGG-NH2 (HNP401-N-2 with GG linker; SEQ ID NO:747) following intravenous administration. The conjugate was administered in a wide range of amounts and fluorescence was detected using a customized microscope. As shown, for example, in FIG. 1, a ureter is readily illuminated 2 hours following intravenous administration of about 2000 nanomoles (~200 mg/kg) in a mouse model. Additional investigations, exploring a range of amounts from 100 nanomoles to 2000 nanomoles, corresponding to doses from ~10 mg/kg to ~200 mg/kg, also revealed ureter illumination following intravenous administration of the fluorescent conjugate, SEQ ID NO:747, in a mouse model. Similar findings were observed in a rat model. Such fluorescent visualization does not, however, reflect specific or direct labeling of the ureter. Rather it reflects fluorescence of urine flowing down the ureter from the kidney to the bladder. Moreover, real time intraoperative imaging reveals ureteral pulsations that concentrate the urine and can enhancing fluorescence visualization of the ureter. Further studies revealed an extended time course of ureter illumination following administration of this conjugate. For example, fluorescent visualization of the ureter was observed in less than 1 hour, as well as up to at least 6 hours, following conjugate administration.

Other investigations in rodent models have demonstrated extended ureter illumination following administration of other conjugates comprising additional peptides and fluorescent moieties. These include molecules consisting of related HNP401 peptides conjugated to FAM, as well as molecules consisting of related HNP401 peptides conjugated to other fluorescent moieties. In addition, the studies presented here allow concurrent visualization of nerves in conjunction with ureters.

Discussion

These observations support the general applicability of the nerve targeting fluorescent conjugates described herein in ureter illumination. Accordingly, conjugates disclosed herein can be used to assist surgeons in the visualization of ureters during surgical procedures prior to physically encountering and thus potentially damaging them. Moreover, in the case of inadvertent damage during a surgical procedure, i.e., an iatrogenic injury, such visualization allows for more rapid recognition of the injury and earlier treatment and intervention.

In addition, it has been observed that the administration of the fluorescent conjugates described herein can provide an extended period of ureter visualization following administration. Without being limited by a specific mechanism, this extended period of visualization is believed to reflect the gradual accumulation of fluorescent conjugates in neurons or nerves, such as in the peripheral nervous system, or in other tissues, followed by their gradual release, metabolism and excretion by the urinary system. Thus, in contrast to the systemic administration of a fluorescent dye alone or the direct injection of a fluorescent dye, administering peptide-fluorescent conjugates can advantageously extend the period of ureter illumination, offering both early and longer term illumination, by convenient administration that does not disrupt surgery. In addition, administration of such conjugates can offer concomitant or temporally distinct detection of nerves or ureters.

Such fluorescence-mediated assistance is particularly important during surgical procedures that present a significant risk of ureter injury, particularly iatrogenic ureteral injury (IUI) during surgical procedures. As ureters extend from the abdomen to pelvis, this risk can apply to a broad array of surgical procedures. Applicable procedures that may benefit from ureter illumination include complex abdominal and pelvic surgeries, such as gynecological, urological, and colorectal surgical procedures, as well as cardiovascular surgical procedures. They also include surgical procedures carried out on organs and systems in the vicinity of ureters, such as a kidney, bladder, prostate, uterus, male or female reproductive system, rectum, colon, small intestine, or large intestine. They can also include cancer surgical procedures, such as a prostate cancer surgical procedure, or a colorectal cancer procedure, or procedures in which enhanced visualization of ureters, as well as nerves, is desirable.

EXAMPLE 2

Bioanalysis of Fluorescent Conjugates in the Urine of Surgery Patients

Urine samples were collected 30 minutes before intravenous administration of 500 mg of parent test drug (corresponding to the fluorescent-conjugated peptide, SEQ ID NO:747), 30 minutes after infusion prior to head and neck surgery, and 22 hours later. The concentration of intact parent test drug was determined by liquid chromatography with tandem mass spectrometry (LC-MS/MS) using a qualified bioanalytical method. Also evaluated was the presence of metabolites M3-M8 (initially identified from in vitro studies) corresponding to shortened versions of the parent peptide conjugated to the fluorescent moiety. The results are shown in Table 5.

TABLE 5

| Subject | Timepoint | Test Drug (ng/mL) | Metabolites Present |
| --- | --- | --- | --- |
| 1 | 30 min | BQL* | |
| 2 | Predose | BQL | |
|   | 30 min | 11.5 | M4, M6, M7 |
|   | 22 hours | BQL | M4, M6 |

TABLE 5-continued

| Subject | Timepoint | Test Drug (ng/mL) | Metabolites Present |
|---|---|---|---|
| 3 | Predose | BQL | |
|   | 30 min | 19.0 | M4, M6, M7 |
|   | 22 hours | BQL | M4, M6 |
| 4 | Predose | BQL | |
|   | 30 min | BQL | M4, M6, M7 |
| 5 | Predose | BQL | |
|   | 30 min | 10.1 | M4, M6, M7 |

*BQL: Below Quantitation Limit (10 ng/ml)

At the 30-minute time-point, quantifiable levels of test drug (or the fluorescent metabolites M4, M6, and M7) were detected in four of five subjects evaluated. At the 22 hour time point, fluorescent metabolites M4 and M6 were detected in both subjects evaluated. As expected, test drug and fluorescent metabolites were not detected in any predose samples.

These data are consistent with dosing and ureter imaging experiments in the rodent models, indicating that a single administration of test drug can lead to immediate (e.g., 30 minutes) and prolonged accumulation (e.g., 22 hours) of fluorescent molecules in the urine. In turn, this can confer extended ureter visualization at early and later stages in surgical procedures, as well as support concurrent or distinct visualization of nerves and ureters in surgical procedures or other applications.

EXAMPLE 3

Ureter and Nerve Illumination During Surgery

The ability of fluorescent conjugates of the present disclosure to image ureters (and nerves) can be evaluated using an appropriately designed clinical study, such as that described below for patients undergoing gastrointestinal/genitourinary (GI/GU) surgery In this prophetic example, a clinical trial comprises an open-label, multi-center study evaluating administration of a test drug (corresponding to the fluorescent-conjugated peptide, SEQ ID NO: 747) in 80 subjects undergoing GI/GU surgery. Inclusion criteria for enrollment in the study include the requirement that the subject is undergoing a surgical procedure in the GI/GU region where nerves (and ureters) are potentially at risk for injury. For example, such procedures can encompass colorectal or prostate surgery.

Enrolled subjects receive a single dose of test drug (500 mg) by intravenous infusion 2 to 5 hours prior to surgery. Fluorescence of test drug is evaluated by real-time white light reflectance (WLR) and fluorescence (FL) imaging through a laparoscope.

Multiple endpoints are used to assess primary and secondary efficacy objectives.

With respect to nerve detection, the endpoints include a visualization scoring system to measure the efficacy of test drug in improving the contrast enhancement, branching delineation, and length of nerves using WLR alone versus Paired (WLR with FL overlay). They also include computation of signal to background ratio for multiple regions of nerve (and adjacent non-nerve) tissue to measure the efficacy of test drug in improving nerve visualization using WLR versus FL.

With respect to ureter detection, the endpoints include a visualization scoring system to measure the efficacy of test drug in improving the contrast enhancement of ureter using WLR alone versus WLR with FL overlay. They also include computation of signal to background ratio for multiple regions of ureter (and adjacent non-ureter) tissue to measure the efficacy of test drug in improving ureter visualization using WLR versus FL.

A significant improvement in the efficacy of nerve and ureter detection with test drug is shown with multiple endpoints. Improvement is observed at early and later times in the surgical procedures. Accordingly, fluorescent conjugates of the present disclosure can be useful in fluorescent guided GI/GU surgical procedures, including in enhanced visualization of nerves, ureters, or both. Benefits of such enhanced visualization can include significant improvements in surgeon confidence in identifying ureters and nerves in surgical procedures, as well as significant reductions in the duration of such surgical procedures.

The examples set forth above are provided to give those of ordinary skill in the art a complete disclosure and description of how to make and use the embodiments of the compositions and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

Furthermore while certain details in the present disclosure are provided to convey a thorough understanding of the invention as defined by the appended claims, it will be apparent to those skilled in the art that certain embodiments may be practiced without these details. Moreover, in certain instances, well-known methods, procedures, or other specific details have not been described to avoid unnecessarily obscuring aspects of the invention defined by the appended claims.

This application claims the benefit of priority to U.S. Provisional Application No. 63/137,621, filed Jan. 14, 2021, which application is hereby incorporated by reference in its entirety.

The invention claimed is:

1. A method of visualizing a ureter in a subject, the method comprising
   (a) administering to the subject an effective amount of a fluorescein-conjugated peptide, wherein the fluorescein-conjugated peptide comprises a peptide having the amino acid sequence of SEQ ID NO:21 conjugated to a fluorescein moiety at its N-terminus; and
   (b) detecting fluorescence of the ureter following administration of the fluorescein-conjugated peptide, wherein:
      detecting fluorescence of the ureter occurs after 1 hour, 2 hours, 3 hours, 4 hours, 5 hours, 6 hours, 7 hours, or more than 8 hours following administration of the fluorescein-conjugated peptide; and
      detecting fluorescence of the ureter comprises detecting the fluorescein moiety in a peristaltic urine flow in the ureter.

2. The method of claim 1, wherein the fluorescein moiety is carboxyfluorescein.

3. The method of claim 1, wherein the fluorescein moiety is 5-carboxyfluorescein.

4. The method of claim 1, wherein the fluorescein-conjugated peptide is SEQ ID NO: 747.

5. The method of claim 1, wherein the subject is a human subject undergoing a surgical procedure.

6. The method of claim 5, wherein the fluorescein-conjugated peptide is first administered prior to the surgical procedure.

7. The method of claim 6, wherein the fluorescein-conjugated peptide is not further administered to the subject following the first administration.

8. The method of claim 5, wherein the surgical procedure comprises a gynecological, urological, colorectal, or cardiovascular surgical procedure.

9. The method of claim 5, wherein the surgical procedure comprises an abdominal or pelvic procedure.

10. The method of claim 5, wherein the surgical procedure is performed on a kidney, bladder, prostate, uterus, male or female reproductive system, rectum, colon, small intestine, or large intestine.

11. The method of claim 5, wherein the surgical procedure is an open surgical procedure, a laparoscopic surgical procedure, a microscopic procedure, or an endoscopic procedure.

12. The method of claim 5, wherein the surgical procedure is a cancer surgical procedure.

13. The method of claim 12, wherein the cancer surgical procedure is a prostate cancer surgical procedure or colorectal cancer surgical procedure.

14. The method of claim 1, wherein detecting fluorescence of the ureter occurs within a period of at least 1 hour, at least 2 hours, at least 3 hours, at least 4 hours, at least 5 hours, at least 6 hours, at least 7 hours, or at least 8 hours, following administration of the fluorescein-conjugated peptide.

15. The method of claim 1, wherein detecting fluorescence of the ureter occurs for a period of more than 1 hour, more than 2 hours, more than 3 hours, more than 4 hours, more than 5 hours, more than 6 hours, more than 7 hours, or more than 8 hours following administration of the fluorescein-conjugated peptide.

16. The method of claim 1, wherein the fluorescein-conjugated peptide is administered to the subject intravenously.

17. The method of claim 1, wherein the fluorescein-conjugated peptide is administered to the subject orally.

18. The method of claim 1, wherein the fluorescein-conjugated peptide is in a pharmaceutical composition further comprising a pharmaceutically acceptable excipient.

19. The method of claim 1, further comprising visualizing a nerve in the subject that is labeled by the fluorescein-conjugated peptide.

20. The method of claim 19, wherein the nerve and the ureter are visualized concurrently in the subject during surgery.

21. The method of claim 19, wherein the nerve and the ureter are visualized at different times in the subject during surgery.

22. The method of claim 5, wherein detecting fluorescence of the ureter occurs within a period of at least 8 hours following administration of the fluorescein-conjugated peptide.

23. The method of claim 5, wherein detecting fluorescence of the ureter occurs for a period of more than 1 hour following administration of the fluorescein-conjugated peptide.

24. The method of claim 5, wherein detecting fluorescence of the ureter occurs after 30 minutes following administration of the fluorescein-conjugated peptide.

25. The method of claim 5, wherein detecting fluorescence of the ureter comprises detecting the fluorescein moiety in a urine flow in the ureter.

26. The method of claim 5, wherein the fluorescein-conjugated peptide is administered to the subject intravenously.

27. The method of claim 5, further comprising visualizing a nerve in the subject that is labeled by the fluorescein-conjugated peptide.

28. The method of claim 5, wherein the subject has an iatrogenic ureteral injury.

29. The method of claim 5, wherein the subject has a ureteral injury arising from ligation, angulation, transection, laceration, crush, ischemia, or resection.

\* \* \* \* \*

SEQUENCE LISTING

```
Sequence total quantity: 749
SEQ ID NO: 1            moltype = AA  length = 17
FEATURE                 Location/Qualifiers
REGION                  1..17
                        note = HNP401
```

```
                           -continued source                  1..17
                        mol_type = protein
                        organism = synthetic construct
SEQUENCE: 1
SGQVPWEEPY YVVKKSS                                                   17

SEQ ID NO: 2            moltype = AA  length = 16
FEATURE                 Location/Qualifiers
REGION                  1..16
                        note = HNP402
source                  1..16
                        mol_type = protein
                        organism = synthetic construct
SEQUENCE: 2
WEYHYVDLNW TSQHPQ                                                    16

SEQ ID NO: 3            moltype = AA  length = 14
FEATURE                 Location/Qualifiers
REGION                  1..14
                        note = HNP403
source                  1..14
                        mol_type = protein
                        organism = synthetic construct
SEQUENCE: 3
DLPDIIWDFN WETA                                                      14

SEQ ID NO: 4            moltype = AA  length = 20
FEATURE                 Location/Qualifiers
REGION                  1..20
                        note = HNP401 with GGC linker
MOD_RES                 1
                        note = Ac
source                  1..20
                        mol_type = protein
                        organism = synthetic construct
SEQUENCE: 4
SGQVPWEEPY YVVKKSSGGC                                                20

SEQ ID NO: 5            moltype = AA  length = 19
FEATURE                 Location/Qualifiers
REGION                  1..19
                        note = HNP402 with GGC linker
MOD_RES                 1
                        note = Ac
source                  1..19
                        mol_type = protein
                        organism = synthetic construct
SEQUENCE: 5
WEYHYVDLNW TSQHPQGGC                                                 19

SEQ ID NO: 6            moltype = AA  length = 17
FEATURE                 Location/Qualifiers
REGION                  1..17
                        note = HNP403 with GGC linker
MOD_RES                 1
                        note = Ac
source                  1..17
                        mol_type = protein
                        organism = synthetic construct
SEQUENCE: 6
DLPDIIWDFN WETAGGC                                                   17

SEQ ID NO: 7            moltype = AA  length = 18
FEATURE                 Location/Qualifiers
REGION                  1..18
                        note = HNP401-N-2 with GGC linker
MOD_RES                 1
                        note = Ac
source                  1..18
                        mol_type = protein
                        organism = synthetic construct
SEQUENCE: 7
QVPWEEPYYV VKKSSGGC                                                  18

SEQ ID NO: 8            moltype = AA  length = 16
FEATURE                 Location/Qualifiers
REGION                  1..16
                        note = HNP401-N-4 with GGC linker
MOD_RES                 1
```

```
                          note = Ac
source                    1..16
                          mol_type = protein
                          organism = synthetic construct
SEQUENCE: 8
PWEEPYYVVK KSSGGC                                                    16

SEQ ID NO: 9              moltype = AA  length = 14
FEATURE                   Location/Qualifiers
REGION                    1..14
                          note = HNP401-N-6 with GGC linker
MOD_RES                   1
                          note = Ac
source                    1..14
                          mol_type = protein
                          organism = synthetic construct
SEQUENCE: 9
EEPYYVVKKS SGGC                                                      14

SEQ ID NO: 10             moltype = AA  length = 12
FEATURE                   Location/Qualifiers
REGION                    1..12
                          note = HNP401-N-8 with GGC linker
MOD_RES                   1
                          note = Ac
source                    1..12
                          mol_type = protein
                          organism = synthetic construct
SEQUENCE: 10
PYYVVKKSSG GC                                                        12

SEQ ID NO: 11             moltype = AA  length = 18
FEATURE                   Location/Qualifiers
REGION                    1..18
                          note = HNP401-C-2 with GGC linker
MOD_RES                   1
                          note = Ac
source                    1..18
                          mol_type = protein
                          organism = synthetic construct
SEQUENCE: 11
SGQVPWEEPY YVVKKGGC                                                  18

SEQ ID NO: 12             moltype = AA  length = 16
FEATURE                   Location/Qualifiers
REGION                    1..16
                          note = HNP401-C-4 with GGC linker
MOD_RES                   1
                          note = Ac
source                    1..16
                          mol_type = protein
                          organism = synthetic construct
SEQUENCE: 12
SGQVPWEEPY YVGGC                                                     16

SEQ ID NO: 13             moltype = AA  length = 14
FEATURE                   Location/Qualifiers
REGION                    1..14
                          note = HNP401-C-6 with GGC linker
MOD_RES                   1
                          note = Ac
source                    1..14
                          mol_type = protein
                          organism = synthetic construct
SEQUENCE: 13
SGQVPWEEPY YGGC                                                      14

SEQ ID NO: 14             moltype = AA  length = 12
FEATURE                   Location/Qualifiers
REGION                    1..12
                          note = HNP401-C-8 with GGC linker
MOD_RES                   1
                          note = Ac
source                    1..12
                          mol_type = protein
                          organism = synthetic construct
SEQUENCE: 14
SGQVPWEEPG GC                                                        12
```

```
SEQ ID NO: 15              moltype = AA   length = 4
FEATURE                    Location/Qualifiers
REGION                     1..4
                           note = linker
source                     1..4
                           mol_type = protein
                           organism = synthetic construct
SEQUENCE: 15
GGGC                                                                     4

SEQ ID NO: 16              moltype = AA   length = 16
FEATURE                    Location/Qualifiers
REGION                     1..16
                           note = HNP404
source                     1..16
                           mol_type = protein
                           organism = synthetic construct
SEQUENCE: 16
DTHAHAKPRV PAFKSV                                                       16

SEQ ID NO: 17              moltype = AA   length = 17
FEATURE                    Location/Qualifiers
REGION                     1..17
                           note = NP41
MOD_RES                    1
                           note = Ac
source                     1..17
                           mol_type = protein
                           organism = synthetic construct
SEQUENCE: 17
SHSNTQTLAK APEHTGC                                                      17

SEQ ID NO: 18              moltype = AA   length = 8
FEATURE                    Location/Qualifiers
REGION                     1..8
                           note = R3 Nidogen-2
source                     1..8
                           mol_type = protein
                           organism = synthetic construct
SEQUENCE: 18
KAIHPMRG                                                                 8

SEQ ID NO: 19              moltype = AA   length = 7
FEATURE                    Location/Qualifiers
REGION                     1..7
                           note = R3 Nidogen-2
source                     1..7
                           mol_type = protein
                           organism = synthetic construct
SEQUENCE: 19
GYWRNAL                                                                  7

SEQ ID NO: 20              moltype = AA   length = 15
FEATURE                    Location/Qualifiers
REGION                     1..15
                           note = HNP401-N-2
source                     1..15
                           mol_type = protein
                           organism = synthetic construct
SEQUENCE: 20
QVPWEEPYYV VKKSS                                                        15

SEQ ID NO: 21              moltype = AA   length = 17
FEATURE                    Location/Qualifiers
REGION                     1..17
                           note = HNP401-N-2 with GG linker
source                     1..17
                           mol_type = protein
                           organism = synthetic construct
SEQUENCE: 21
QVPWEEPYYV VKKSSGG                                                      17

SEQ ID NO: 22              moltype = AA   length = 13
FEATURE                    Location/Qualifiers
REGION                     1..13
                           note = HNP401-N-4
source                     1..13
                           mol_type = protein
                           organism = synthetic construct
```

```
SEQUENCE: 22
PWEEPYYVVK KSS                                                                    13

SEQ ID NO: 23           moltype = AA  length = 11
FEATURE                 Location/Qualifiers
REGION                  1..11
                        note = HNP401-N-6
source                  1..11
                        mol_type = protein
                        organism = synthetic construct
SEQUENCE: 23
EEPYYVVKKS S                                                                      11

SEQ ID NO: 24           moltype = AA  length = 9
FEATURE                 Location/Qualifiers
REGION                  1..9
                        note = HNP401-N-8
source                  1..9
                        mol_type = protein
                        organism = synthetic construct
SEQUENCE: 24
PYYVVKKSS                                                                          9

SEQ ID NO: 25           moltype = AA  length = 15
FEATURE                 Location/Qualifiers
REGION                  1..15
                        note = HNP401-C-2
source                  1..15
                        mol_type = protein
                        organism = synthetic construct
SEQUENCE: 25
SGQVPWEEPY YVVKK                                                                  15

SEQ ID NO: 26           moltype = AA  length = 13
FEATURE                 Location/Qualifiers
REGION                  1..13
                        note = HNP401-C-4
source                  1..13
                        mol_type = protein
                        organism = synthetic construct
SEQUENCE: 26
SGQVPWEEPY YVV                                                                    13

SEQ ID NO: 27           moltype = AA  length = 11
FEATURE                 Location/Qualifiers
REGION                  1..11
                        note = HNP401-C-6
source                  1..11
                        mol_type = protein
                        organism = synthetic construct
SEQUENCE: 27
SGQVPWEEPY Y                                                                      11

SEQ ID NO: 28           moltype = AA  length = 9
FEATURE                 Location/Qualifiers
REGION                  1..9
                        note = HNP401-C-8
source                  1..9
                        mol_type = protein
                        organism = synthetic construct
SEQUENCE: 28
SGQVPWEEP                                                                          9

SEQ ID NO: 29           moltype = AA  length = 10
FEATURE                 Location/Qualifiers
REGION                  1..10
                        note = R3 Nidogen-2
source                  1..10
                        mol_type = protein
                        organism = synthetic construct
SEQUENCE: 29
ACTVHKWDNC                                                                        10

SEQ ID NO: 30           moltype = AA  length = 10
FEATURE                 Location/Qualifiers
REGION                  1..10
                        note = R3 Nidogen-2
source                  1..10
                        mol_type = protein
```

-continued

```
                        organism = synthetic construct
SEQUENCE: 30
ACEPRSLANC                                                                      10

SEQ ID NO: 31           moltype = AA  length = 10
FEATURE                 Location/Qualifiers
REGION                  1..10
                        note = R3 Nidogen-2
source                  1..10
                        mol_type = protein
                        organism = synthetic construct
SEQUENCE: 31
ACPENKSKHC                                                                      10

SEQ ID NO: 32           moltype = AA  length = 10
FEATURE                 Location/Qualifiers
REGION                  1..10
                        note = R3 Nidogen-2
source                  1..10
                        mol_type = protein
                        organism = synthetic construct
SEQUENCE: 32
ACGEGEADVC                                                                      10

SEQ ID NO: 33           moltype = AA  length = 7
FEATURE                 Location/Qualifiers
REGION                  1..7
                        note = R3 Myelin PLP
source                  1..7
                        mol_type = protein
                        organism = synthetic construct
SEQUENCE: 33
EKPSWTR                                                                         7

SEQ ID NO: 34           moltype = AA  length = 7
FEATURE                 Location/Qualifiers
REGION                  1..7
                        note = R3 Myelin PLP
source                  1..7
                        mol_type = protein
                        organism = synthetic construct
SEQUENCE: 34
DTSRTME                                                                         7

SEQ ID NO: 35           moltype = AA  length = 7
FEATURE                 Location/Qualifiers
REGION                  1..7
                        note = R3 Myelin PLP
source                  1..7
                        mol_type = protein
                        organism = synthetic construct
SEQUENCE: 35
SMWSQFR                                                                         7

SEQ ID NO: 36           moltype = AA  length = 7
FEATURE                 Location/Qualifiers
REGION                  1..7
                        note = R3 Myelin PLP
source                  1..7
                        mol_type = protein
                        organism = synthetic construct
SEQUENCE: 36
NPNWRTI                                                                         7

SEQ ID NO: 37           moltype = AA  length = 7
FEATURE                 Location/Qualifiers
REGION                  1..7
                        note = R3 Myelin PLP
source                  1..7
                        mol_type = protein
                        organism = synthetic construct
SEQUENCE: 37
FKMPIPT                                                                         7

SEQ ID NO: 38           moltype = AA  length = 7
FEATURE                 Location/Qualifiers
REGION                  1..7
                        note = R3 Myelin PLP
source                  1..7
```

```
SEQUENCE: 38
YPKLWTY                                                                       7

SEQ ID NO: 39           moltype = AA   length = 7
FEATURE                 Location/Qualifiers
REGION                  1..7
                        note = R3 Myelin PLP
source                  1..7
                        mol_type = protein
                        organism = synthetic construct
SEQUENCE: 39
NPSHHPR                                                                       7

SEQ ID NO: 40           moltype = AA   length = 7
FEATURE                 Location/Qualifiers
REGION                  1..7
                        note = core binding domain
source                  1..7
                        mol_type = protein
                        organism = synthetic construct
SEQUENCE: 40
PYYVVKK                                                                       7

SEQ ID NO: 41           moltype = AA   length = 6
FEATURE                 Location/Qualifiers
REGION                  1..6
                        note = N-terminal sequence
source                  1..6
                        mol_type = protein
                        organism = synthetic construct
SEQUENCE: 41
QVPWEE                                                                        6

SEQ ID NO: 42           moltype = AA   length = 7
FEATURE                 Location/Qualifiers
REGION                  1..7
                        note = R3 Myelin PLP
source                  1..7
                        mol_type = protein
                        organism = synthetic construct
SEQUENCE: 42
LTHHFAP                                                                       7

SEQ ID NO: 43           moltype = AA   length = 7
FEATURE                 Location/Qualifiers
REGION                  1..7
                        note = R3 Myelin PLP
source                  1..7
                        mol_type = protein
                        organism = synthetic construct
SEQUENCE: 43
RHNVEFS                                                                       7

SEQ ID NO: 44           moltype = AA   length = 7
FEATURE                 Location/Qualifiers
REGION                  1..7
                        note = R3 Myelin PLP
source                  1..7
                        mol_type = protein
                        organism = synthetic construct
SEQUENCE: 44
FPVVTRN                                                                       7

SEQ ID NO: 45           moltype = AA   length = 7
FEATURE                 Location/Qualifiers
REGION                  1..7
                        note = R3 Myelin PLP
source                  1..7
                        mol_type = protein
                        organism = synthetic construct
SEQUENCE: 45
LRFQIPP                                                                       7

SEQ ID NO: 46           moltype = AA   length = 7
FEATURE                 Location/Qualifiers
REGION                  1..7
                        note = R3 Myelin PLP
```

```
source                      1..7
                            mol_type = protein
                            organism = synthetic construct
SEQUENCE: 46
LALYARM                                                                  7

SEQ ID NO: 47               moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 47
GPFLFTV                                                                  7

SEQ ID NO: 48               moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 48
YTPMGTG                                                                  7

SEQ ID NO: 49               moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 49
RFELPAP                                                                  7

SEQ ID NO: 50               moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 50
HQGSRTY                                                                  7

SEQ ID NO: 51               moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 51
TNPWKPH                                                                  7

SEQ ID NO: 52               moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 52
MTPHTSC                                                                  7

SEQ ID NO: 53               moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 53
GLIRHYT                                                                  7

SEQ ID NO: 54               moltype = AA  length = 7
FEATURE                     Location/Qualifiers
REGION                      1..7
```

```
                           note = R3 Myelin PLP
source                     1..7
                           mol_type = protein
                           organism = synthetic construct
SEQUENCE: 54
ATLKPYR                                                                 7

SEQ ID NO: 55              moltype = AA   length = 7
FEATURE                    Location/Qualifiers
REGION                     1..7
                           note = R3 Myelin Basic Protein
source                     1..7
                           mol_type = protein
                           organism = synthetic construct
SEQUENCE: 55
HRLPWHH                                                                 7

SEQ ID NO: 56              moltype = AA   length = 7
FEATURE                    Location/Qualifiers
REGION                     1..7
                           note = R3 Myelin Basic Protein
source                     1..7
                           mol_type = protein
                           organism = synthetic construct
SEQUENCE: 56
DGKNTSN                                                                 7

SEQ ID NO: 57              moltype = AA   length = 7
FEATURE                    Location/Qualifiers
REGION                     1..7
                           note = R3 Myelin Basic Protein
source                     1..7
                           mol_type = protein
                           organism = synthetic construct
SEQUENCE: 57
AGFPPNT                                                                 7

SEQ ID NO: 58              moltype = AA   length = 7
FEATURE                    Location/Qualifiers
REGION                     1..7
                           note = R3 Myelin Basic Protein
source                     1..7
                           mol_type = protein
                           organism = synthetic construct
SEQUENCE: 58
QNTGLKW                                                                 7

SEQ ID NO: 59              moltype = AA   length = 7
FEATURE                    Location/Qualifiers
REGION                     1..7
                           note = R3 Myelin Basic Protein
source                     1..7
                           mol_type = protein
                           organism = synthetic construct
SEQUENCE: 59
QIGVLPS                                                                 7

SEQ ID NO: 60              moltype = AA   length = 7
FEATURE                    Location/Qualifiers
REGION                     1..7
                           note = R3 Myelin Basic Protein
source                     1..7
                           mol_type = protein
                           organism = synthetic construct
SEQUENCE: 60
DPWVMLR                                                                 7

SEQ ID NO: 61              moltype = AA   length = 7
FEATURE                    Location/Qualifiers
REGION                     1..7
                           note = R3 Myelin Basic Protein
source                     1..7
                           mol_type = protein
                           organism = synthetic construct
SEQUENCE: 61
SPDRTSL                                                                 7

SEQ ID NO: 62              moltype = AA   length = 7
FEATURE                    Location/Qualifiers
```

| | | |
|---|---|---|
| REGION | 1..7 | |
| | note = R3 Myelin Basic Protein | |
| source | 1..7 | |
| | mol_type = protein | |
| | organism = synthetic construct | |
| SEQUENCE: 62 | | |
| MQTQGRV | | 7 |
| | | |
| SEQ ID NO: 63 | moltype = AA  length = 7 | |
| FEATURE | Location/Qualifiers | |
| REGION | 1..7 | |
| | note = R3 Myelin Basic Protein | |
| source | 1..7 | |
| | mol_type = protein | |
| | organism = synthetic construct | |
| SEQUENCE: 63 | | |
| LRPISHE | | 7 |
| | | |
| SEQ ID NO: 64 | moltype = AA  length = 7 | |
| FEATURE | Location/Qualifiers | |
| REGION | 1..7 | |
| | note = R3 Myelin Basic Protein | |
| source | 1..7 | |
| | mol_type = protein | |
| | organism = synthetic construct | |
| SEQUENCE: 64 | | |
| AWSTSSV | | 7 |
| | | |
| SEQ ID NO: 65 | moltype = AA  length = 10 | |
| FEATURE | Location/Qualifiers | |
| REGION | 1..10 | |
| | note = R3 Myelin Basic Protein | |
| source | 1..10 | |
| | mol_type = protein | |
| | organism = synthetic construct | |
| SEQUENCE: 65 | | |
| AGQLMRCANC | | 10 |
| | | |
| SEQ ID NO: 66 | moltype = AA  length = 7 | |
| FEATURE | Location/Qualifiers | |
| REGION | 1..7 | |
| | note = R3 Myelin Basic Protein | |
| source | 1..7 | |
| | mol_type = protein | |
| | organism = synthetic construct | |
| SEQUENCE: 66 | | |
| WTMKPNY | | 7 |
| | | |
| SEQ ID NO: 67 | moltype = AA  length = 7 | |
| FEATURE | Location/Qualifiers | |
| REGION | 1..7 | |
| | note = R3 Myelin Basic Protein | |
| source | 1..7 | |
| | mol_type = protein | |
| | organism = synthetic construct | |
| SEQUENCE: 67 | | |
| ILLPSLN | | 7 |
| | | |
| SEQ ID NO: 68 | moltype = AA  length = 7 | |
| FEATURE | Location/Qualifiers | |
| REGION | 1..7 | |
| | note = R3 Myelin Basic Protein | |
| source | 1..7 | |
| | mol_type = protein | |
| | organism = synthetic construct | |
| SEQUENCE: 68 | | |
| SKSDAWR | | 7 |
| | | |
| SEQ ID NO: 69 | moltype = AA  length = 7 | |
| FEATURE | Location/Qualifiers | |
| REGION | 1..7 | |
| | note = R3 Myelin Basic Protein | |
| source | 1..7 | |
| | mol_type = protein | |
| | organism = synthetic construct | |
| SEQUENCE: 69 | | |
| AITSRNA | | 7 |
| | | |
| SEQ ID NO: 70 | moltype = AA  length = 7 | |

```
FEATURE              Location/Qualifiers
REGION               1..7
                     note = R3 Myelin Basic Protein
source               1..7
                     mol_type = protein
                     organism = synthetic construct
SEQUENCE: 70
SVLRMLN                                                                      7

SEQ ID NO: 71        moltype = AA  length = 7
FEATURE              Location/Qualifiers
REGION               1..7
                     note = R3 Myelin Basic Protein
source               1..7
                     mol_type = protein
                     organism = synthetic construct
SEQUENCE: 71
LPMRILT                                                                      7

SEQ ID NO: 72        moltype = AA  length = 7
FEATURE              Location/Qualifiers
REGION               1..7
                     note = R3 Myelin Basic Protein
source               1..7
                     mol_type = protein
                     organism = synthetic construct
SEQUENCE: 72
EHGYYKV                                                                      7

SEQ ID NO: 73        moltype = AA  length = 7
FEATURE              Location/Qualifiers
REGION               1..7
                     note = R3 Myelin Basic Protein
source               1..7
                     mol_type = protein
                     organism = synthetic construct
SEQUENCE: 73
HPSTWHK                                                                      7

SEQ ID NO: 74        moltype = AA  length = 7
FEATURE              Location/Qualifiers
REGION               1..7
                     note = R3 Myelin Basic Protein
source               1..7
                     mol_type = protein
                     organism = synthetic construct
SEQUENCE: 74
NDTKTPS                                                                      7

SEQ ID NO: 75        moltype = AA  length = 12
FEATURE              Location/Qualifiers
REGION               1..12
                     note = R3 Human MPZ
source               1..12
                     mol_type = protein
                     organism = synthetic construct
SEQUENCE: 75
GDERIVRTLS HN                                                               12

SEQ ID NO: 76        moltype = AA  length = 7
FEATURE              Location/Qualifiers
REGION               1..7
                     note = R3 Human MPZ
source               1..7
                     mol_type = protein
                     organism = synthetic construct
SEQUENCE: 76
GLTPKLF                                                                      7

SEQ ID NO: 77        moltype = AA  length = 7
FEATURE              Location/Qualifiers
REGION               1..7
                     note = R3 Human MPZ
source               1..7
                     mol_type = protein
                     organism = synthetic construct
SEQUENCE: 77
RVPHSRT                                                                      7
```

```
SEQ ID NO: 78            moltype = AA   length = 7
FEATURE                  Location/Qualifiers
REGION                   1..7
                         note = R3 Human MPZ
source                   1..7
                         mol_type = protein
                         organism = synthetic construct
SEQUENCE: 78
TESLFPH                                                                    7

SEQ ID NO: 79            moltype = AA   length = 7
FEATURE                  Location/Qualifiers
REGION                   1..7
                         note = R3 Human MPZ
source                   1..7
                         mol_type = protein
                         organism = synthetic construct
SEQUENCE: 79
GPLRMAT                                                                    7

SEQ ID NO: 80            moltype = AA   length = 7
FEATURE                  Location/Qualifiers
REGION                   1..7
                         note = R3 Human MPZ
source                   1..7
                         mol_type = protein
                         organism = synthetic construct
SEQUENCE: 80
DRNSVFW                                                                    7

SEQ ID NO: 81            moltype = AA   length = 7
FEATURE                  Location/Qualifiers
REGION                   1..7
                         note = R3 Human MPZ
source                   1..7
                         mol_type = protein
                         organism = synthetic construct
SEQUENCE: 81
SAHAKHH                                                                    7

SEQ ID NO: 82            moltype = AA   length = 7
FEATURE                  Location/Qualifiers
REGION                   1..7
                         note = R3 Human MPZ
source                   1..7
                         mol_type = protein
                         organism = synthetic construct
SEQUENCE: 82
KMAGHTV                                                                    7

SEQ ID NO: 83            moltype = AA   length = 5
FEATURE                  Location/Qualifiers
REGION                   1..5
                         note = core binding domain
source                   1..5
                         mol_type = protein
                         organism = synthetic construct
SEQUENCE: 83
PYYVV                                                                      5

SEQ ID NO: 84            moltype = AA   length = 7
FEATURE                  Location/Qualifiers
REGION                   1..7
                         note = R3 Human MPZ
source                   1..7
                         mol_type = protein
                         organism = synthetic construct
SEQUENCE: 84
TMASPAK                                                                    7

SEQ ID NO: 85            moltype = AA   length = 7
FEATURE                  Location/Qualifiers
REGION                   1..7
                         note = R3 Human MPZ
source                   1..7
                         mol_type = protein
                         organism = synthetic construct
SEQUENCE: 85
VLTKPMP                                                                    7
```

```
SEQ ID NO: 86          moltype = AA   length = 7
FEATURE                Location/Qualifiers
REGION                 1..7
                       note = R3 Human MPZ
source                 1..7
                       mol_type = protein
                       organism = synthetic construct SEQUENCE: 86
LSSPLSL                                                                    7

SEQ ID NO: 87          moltype = AA   length = 7
FEATURE                Location/Qualifiers
REGION                 1..7
                       note = R3 Human MPZ
source                 1..7
                       mol_type = protein
                       organism = synthetic construct SEQUENCE: 87
WPSISRP                                                                    7

SEQ ID NO: 88          moltype = AA   length = 7
FEATURE                Location/Qualifiers
REGION                 1..7
                       note = R3 Human MPZ
source                 1..7
                       mol_type = protein
                       organism = synthetic construct SEQUENCE: 88
SHSPGNK                                                                    7

SEQ ID NO: 89          moltype = AA   length = 7
FEATURE                Location/Qualifiers
REGION                 1..7
                       note = R3 Human MPZ
source                 1..7
                       mol_type = protein
                       organism = synthetic construct SEQUENCE: 89
ETTRNYG                                                                    7

SEQ ID NO: 90          moltype = AA   length = 7
FEATURE                Location/Qualifiers
REGION                 1..7
                       note = R3 Human MPZ
source                 1..7
                       mol_type = protein
                       organism = synthetic construct SEQUENCE: 90
IKPPYTH                                                                    7

SEQ ID NO: 91          moltype = AA   length = 7
FEATURE                Location/Qualifiers
REGION                 1..7
                       note = R3 Human MPZ
source                 1..7
                       mol_type = protein
                       organism = synthetic construct SEQUENCE: 91
VLKNNPT                                                                    7

SEQ ID NO: 92          moltype = AA   length = 7
FEATURE                Location/Qualifiers
REGION                 1..7
                       note = R3 Human MPZ
source                 1..7
                       mol_type = protein
                       organism = synthetic construct SEQUENCE: 92
DPITRLK                                                                    7

SEQ ID NO: 93          moltype = AA   length = 7
FEATURE                Location/Qualifiers
REGION                 1..7
                       note = R3 Human MPZ
source                 1..7
                       mol_type = protein
                       organism = synthetic construct

SEQUENCE: 93
```

```
SHLASRP                                                               7

SEQ ID NO: 94           moltype = AA  length = 7
FEATURE                 Location/Qualifiers
REGION                  1..7
                        note = R3 Human MPZ
source                  1..7
                        mol_type = protein
                        organism = synthetic construct
SEQUENCE: 94
TSPWELR                                                               7

SEQ ID NO: 95           moltype = AA  length = 7
FEATURE                 Location/Qualifiers
REGION                  1..7
                        note = R3 Human MPZ
source                  1..7
                        mol_type = protein
                        organism = synthetic construct
SEQUENCE: 95
ALPLSAS                                                               7

SEQ ID NO: 96           moltype = AA  length = 11
FEATURE                 Location/Qualifiers
REGION                  1..11
                        note = HNP401-C-8 (with GG linker)
source                  1..11
                        mol_type = protein
                        organism = synthetic construct
SEQUENCE: 96
SGQVPWEEPG G                                                         11

SEQ ID NO: 97           moltype = AA  length = 13
FEATURE                 Location/Qualifiers
REGION                  1..13
                        note = HNP401-C-6 (with GG linker)
source                  1..13
                        mol_type = protein
                        organism = synthetic construct
SEQUENCE: 97
SGQVPWEEPY YGG                                                       13

SEQ ID NO: 98           moltype = AA  length = 15
FEATURE                 Location/Qualifiers
REGION                  1..15
                        note = HNP401-C-4 (with GG linker)
source                  1..15
                        mol_type = protein
                        organism = synthetic construct
SEQUENCE: 98
SGQVPWEEPY YVVGG                                                     15

SEQ ID NO: 99           moltype = AA  length = 17
FEATURE                 Location/Qualifiers
REGION                  1..17
                        note = HNP401-C-2 (with GG linker)
source                  1..17
                        mol_type = protein
                        organism = synthetic construct
SEQUENCE: 99
SGQVPWEEPY YVVKKGG                                                   17

SEQ ID NO: 100          moltype = AA  length = 11
FEATURE                 Location/Qualifiers
REGION                  1..11
                        note = HNP401-N-8 (with GG linker)
source                  1..11
                        mol_type = protein
                        organism = synthetic construct
SEQUENCE: 100
PYYVVKKSSG G                                                         11

SEQ ID NO: 101          moltype = AA  length = 13
FEATURE                 Location/Qualifiers
REGION                  1..13
                        note = HNP401-N-6 (with GG linker)
source                  1..13
                        mol_type = protein
                        organism = synthetic construct
```

```
SEQUENCE: 101
EEPYVVVKKS SGG                                                                    13

SEQ ID NO: 102          moltype = AA   length = 15
FEATURE                 Location/Qualifiers
REGION                  1..15
                        note = HNP401-N-4 (with GG linker)
source                  1..15
                        mol_type = protein
                        organism = synthetic construct
SEQUENCE: 102
PWEEPYYVVK KSSGG                                                                  15

SEQ ID NO: 103          moltype = AA   length = 9
FEATURE                 Location/Qualifiers
REGION                  1..9
                        note = R3 Human MPZ
source                  1..9
                        mol_type = protein
                        organism = synthetic construct
SEQUENCE: 103
CLKQQTGDC                                                                          9

SEQ ID NO: 104          moltype = AA   length = 12
FEATURE                 Location/Qualifiers
REGION                  1..12
                        note = R3 Human MPZ
source                  1..12
                        mol_type = protein
                        organism = synthetic construct
SEQUENCE: 104
EGHVWSEYTW GT                                                                     12

SEQ ID NO: 105          moltype = AA   length = 7
FEATURE                 Location/Qualifiers
REGION                  1..7
                        note = R3 Human MPZ
source                  1..7
                        mol_type = protein
                        organism = synthetic construct
SEQUENCE: 105
FMSDVDH                                                                            7

SEQ ID NO: 106          moltype = AA   length = 7
FEATURE                 Location/Qualifiers
REGION                  1..7
                        note = R3 Human MPZ
source                  1..7
                        mol_type = protein
                        organism = synthetic construct
SEQUENCE: 106
ISSVTVV                                                                            7

SEQ ID NO: 107          moltype = AA   length = 7
FEATURE                 Location/Qualifiers
REGION                  1..7
                        note = R3 Human MPZ
source                  1..7
                        mol_type = protein
                        organism = synthetic construct
SEQUENCE: 107
KQPAMFN                                                                            7

SEQ ID NO: 108          moltype = AA   length = 7
FEATURE                 Location/Qualifiers
REGION                  1..7
                        note = R3 Human MPZ
source                  1..7
                        mol_type = protein
                        organism = synthetic construct
SEQUENCE: 108
LISPTAR                                                                            7

SEQ ID NO: 109          moltype = AA   length = 7
FEATURE                 Location/Qualifiers
REGION                  1..7
                        note = R3 Human MPZ
source                  1..7
                        mol_type = protein
```

```
SEQUENCE: 109
LVLQTTP                                                              7

SEQ ID NO: 110         moltype = AA   length = 7
FEATURE                Location/Qualifiers
REGION                 1..7
                       note = R3 Human MPZ
source                 1..7
                       mol_type = protein
                       organism = synthetic construct
SEQUENCE: 110
NPTSEGA                                                              7

SEQ ID NO: 111         moltype = AA   length = 7
FEATURE                Location/Qualifiers
REGION                 1..7
                       note = R3 Human MPZ
source                 1..7
                       mol_type = protein
                       organism = synthetic construct
SEQUENCE: 111
THSTDLS                                                              7

SEQ ID NO: 112         moltype = AA   length = 12
FEATURE                Location/Qualifiers
REGION                 1..12
                       note = R3 Human MPZ
source                 1..12
                       mol_type = protein
                       organism = synthetic construct
SEQUENCE: 112
TTNVTEIERE SY                                                       12

SEQ ID NO: 113         moltype = AA   length = 7
FEATURE                Location/Qualifiers
REGION                 1..7
                       note = R3 Human MPZ
source                 1..7
                       mol_type = protein
                       organism = synthetic construct
SEQUENCE: 113
YAPWRVF                                                              7

SEQ ID NO: 114         moltype = AA   length = 7
FEATURE                Location/Qualifiers
REGION                 1..7
                       note = R3 Human MPZ
source                 1..7
                       mol_type = protein
                       organism = synthetic construct
SEQUENCE: 114
YGQSITE                                                              7

SEQ ID NO: 115         moltype = AA   length = 9
FEATURE                Location/Qualifiers
REGION                 1..9
                       note = R3 Human MPZ
source                 1..9
                       mol_type = protein
                       organism = synthetic construct
SEQUENCE: 115
CDIKDANSC                                                            9

SEQ ID NO: 116         moltype = AA   length = 9
FEATURE                Location/Qualifiers
REGION                 1..9
                       note = R3 Human MPZ
source                 1..9
                       mol_type = protein
                       organism = synthetic construct
SEQUENCE: 116
CIKGEDNQC                                                            9

SEQ ID NO: 117         moltype = AA   length = 7
FEATURE                Location/Qualifiers
REGION                 1..7
                       note = R3 Human MPZ
source                 1..7
```

-continued

```
                        mol_type = protein
                        organism = synthetic construct
SEQUENCE: 117
HNQLLYT                                                                 7

SEQ ID NO: 118          moltype = AA   length = 7
FEATURE                 Location/Qualifiers
REGION                  1..7
                        note = R3 Human MPZ
source                  1..7
                        mol_type = protein
                        organism = synthetic construct
SEQUENCE: 118
IEQVGWR                                                                 7

SEQ ID NO: 119          moltype = AA   length = 7
FEATURE                 Location/Qualifiers
REGION                  1..7
                        note = R3 Human MPZ
source                  1..7
                        mol_type = protein
                        organism = synthetic construct
SEQUENCE: 119
KTPILAS                                                                 7

SEQ ID NO: 120          moltype = AA   length = 7
FEATURE                 Location/Qualifiers
REGION                  1..7
                        note = R3 Human MPZ
source                  1..7
                        mol_type = protein
                        organism = synthetic construct
SEQUENCE: 120
LWAKRDA                                                                 7

SEQ ID NO: 121          moltype = AA   length = 7
FEATURE                 Location/Qualifiers
REGION                  1..7
                        note = R3 Human MPZ
source                  1..7
                        mol_type = protein
                        organism = synthetic construct
SEQUENCE: 121
NPISPRN                                                                 7

SEQ ID NO: 122          moltype = AA   length = 7
FEATURE                 Location/Qualifiers
REGION                  1..7
                        note = R3 Human MPZ
source                  1..7
                        mol_type = protein
                        organism = synthetic construct
SEQUENCE: 122
NTASMTT                                                                 7

SEQ ID NO: 123          moltype = AA   length = 7
FEATURE                 Location/Qualifiers
REGION                  1..7
                        note = R3 Human MPZ
source                  1..7
                        mol_type = protein
                        organism = synthetic construct
SEQUENCE: 123
SAHSVVE                                                                 7

SEQ ID NO: 124          moltype = AA   length = 7
FEATURE                 Location/Qualifiers
REGION                  1..7
                        note = R3 Human MPZ
source                  1..7
                        mol_type = protein
                        organism = synthetic construct
SEQUENCE: 124
YSSLTSN                                                                 7

SEQ ID NO: 125          moltype = AA   length = 7
FEATURE                 Location/Qualifiers
REGION                  1..7
                        note = R3 Human MPZ
```

```
source                          1..7
                                mol_type = protein
                                organism = synthetic construct
SEQUENCE: 125
AWTMRAS                                                                 7

SEQ ID NO: 126                  moltype = AA  length = 9
FEATURE                         Location/Qualifiers
REGION                          1..9
                                note = R3 Human MPZ
source                          1..9
                                mol_type = protein
                                organism = synthetic construct
SEQUENCE: 126
CERIGPREC                                                               9

SEQ ID NO: 127                  moltype = AA  length = 9
FEATURE                         Location/Qualifiers
REGION                          1..9
                                note = R3 Human MPZ
source                          1..9
                                mol_type = protein
                                organism = synthetic construct
SEQUENCE: 127
CQKWFTFAC                                                               9

SEQ ID NO: 128                  moltype = AA  length = 9
FEATURE                         Location/Qualifiers
REGION                          1..9
                                note = R3 Human MPZ
source                          1..9
                                mol_type = protein
                                organism = synthetic construct
SEQUENCE: 128
CSNALNKAC                                                               9

SEQ ID NO: 129                  moltype = AA  length = 7
FEATURE                         Location/Qualifiers
REGION                          1..7
                                note = R3 Human MPZ
source                          1..7
                                mol_type = protein
                                organism = synthetic construct
SEQUENCE: 129
FSPRDVS                                                                 7

SEQ ID NO: 130                  moltype = AA  length = 7
FEATURE                         Location/Qualifiers
REGION                          1..7
                                note = R3 Human MPZ
source                          1..7
                                mol_type = protein
                                organism = synthetic construct
SEQUENCE: 130
FSTTGRG                                                                 7

SEQ ID NO: 131                  moltype = AA  length = 7
FEATURE                         Location/Qualifiers
REGION                          1..7
                                note = R3 Human MPZ
source                          1..7
                                mol_type = protein
                                organism = synthetic construct
SEQUENCE: 131
HHPLFID                                                                 7

SEQ ID NO: 132                  moltype = AA  length = 7
FEATURE                         Location/Qualifiers
REGION                          1..7
                                note = R3 Human MPZ
source                          1..7
                                mol_type = protein
                                organism = synthetic construct
SEQUENCE: 132
LVNPFPE                                                                 7

SEQ ID NO: 133                  moltype = AA  length = 7
FEATURE                         Location/Qualifiers
REGION                          1..7
```

```
                              note = R3 Human MPZ
source                        1..7
                              mol_type = protein
                              organism = synthetic construct
SEQUENCE: 133
YEGERGA                                                                   7

SEQ ID NO: 134                moltype = AA   length = 9
FEATURE                       Location/Qualifiers
REGION                        1..9
                              note = R3 Human MPZ
source                        1..9
                              mol_type = protein
                              organism = synthetic construct
SEQUENCE: 134
CEDRQRSMC                                                                 9

SEQ ID NO: 135                moltype = AA   length = 9
FEATURE                       Location/Qualifiers
REGION                        1..9
                              note = R3 Human MPZ
source                        1..9
                              mol_type = protein
                              organism = synthetic construct
SEQUENCE: 135
CGEKIMSLC                                                                 9

SEQ ID NO: 136                moltype = AA   length = 7
FEATURE                       Location/Qualifiers
REGION                        1..7
                              note = R3 Human MPZ
source                        1..7
                              mol_type = protein
                              organism = synthetic construct
SEQUENCE: 136
DRYLLNQ                                                                   7

SEQ ID NO: 137                moltype = AA   length = 7
FEATURE                       Location/Qualifiers
REGION                        1..7
                              note = R3 Human MPZ
source                        1..7
                              mol_type = protein
                              organism = synthetic construct
SEQUENCE: 137
FPSYTIS                                                                   7

SEQ ID NO: 138                moltype = AA   length = 7
FEATURE                       Location/Qualifiers
REGION                        1..7
                              note = R3 Human MPZ
source                        1..7
                              mol_type = protein
                              organism = synthetic construct
SEQUENCE: 138
GGSKVWG                                                                   7

SEQ ID NO: 139                moltype = AA   length = 7
FEATURE                       Location/Qualifiers
REGION                        1..7
                              note = R3 Human MPZ
source                        1..7
                              mol_type = protein
                              organism = synthetic construct
SEQUENCE: 139
GLWRHTM                                                                   7

SEQ ID NO: 140                moltype = AA   length = 7
FEATURE                       Location/Qualifiers
REGION                        1..7
                              note = R3 Human MPZ
source                        1..7
                              mol_type = protein
                              organism = synthetic construct
SEQUENCE: 140
KRNLWDI                                                                   7

SEQ ID NO: 141                moltype = AA   length = 7
FEATURE                       Location/Qualifiers
```

```
REGION                  1..7
                        note = R3 Human MPZ
source                  1..7
                        mol_type = protein
                        organism = synthetic construct
SEQUENCE: 141
SPNTNSH                                                                    7

SEQ ID NO: 142          moltype = AA  length = 7
FEATURE                 Location/Qualifiers
REGION                  1..7
                        note = R3 Human MPZ
source                  1..7
                        mol_type = protein
                        organism = synthetic construct
SEQUENCE: 142
TLLHYSA                                                                    7

SEQ ID NO: 143          moltype = AA  length = 7
FEATURE                 Location/Qualifiers
REGION                  1..7
                        note = R3 Human MPZ
source                  1..7
                        mol_type = protein
                        organism = synthetic construct
SEQUENCE: 143
VPLAYLR                                                                    7

SEQ ID NO: 144          moltype = AA  length = 7
FEATURE                 Location/Qualifiers
REGION                  1..7
                        note = R3 Human MPZ
source                  1..7
                        mol_type = protein
                        organism = synthetic construct
SEQUENCE: 144
VVPLKWI                                                                    7

SEQ ID NO: 145          moltype = AA  length = 9
FEATURE                 Location/Qualifiers
REGION                  1..9
                        note = R3 Human MPZ
source                  1..9
                        mol_type = protein
                        organism = synthetic construct
SEQUENCE: 145
CRVGVTSAC                                                                  9

SEQ ID NO: 146          moltype = AA  length = 7
FEATURE                 Location/Qualifiers
REGION                  1..7
                        note = R3 Human MPZ
source                  1..7
                        mol_type = protein
                        organism = synthetic construct
SEQUENCE: 146
FALPAGL                                                                    7

SEQ ID NO: 147          moltype = AA  length = 7
FEATURE                 Location/Qualifiers
REGION                  1..7
                        note = R3 Human MPZ
source                  1..7
                        mol_type = protein
                        organism = synthetic construct
SEQUENCE: 147
FRVTQTA                                                                    7

SEQ ID NO: 148          moltype = AA  length = 7
FEATURE                 Location/Qualifiers
REGION                  1..7
                        note = R3 Human MPZ
source                  1..7
                        mol_type = protein
                        organism = synthetic construct
SEQUENCE: 148
HPLMVPS                                                                    7

SEQ ID NO: 149          moltype = AA  length = 7
```

```
                          -continued

FEATURE              Location/Qualifiers
REGION               1..7
                     note = R3 Human MPZ
source               1..7
                     mol_type = protein
                     organism = synthetic construct
SEQUENCE: 149
LPNANNL                                                              7

SEQ ID NO: 150       moltype = AA  length = 7
FEATURE              Location/Qualifiers
REGION               1..7
                     note = R3 Human MPZ
source               1..7
                     mol_type = protein
                     organism = synthetic construct
SEQUENCE: 150
MIHTRQT                                                              7

SEQ ID NO: 151       moltype = AA  length = 7
FEATURE              Location/Qualifiers
REGION               1..7
                     note = R3 Human MPZ
source               1..7
                     mol_type = protein
                     organism = synthetic construct
SEQUENCE: 151
SETESYM                                                              7

SEQ ID NO: 152       moltype = AA  length = 7
FEATURE              Location/Qualifiers
REGION               1..7
                     note = R3 Human MPZ
source               1..7
                     mol_type = protein
                     organism = synthetic construct
SEQUENCE: 152
SNALSYF                                                              7

SEQ ID NO: 153       moltype = AA  length = 7
FEATURE              Location/Qualifiers
REGION               1..7
                     note = R3 Human MPZ
source               1..7
                     mol_type = protein
                     organism = synthetic construct
SEQUENCE: 153
SYLPPFI                                                              7

SEQ ID NO: 154       moltype = AA  length = 7
FEATURE              Location/Qualifiers
REGION               1..7
                     note = R3 Human MPZ
source               1..7
                     mol_type = protein
                     organism = synthetic construct
SEQUENCE: 154
VHTPYRS                                                              7

SEQ ID NO: 155       moltype = AA  length = 7
FEATURE              Location/Qualifiers
REGION               1..7
                     note = R3 Human MPZ
source               1..7
                     mol_type = protein
                     organism = synthetic construct
SEQUENCE: 155
WPRPIQI                                                              7

SEQ ID NO: 156       moltype = AA  length = 7
FEATURE              Location/Qualifiers
REGION               1..7
                     note = R3 Human MPZ
source               1..7
                     mol_type = protein
                     organism = synthetic construct
SEQUENCE: 156
WTSVATA                                                              7
```

```
SEQ ID NO: 157            moltype = AA  length = 7
FEATURE                   Location/Qualifiers
REGION                    1..7
                          note = R3 Human MPZ
source                    1..7
                          mol_type = protein
                          organism = synthetic construct
SEQUENCE: 157
ALPISYL                                                                   7

SEQ ID NO: 158            moltype = AA  length = 7
FEATURE                   Location/Qualifiers
REGION                    1..7
                          note = R3 Human MPZ
source                    1..7
                          mol_type = protein
                          organism = synthetic construct
SEQUENCE: 158
FEHMAVT                                                                   7

SEQ ID NO: 159            moltype = AA  length = 7
FEATURE                   Location/Qualifiers
REGION                    1..7
                          note = R3 Human MPZ
source                    1..7
                          mol_type = protein
                          organism = synthetic construct
SEQUENCE: 159
NASVPPK                                                                   7

SEQ ID NO: 160            moltype = AA  length = 7
FEATURE                   Location/Qualifiers
REGION                    1..7
                          note = R3 Human MPZ
source                    1..7
                          mol_type = protein
                          organism = synthetic construct
SEQUENCE: 160
SGHGAFR                                                                   7

SEQ ID NO: 161            moltype = AA  length = 7
FEATURE                   Location/Qualifiers
REGION                    1..7
                          note = R3 Human MPZ
source                    1..7
                          mol_type = protein
                          organism = synthetic construct
SEQUENCE: 161
TTLVVTA                                                                   7

SEQ ID NO: 162            moltype = AA  length = 9
FEATURE                   Location/Qualifiers
REGION                    1..9
                          note = R3 Human MPZ
source                    1..9
                          mol_type = protein
                          organism = synthetic construct
SEQUENCE: 162
CPDAARNSC                                                                 9

SEQ ID NO: 163            moltype = AA  length = 9
FEATURE                   Location/Qualifiers
REGION                    1..9
                          note = R3 Human MPZ
source                    1..9
                          mol_type = protein
                          organism = synthetic construct
SEQUENCE: 163
CYSSVADMC                                                                 9

SEQ ID NO: 164            moltype = AA  length = 7
FEATURE                   Location/Qualifiers
REGION                    1..7
                          note = R3 Human MPZ
source                    1..7
                          mol_type = protein
                          organism = synthetic construct
SEQUENCE: 164
LSPPRIM                                                                   7
```

```
SEQ ID NO: 165        moltype = AA   length = 7
FEATURE               Location/Qualifiers
REGION                1..7
                      note = R3 Human MPZ
source                1..7
                      mol_type = protein
                      organism = synthetic construct
SEQUENCE: 165
WMTNLDP                                                                    7

SEQ ID NO: 166        moltype = AA   length = 7
FEATURE               Location/Qualifiers
REGION                1..7
                      note = R3 Human MPZ
source                1..7
                      mol_type = protein
                      organism = synthetic construct
SEQUENCE: 166
KLPTLSV                                                                    7

SEQ ID NO: 167        moltype = AA   length = 7
FEATURE               Location/Qualifiers
REGION                1..7
                      note = R3 Human MPZ
source                1..7
                      mol_type = protein
                      organism = synthetic construct
SEQUENCE: 167
AMSNLSY                                                                    7

SEQ ID NO: 168        moltype = AA   length = 7
FEATURE               Location/Qualifiers
REGION                1..7
                      note = R3 Human MPZ
source                1..7
                      mol_type = protein
                      organism = synthetic construct
SEQUENCE: 168
HPFPRFD                                                                    7

SEQ ID NO: 169        moltype = AA   length = 7
FEATURE               Location/Qualifiers
REGION                1..7
                      note = R3 Human MPZ
source                1..7
                      mol_type = protein
                      organism = synthetic construct
SEQUENCE: 169
LPAESHW                                                                    7

SEQ ID NO: 170        moltype = AA   length = 7
FEATURE               Location/Qualifiers
REGION                1..7
                      note = R3 Human MPZ
source                1..7
                      mol_type = protein
                      organism = synthetic construct
SEQUENCE: 170
STHEWRT                                                                    7

SEQ ID NO: 171        moltype = AA   length = 7
FEATURE               Location/Qualifiers
REGION                1..7
                      note = R3 Human MPZ
source                1..7
                      mol_type = protein
                      organism = synthetic construct
SEQUENCE: 171
TTWPNTA                                                                    7

SEQ ID NO: 172        moltype = AA   length = 7
FEATURE               Location/Qualifiers
REGION                1..7
                      note = R3 Human MPZ
source                1..7
                      mol_type = protein
                      organism = synthetic construct
SEQUENCE: 172
```

```
YMKHSPG                                                                           7

SEQ ID NO: 173           moltype = AA  length = 12
FEATURE                  Location/Qualifiers
REGION                   1..12
                         note = R3 Human MPZ
source                   1..12
                         mol_type = protein
                         organism = synthetic construct
SEQUENCE: 173
AYLEDWRSMS TR                                                                    12

SEQ ID NO: 174           moltype = AA  length = 7
FEATURE                  Location/Qualifiers
REGION                   1..7
                         note = R3 Human MPZ
source                   1..7
                         mol_type = protein
                         organism = synthetic construct
SEQUENCE: 174
GPVVSGM                                                                           7

SEQ ID NO: 175           moltype = AA  length = 7
FEATURE                  Location/Qualifiers
REGION                   1..7
                         note = R3 Human MPZ
source                   1..7
                         mol_type = protein
                         organism = synthetic construct
SEQUENCE: 175
HLDSRRH                                                                           7

SEQ ID NO: 176           moltype = AA  length = 7
FEATURE                  Location/Qualifiers
REGION                   1..7
                         note = R3 Human MPZ
source                   1..7
                         mol_type = protein
                         organism = synthetic construct
SEQUENCE: 176
LVLSNPR                                                                           7

SEQ ID NO: 177           moltype = AA  length = 7
FEATURE                  Location/Qualifiers
REGION                   1..7
                         note = R3 Human MPZ
source                   1..7
                         mol_type = protein
                         organism = synthetic construct
SEQUENCE: 177
NMSHSNR                                                                           7

SEQ ID NO: 178           moltype = AA  length = 7
FEATURE                  Location/Qualifiers
REGION                   1..7
                         note = R3 Human MPZ
source                   1..7
                         mol_type = protein
                         organism = synthetic construct
SEQUENCE: 178
SVAYVPV                                                                           7

SEQ ID NO: 179           moltype = AA  length = 7
FEATURE                  Location/Qualifiers
REGION                   1..7
                         note = R3 Human MPZ
source                   1..7
                         mol_type = protein
                         organism = synthetic construct
SEQUENCE: 179
YPQARTS                                                                           7

SEQ ID NO: 180           moltype = AA  length = 7
FEATURE                  Location/Qualifiers
REGION                   1..7
                         note = R3 Human MPZ
source                   1..7
                         mol_type = protein
                         organism = synthetic construct
```

```
SEQUENCE: 180
MYHDSVS                                                                          7

SEQ ID NO: 181          moltype = AA  length = 12
FEATURE                 Location/Qualifiers
REGION                  1..12
                        note = R3 Human MPZ
source                  1..12
                        mol_type = protein
                        organism = synthetic construct
SEQUENCE: 181
ADNVLRRALE NI                                                                   12

SEQ ID NO: 182          moltype = AA  length = 7
FEATURE                 Location/Qualifiers
REGION                  1..7
                        note = R3 Human MPZ
source                  1..7
                        mol_type = protein
                        organism = synthetic construct
SEQUENCE: 182
QIAHLEY                                                                          7

SEQ ID NO: 183          moltype = AA  length = 12
FEATURE                 Location/Qualifiers
REGION                  1..12
                        note = R3 Human MPZ
source                  1..12
                        mol_type = protein
                        organism = synthetic construct
SEQUENCE: 183
GMVSPHHSVY RH                                                                   12

SEQ ID NO: 184          moltype = AA  length = 7
FEATURE                 Location/Qualifiers
REGION                  1..7
                        note = R3 Human MPZ
source                  1..7
                        mol_type = protein
                        organism = synthetic construct
SEQUENCE: 184
GSWSSGF                                                                          7

SEQ ID NO: 185          moltype = AA  length = 12
FEATURE                 Location/Qualifiers
REGION                  1..12
                        note = R3 Human MPZ
source                  1..12
                        mol_type = protein
                        organism = synthetic construct
SEQUENCE: 185
NGAYSLAIRY TS                                                                   12

SEQ ID NO: 186          moltype = AA  length = 12
FEATURE                 Location/Qualifiers
REGION                  1..12
                        note = R3 Human MPZ
source                  1..12
                        mol_type = protein
                        organism = synthetic construct
SEQUENCE: 186
YTPNWHFRWM PA                                                                   12

SEQ ID NO: 187          moltype = AA  length = 12
FEATURE                 Location/Qualifiers
REGION                  1..12
                        note = R3 Human MPZ
source                  1..12
                        mol_type = protein
                        organism = synthetic construct
SEQUENCE: 187
GEWRARIDQD VS                                                                   12

SEQ ID NO: 188          moltype = AA  length = 7
FEATURE                 Location/Qualifiers
REGION                  1..7
                        note = R3 Myelin Basic Protein
source                  1..7
                        mol_type = protein
```

-continued

```
SEQUENCE: 188
AGSLLSL                                                                    7

SEQ ID NO: 189           moltype = AA   length = 7
FEATURE                  Location/Qualifiers
REGION                   1..7
                         note = R3 Myelin Basic Protein
source                   1..7
                         mol_type = protein
                         organism = synthetic construct
SEQUENCE: 189
AIPPRKL                                                                    7

SEQ ID NO: 190           moltype = AA   length = 7
FEATURE                  Location/Qualifiers
REGION                   1..7
                         note = R3 Myelin Basic Protein
source                   1..7
                         mol_type = protein
                         organism = synthetic construct
SEQUENCE: 190
AISWKGF                                                                    7

SEQ ID NO: 191           moltype = AA   length = 7
FEATURE                  Location/Qualifiers
REGION                   1..7
                         note = R3 Myelin Basic Protein
source                   1..7
                         mol_type = protein
                         organism = synthetic construct
SEQUENCE: 191
AKFTMWV                                                                    7

SEQ ID NO: 192           moltype = AA   length = 7
FEATURE                  Location/Qualifiers
REGION                   1..7
                         note = R3 Myelin Basic Protein
source                   1..7
                         mol_type = protein
                         organism = synthetic construct
SEQUENCE: 192
ALRDTRV                                                                    7

SEQ ID NO: 193           moltype = AA   length = 7
FEATURE                  Location/Qualifiers
REGION                   1..7
                         note = R3 Myelin Basic Protein
source                   1..7
                         mol_type = protein
                         organism = synthetic construct
SEQUENCE: 193
ALYNQMT                                                                    7

SEQ ID NO: 194           moltype = AA   length = 7
FEATURE                  Location/Qualifiers
REGION                   1..7
                         note = R3 Myelin Basic Protein
source                   1..7
                         mol_type = protein
                         organism = synthetic construct
SEQUENCE: 194
AQFLTIY                                                                    7

SEQ ID NO: 195           moltype = AA   length = 7
FEATURE                  Location/Qualifiers
REGION                   1..7
                         note = R3 Myelin Basic Protein
source                   1..7
                         mol_type = protein
                         organism = synthetic construct
SEQUENCE: 195
AQLGAFR                                                                    7

SEQ ID NO: 196           moltype = AA   length = 7
FEATURE                  Location/Qualifiers
REGION                   1..7
                         note = R3 Myelin Basic Protein
source                   1..7
```

```
                        mol_type = protein
                        organism = synthetic construct
SEQUENCE: 196
ARVPNPL                                                                    7

SEQ ID NO: 197          moltype = AA  length = 9
FEATURE                 Location/Qualifiers
REGION                  1..9
                        note = R3 Myelin Basic Protein
source                  1..9
                        mol_type = protein
                        organism = synthetic construct
SEQUENCE: 197
CTMTNQYDC                                                                  9

SEQ ID NO: 198          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 198
DSQEKSV                                                                    7

SEQ ID NO: 199          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 199
DVRIWTL                                                                    7

SEQ ID NO: 200          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 200
ELKSLRF                                                                    7

SEQ ID NO: 201          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 201
ESKSPRE                                                                    7

SEQ ID NO: 202          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 202
ETHYKIA                                                                    7

SEQ ID NO: 203          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 203
FDLLARK                                                                    7

SEQ ID NO: 204          moltype = AA  length = 7
FEATURE                 Location/Qualifiers
REGION                  1..7
                        note = R3 Myelin Basic Protein
```

```
source                   1..7
                         mol_type = protein
                         organism = synthetic construct
SEQUENCE: 204
FQLSYET                                                                  7

SEQ ID NO: 205           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 205
GEPALVT                                                                  7

SEQ ID NO: 206           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 206
GPRVTPH                                                                  7

SEQ ID NO: 207           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 207
GQWWKML                                                                  7

SEQ ID NO: 208           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 208
GRHTDVV                                                                  7

SEQ ID NO: 209           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 209
GSPYGWG                                                                  7

SEQ ID NO: 210           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 210
GVAEVGL                                                                  7

SEQ ID NO: 211           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 211
HAHWARL                                                                  7

SEQ ID NO: 212           moltype = AA  length = 7
FEATURE                  Location/Qualifiers
REGION                   1..7
```

```
SEQ ID NO: 212        moltype = AA   length = 7
FEATURE               Location/Qualifiers
REGION                1..7
                      note = R3 Myelin Basic Protein
source                1..7
                      mol_type = protein
                      organism = synthetic construct
SEQUENCE: 212
HFTFFPI                                                                    7

SEQ ID NO: 213        moltype = AA   length = 7
FEATURE               Location/Qualifiers
REGION                1..7
                      note = R3 Myelin Basic Protein
source                1..7
                      mol_type = protein
                      organism = synthetic construct
SEQUENCE: 213
HPWSHPN                                                                    7

SEQ ID NO: 214        moltype = AA   length = 7
FEATURE               Location/Qualifiers
REGION                1..7
                      note = R3 Myelin Basic Protein
source                1..7
                      mol_type = protein
                      organism = synthetic construct
SEQUENCE: 214
HQMRTML                                                                    7

SEQ ID NO: 215        moltype = AA   length = 7
FEATURE               Location/Qualifiers
REGION                1..7
                      note = R3 Myelin Basic Protein
source                1..7
                      mol_type = protein
                      organism = synthetic construct
SEQUENCE: 215
HQPLFPR                                                                    7

SEQ ID NO: 216        moltype = AA   length = 7
FEATURE               Location/Qualifiers
REGION                1..7
                      note = R3 Myelin Basic Protein
source                1..7
                      mol_type = protein
                      organism = synthetic construct
SEQUENCE: 216
HRTHLHQ                                                                    7

SEQ ID NO: 217        moltype = AA   length = 7
FEATURE               Location/Qualifiers
REGION                1..7
                      note = R3 Myelin Basic Protein
source                1..7
                      mol_type = protein
                      organism = synthetic construct
SEQUENCE: 217
HSGPLLP                                                                    7

SEQ ID NO: 218        moltype = AA   length = 7
FEATURE               Location/Qualifiers
REGION                1..7
                      note = R3 Myelin Basic Protein
source                1..7
                      mol_type = protein
                      organism = synthetic construct
SEQUENCE: 218
HSSATMS                                                                    7

SEQ ID NO: 219        moltype = AA   length = 7
FEATURE               Location/Qualifiers
REGION                1..7
                      note = R3 Myelin Basic Protein
source                1..7
                      mol_type = protein
                      organism = synthetic construct
SEQUENCE: 219
IGTRWHQ                                                                    7

SEQ ID NO: 220        moltype = AA   length = 7
FEATURE               Location/Qualifiers
```

```
REGION                  1..7
                        note = R3 Myelin Basic Protein
source                  1..7
                        mol_type = protein
                        organism = synthetic construct
SEQUENCE: 220
INFPFAV                                                                        7

SEQ ID NO: 221          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 221
IPIPYRT                                                                        7

SEQ ID NO: 222          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 222
IPYSQMP                                                                        7

SEQ ID NO: 223          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 223
KIITTKS                                                                        7

SEQ ID NO: 224          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 224
KMSLAPP                                                                        7

SEQ ID NO: 225          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 225
KVHHLAR                                                                        7

SEQ ID NO: 226          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 226
LELHQNV                                                                        7

SEQ ID NO: 227          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 227
LITHPQL                                                                        7

SEQ ID NO: 228          moltype = AA  length = 7
```

```
FEATURE              Location/Qualifiers
REGION               1..7
                     note = R3 Myelin Basic Protein
source               1..7
                     mol_type = protein
                     organism = synthetic construct
SEQUENCE: 228
LMLPQLE                                                                     7

SEQ ID NO: 229       moltype = AA  length = 7
FEATURE              Location/Qualifiers
REGION               1..7
                     note = R3 Myelin Basic Protein
source               1..7
                     mol_type = protein
                     organism = synthetic construct
SEQUENCE: 229
LVPPVNH                                                                     7

SEQ ID NO: 230       moltype = AA  length = 7
FEATURE              Location/Qualifiers
REGION               1..7
                     note = R3 Myelin Basic Protein
source               1..7
                     mol_type = protein
                     organism = synthetic construct
SEQUENCE: 230
MNSPLAQ                                                                     7

SEQ ID NO: 231       moltype = AA  length = 7
FEATURE              Location/Qualifiers
REGION               1..7
                     note = R3 Myelin Basic Protein
source               1..7
                     mol_type = protein
                     organism = synthetic construct
SEQUENCE: 231
MQRLGAD                                                                     7

SEQ ID NO: 232       moltype = AA  length = 7
FEATURE              Location/Qualifiers
REGION               1..7
                     note = R3 Myelin Basic Protein
source               1..7
                     mol_type = protein
                     organism = synthetic construct
SEQUENCE: 232
NGPNSLQ                                                                     7

SEQ ID NO: 233       moltype = AA  length = 7
FEATURE              Location/Qualifiers
REGION               1..7
                     note = R3 Myelin Basic Protein
source               1..7
                     mol_type = protein
                     organism = synthetic construct
SEQUENCE: 233
NGVSSSL                                                                     7

SEQ ID NO: 234       moltype = AA  length = 7
FEATURE              Location/Qualifiers
REGION               1..7
                     note = R3 Myelin Basic Protein
source               1..7
                     mol_type = protein
                     organism = synthetic construct
SEQUENCE: 234
NLTYLRF                                                                     7

SEQ ID NO: 235       moltype = AA  length = 7
FEATURE              Location/Qualifiers
REGION               1..7
                     note = R3 Myelin Basic Protein
source               1..7
                     mol_type = protein
                     organism = synthetic construct
SEQUENCE: 235
QGAYVRP                                                                     7
```

```
SEQ ID NO: 236           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 236
QKALPQT                                                                      7

SEQ ID NO: 237           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 237
QTSIMSG                                                                      7

SEQ ID NO: 238           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 238
QYWDILG                                                                      7

SEQ ID NO: 239           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 239
RGHPSQL                                                                      7

SEQ ID NO: 240           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 240
RSRKHRP                                                                      7

SEQ ID NO: 241           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 241
RTTDWWT                                                                      7

SEQ ID NO: 242           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 242
RVIPSTT                                                                      7

SEQ ID NO: 243           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 243
SAVLMPP                                                                      7
```

```
SEQ ID NO: 244          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 244
SEGLTLL                                                                   7

SEQ ID NO: 245          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 245
SGPFPLV                                                                   7

SEQ ID NO: 246          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 246
SIQTSAM                                                                   7

SEQ ID NO: 247          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 247
SKLAGFP                                                                   7

SEQ ID NO: 248          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 248
SKPHASH                                                                   7

SEQ ID NO: 249          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 249
SLDHLRL                                                                   7

SEQ ID NO: 250          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 250
SLKTTNP                                                                   7

SEQ ID NO: 251          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 251
```

```
SLWQTLR                                                                             7

SEQ ID NO: 252          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 252
SLWTHRT                                                                             7

SEQ ID NO: 253          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 253
SNAHTLP                                                                             7

SEQ ID NO: 254          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 254
SPKPDIP                                                                             7

SEQ ID NO: 255          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 255
SRHLPPL                                                                             7

SEQ ID NO: 256          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 256
SSFYVAY                                                                             7

SEQ ID NO: 257          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 257
SSMRYNS                                                                             7

SEQ ID NO: 258          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 258
SVGLPTK                                                                             7

SEQ ID NO: 259          moltype = AA  length = 7
FEATURE                 Location/Qualifiers
REGION                  1..7
                        note = R3 Myelin Basic Protein
source                  1..7
                        mol_type = protein
                        organism = synthetic construct
```

```
SEQUENCE: 259
SYRSMAP                                                                        7

SEQ ID NO: 260        moltype = AA  length = 7
FEATURE               Location/Qualifiers
REGION                1..7
                      note = R3 Myelin Basic Protein
source                1..7
                      mol_type = protein
                      organism = synthetic construct
SEQUENCE: 260
SYVTVFR                                                                        7

SEQ ID NO: 261        moltype = AA  length = 7
FEATURE               Location/Qualifiers
REGION                1..7
                      note = R3 Myelin Basic Protein
source                1..7
                      mol_type = protein
                      organism = synthetic construct
SEQUENCE: 261
TGPSSAV                                                                        7

SEQ ID NO: 262        moltype = AA  length = 7
FEATURE               Location/Qualifiers
REGION                1..7
                      note = R3 Myelin Basic Protein
source                1..7
                      mol_type = protein
                      organism = synthetic construct
SEQUENCE: 262
TGSVSKQ                                                                        7

SEQ ID NO: 263        moltype = AA  length = 7
FEATURE               Location/Qualifiers
REGION                1..7
                      note = R3 Myelin Basic Protein
source                1..7
                      mol_type = protein
                      organism = synthetic construct
SEQUENCE: 263
THKHMMT                                                                        7

SEQ ID NO: 264        moltype = AA  length = 7
FEATURE               Location/Qualifiers
REGION                1..7
                      note = R3 Myelin Basic Protein
source                1..7
                      mol_type = protein
                      organism = synthetic construct
SEQUENCE: 264
TIRVAHT                                                                        7

SEQ ID NO: 265        moltype = AA  length = 7
FEATURE               Location/Qualifiers
REGION                1..7
                      note = R3 Myelin Basic Protein
source                1..7
                      mol_type = protein
                      organism = synthetic construct
SEQUENCE: 265
TPGRATL                                                                        7

SEQ ID NO: 266        moltype = AA  length = 7
FEATURE               Location/Qualifiers
REGION                1..7
                      note = R3 Myelin Basic Protein
source                1..7
                      mol_type = protein
                      organism = synthetic construct
SEQUENCE: 266
TPVLWLP                                                                        7

SEQ ID NO: 267        moltype = AA  length = 7
FEATURE               Location/Qualifiers
REGION                1..7
                      note = R3 Myelin Basic Protein
source                1..7
                      mol_type = protein
```

```
                                         organism = synthetic construct
SEQUENCE: 267
TPVRLNT                                                                           7

SEQ ID NO: 268           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 268
TRIPILL                                                                           7

SEQ ID NO: 269           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 269
TTTQGHP                                                                           7

SEQ ID NO: 270           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 270
VGTFWTR                                                                           7

SEQ ID NO: 271           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 271
VIRTAAM                                                                           7

SEQ ID NO: 272           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 272
VLSPYHN                                                                           7

SEQ ID NO: 273           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 273
VRGTPNH                                                                           7

SEQ ID NO: 274           moltype = AA  length = 7
FEATURE                  Location/Qualifiers
REGION                   1..7
                         note = R3 Myelin Basic Protein
source                   1..7
                         mol_type = protein
                         organism = synthetic construct
SEQUENCE: 274
WDLPQNR                                                                           7

SEQ ID NO: 275           moltype = AA  length = 7
FEATURE                  Location/Qualifiers
REGION                   1..7
                         note = R3 Myelin Basic Protein
source                   1..7
```

```
                        mol_type = protein
                        organism = synthetic construct
SEQUENCE: 275
WDLRHSK                                                             7

SEQ ID NO: 276          moltype = AA   length = 7
FEATURE                 Location/Qualifiers
REGION                  1..7
                        note = R3 Myelin Basic Protein
source                  1..7
                        mol_type = protein
                        organism = synthetic construct
SEQUENCE: 276
WTYHPTT                                                             7

SEQ ID NO: 277          moltype = AA   length = 7
FEATURE                 Location/Qualifiers
REGION                  1..7
                        note = R3 Myelin Basic Protein
source                  1..7
                        mol_type = protein
                        organism = synthetic construct
SEQUENCE: 277
WVPDRSL                                                             7

SEQ ID NO: 278          moltype = AA   length = 7
FEATURE                 Location/Qualifiers
REGION                  1..7
                        note = R3 Myelin Basic Protein
source                  1..7
                        mol_type = protein
                        organism = synthetic construct
SEQUENCE: 278
YPTYLSY                                                             7

SEQ ID NO: 279          moltype = AA   length = 7
FEATURE                 Location/Qualifiers
REGION                  1..7
                        note = R3 Myelin Basic Protein
source                  1..7
                        mol_type = protein
                        organism = synthetic construct
SEQUENCE: 279
YPYVPIY                                                             7

SEQ ID NO: 280          moltype = AA   length = 7
FEATURE                 Location/Qualifiers
REGION                  1..7
                        note = R3 Myelin Basic Protein
source                  1..7
                        mol_type = protein
                        organism = synthetic construct
SEQUENCE: 280
YSSRLND                                                             7

SEQ ID NO: 281          moltype = AA   length = 7
FEATURE                 Location/Qualifiers
REGION                  1..7
                        note = R3 Myelin Basic Protein
source                  1..7
                        mol_type = protein
                        organism = synthetic construct
SEQUENCE: 281
YTASPRW                                                             7

SEQ ID NO: 282          moltype = AA   length = 7
FEATURE                 Location/Qualifiers
REGION                  1..7
                        note = R3 Myelin Basic Protein
source                  1..7
                        mol_type = protein
                        organism = synthetic construct
SEQUENCE: 282
YVNRVKQ                                                             7

SEQ ID NO: 283          moltype = AA   length = 7
FEATURE                 Location/Qualifiers
REGION                  1..7
                        note = R3 Myelin Basic Protein
```

```
source                    1..7
                          mol_type = protein
                          organism = synthetic construct
SEQUENCE: 283
AAGQRSF                                                                          7

SEQ ID NO: 284            moltype = AA   length = 7
FEATURE                   Location/Qualifiers
REGION                    1..7
                          note = R3 Myelin Basic Protein
source                    1..7
                          mol_type = protein
                          organism = synthetic construct
SEQUENCE: 284
AILTRPP                                                                          7

SEQ ID NO: 285            moltype = AA   length = 7
FEATURE                   Location/Qualifiers
REGION                    1..7
                          note = R3 Myelin Basic Protein
source                    1..7
                          mol_type = protein
                          organism = synthetic construct
SEQUENCE: 285
ALGTRPL                                                                          7

SEQ ID NO: 286            moltype = AA   length = 7
FEATURE                   Location/Qualifiers
REGION                    1..7
                          note = R3 Myelin Basic Protein
source                    1..7
                          mol_type = protein
                          organism = synthetic construct
SEQUENCE: 286
ASNTSKG                                                                          7

SEQ ID NO: 287            moltype = AA   length = 7
FEATURE                   Location/Qualifiers
REGION                    1..7
                          note = R3 Myelin Basic Protein
source                    1..7
                          mol_type = protein
                          organism = synthetic construct
SEQUENCE: 287
AVRQTTM                                                                          7

SEQ ID NO: 288            moltype = AA   length = 9
FEATURE                   Location/Qualifiers
REGION                    1..9
                          note = R3 Myelin Basic Protein
source                    1..9
                          mol_type = protein
                          organism = synthetic construct
SEQUENCE: 288
CEDSDKSVC                                                                        9

SEQ ID NO: 289            moltype = AA   length = 9
FEATURE                   Location/Qualifiers
REGION                    1..9
                          note = R3 Myelin Basic Protein
source                    1..9
                          mol_type = protein
                          organism = synthetic construct
SEQUENCE: 289
CNRVPFKQC                                                                        9

SEQ ID NO: 290            moltype = AA   length = 9
FEATURE                   Location/Qualifiers
REGION                    1..9
                          note = R3 Myelin Basic Protein
source                    1..9
                          mol_type = protein
                          organism = synthetic construct
SEQUENCE: 290
CPRMNNPLC                                                                        9

SEQ ID NO: 291            moltype = AA   length = 7
FEATURE                   Location/Qualifiers
REGION                    1..7
```

```
                        note = R3 Myelin Basic Protein
source                  1..7
                        mol_type = protein
                        organism = synthetic construct
SEQUENCE: 291
DVVKDVI                                                                 7

SEQ ID NO: 292          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 292
ESPYPHS                                                                 7

SEQ ID NO: 293          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 293
FKLPWAS                                                                 7

SEQ ID NO: 294          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 294
FLNQAPT                                                                 7

SEQ ID NO: 295          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 295
FSAGVGK                                                                 7

SEQ ID NO: 296          moltype = AA  length = 12
FEATURE                 Location/Qualifiers
REGION                  1..12
                        note = R3 Myelin Basic Protein
source                  1..12
                        mol_type = protein
                        organism = synthetic construct
SEQUENCE: 296
GHSHYILGKP TA                                                          12

SEQ ID NO: 297          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 297
GPITHAI                                                                 7

SEQ ID NO: 298          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 298
HFLRPSD                                                                 7

SEQ ID NO: 299          moltype = AA  length = 7
FEATURE                 Location/Qualifiers
```

```
REGION                  1..7
                        note = R3 Myelin Basic Protein
source                  1..7
                        mol_type = protein
                        organism = synthetic construct
SEQUENCE: 299
HLLKTHS                                                                  7

SEQ ID NO: 300          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 300
HMAGVNQ                                                                  7

SEQ ID NO: 301          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 301
HPDTLPQ                                                                  7

SEQ ID NO: 302          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 302
HPTGTPT                                                                  7

SEQ ID NO: 303          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 303
HTGLRSL                                                                  7

SEQ ID NO: 304          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 304
KGQPLFR                                                                  7

SEQ ID NO: 305          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 305
KYRHGAE                                                                  7

SEQ ID NO: 306          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 306
LFRRVTE                                                                  7

SEQ ID NO: 307          moltype = AA  length = 7
```

```
FEATURE              Location/Qualifiers
REGION               1..7
                     note = R3 Myelin Basic Protein
source               1..7
                     mol_type = protein
                     organism = synthetic construct
SEQUENCE: 307
LTKSLNH                                                              7

SEQ ID NO: 308       moltype = AA  length = 7
FEATURE              Location/Qualifiers
REGION               1..7
                     note = R3 Myelin Basic Protein
source               1..7
                     mol_type = protein
                     organism = synthetic construct
SEQUENCE: 308
MPLLELP                                                              7

SEQ ID NO: 309       moltype = AA  length = 7
FEATURE              Location/Qualifiers
REGION               1..7
                     note = R3 Myelin Basic Protein
source               1..7
                     mol_type = protein
                     organism = synthetic construct
SEQUENCE: 309
MTNHGNA                                                              7

SEQ ID NO: 310       moltype = AA  length = 7
FEATURE              Location/Qualifiers
REGION               1..7
                     note = R3 Myelin Basic Protein
source               1..7
                     mol_type = protein
                     organism = synthetic construct
SEQUENCE: 310
NLKLWTR                                                              7

SEQ ID NO: 311       moltype = AA  length = 7
FEATURE              Location/Qualifiers
REGION               1..7
                     note = R3 Myelin Basic Protein
source               1..7
                     mol_type = protein
                     organism = synthetic construct
SEQUENCE: 311
NLLQGVM                                                              7

SEQ ID NO: 312       moltype = AA  length = 7
FEATURE              Location/Qualifiers
REGION               1..7
                     note = R3 Myelin Basic Protein
source               1..7
                     mol_type = protein
                     organism = synthetic construct
SEQUENCE: 312
NMYPRVT                                                              7

SEQ ID NO: 313       moltype = AA  length = 7
FEATURE              Location/Qualifiers
REGION               1..7
                     note = R3 Myelin Basic Protein
source               1..7
                     mol_type = protein
                     organism = synthetic construct
SEQUENCE: 313
NSSPHQI                                                              7

SEQ ID NO: 314       moltype = AA  length = 7
FEATURE              Location/Qualifiers
REGION               1..7
                     note = R3 Myelin Basic Protein
source               1..7
                     mol_type = protein
                     organism = synthetic construct
SEQUENCE: 314
QGTLFDT                                                              7
```

```
SEQ ID NO: 315          moltype = AA   length = 7
FEATURE                 Location/Qualifiers
REGION                  1..7
                        note = R3 Myelin Basic Protein
source                  1..7
                        mol_type = protein
                        organism = synthetic construct
SEQUENCE: 315
QPIDSTS                                                                  7

SEQ ID NO: 316          moltype = AA   length = 7
FEATURE                 Location/Qualifiers
REGION                  1..7
                        note = R3 Myelin Basic Protein
source                  1..7
                        mol_type = protein
                        organism = synthetic construct
SEQUENCE: 316
SEPGTVR                                                                  7

SEQ ID NO: 317          moltype = AA   length = 7
FEATURE                 Location/Qualifiers
REGION                  1..7
                        note = R3 Myelin Basic Protein
source                  1..7
                        mol_type = protein
                        organism = synthetic construct
SEQUENCE: 317
SGNLKKA                                                                  7

SEQ ID NO: 318          moltype = AA   length = 12
FEATURE                 Location/Qualifiers
REGION                  1..12
                        note = R3 Myelin Basic Protein
source                  1..12
                        mol_type = protein
                        organism = synthetic construct
SEQUENCE: 318
SIAEVLGLWR NV                                                           12

SEQ ID NO: 319          moltype = AA   length = 7
FEATURE                 Location/Qualifiers
REGION                  1..7
                        note = R3 Myelin Basic Protein
source                  1..7
                        mol_type = protein
                        organism = synthetic construct
SEQUENCE: 319
SIRMTEI                                                                  7

SEQ ID NO: 320          moltype = AA   length = 7
FEATURE                 Location/Qualifiers
REGION                  1..7
                        note = R3 Myelin Basic Protein
source                  1..7
                        mol_type = protein
                        organism = synthetic construct
SEQUENCE: 320
SISKIRT                                                                  7

SEQ ID NO: 321          moltype = AA   length = 7
FEATURE                 Location/Qualifiers
REGION                  1..7
                        note = R3 Myelin Basic Protein
source                  1..7
                        mol_type = protein
                        organism = synthetic construct
SEQUENCE: 321
SLRSVGA                                                                  7

SEQ ID NO: 322          moltype = AA   length = 7
FEATURE                 Location/Qualifiers
REGION                  1..7
                        note = R3 Myelin Basic Protein
source                  1..7
                        mol_type = protein
                        organism = synthetic construct
SEQUENCE: 322
SSGMLSK                                                                  7
```

```
SEQ ID NO: 323        moltype = AA   length = 7
FEATURE               Location/Qualifiers
REGION                1..7
                      note = R3 Myelin Basic Protein
source                1..7
                      mol_type = protein
                      organism = synthetic construct
SEQUENCE: 323
SYTLSRS                                                                7

SEQ ID NO: 324        moltype = AA   length = 7
FEATURE               Location/Qualifiers
REGION                1..7
                      note = R3 Myelin Basic Protein
source                1..7
                      mol_type = protein
                      organism = synthetic construct
SEQUENCE: 324
TLLTALT                                                                7

SEQ ID NO: 325        moltype = AA   length = 7
FEATURE               Location/Qualifiers
REGION                1..7
                      note = R3 Myelin Basic Protein
source                1..7
                      mol_type = protein
                      organism = synthetic construct
SEQUENCE: 325
TPLYLSS                                                                7

SEQ ID NO: 326        moltype = AA   length = 7
FEATURE               Location/Qualifiers
REGION                1..7
                      note = R3 Myelin Basic Protein
source                1..7
                      mol_type = protein
                      organism = synthetic construct
SEQUENCE: 326
VSFTLEP                                                                7

SEQ ID NO: 327        moltype = AA   length = 7
FEATURE               Location/Qualifiers
REGION                1..7
                      note = R3 Myelin Basic Protein
source                1..7
                      mol_type = protein
                      organism = synthetic construct
SEQUENCE: 327
VVDMSTY                                                                7

SEQ ID NO: 328        moltype = AA   length = 7
FEATURE               Location/Qualifiers
REGION                1..7
                      note = R3 Myelin Basic Protein
source                1..7
                      mol_type = protein
                      organism = synthetic construct
SEQUENCE: 328
WPDLRIL                                                                7

SEQ ID NO: 329        moltype = AA   length = 7
FEATURE               Location/Qualifiers
REGION                1..7
                      note = R3 Myelin Basic Protein
source                1..7
                      mol_type = protein
                      organism = synthetic construct
SEQUENCE: 329
WSLPLLS                                                                7

SEQ ID NO: 330        moltype = AA   length = 7
FEATURE               Location/Qualifiers
REGION                1..7
                      note = R3 Myelin Basic Protein
source                1..7
                      mol_type = protein
                      organism = synthetic construct
SEQUENCE: 330
```

-continued

```
WSPRWPS                                                              7

SEQ ID NO: 331         moltype = AA   length = 7
FEATURE                Location/Qualifiers
REGION                 1..7
                       note = R3 Myelin Basic Protein
source                 1..7
                       mol_type = protein
                       organism = synthetic construct
SEQUENCE: 331
YLPPPLP                                                              7

SEQ ID NO: 332         moltype = AA   length = 7
FEATURE                Location/Qualifiers
REGION                 1..7
                       note = R3 Myelin Basic Protein
source                 1..7
                       mol_type = protein
                       organism = synthetic construct
SEQUENCE: 332
DSYLLSA                                                              7

SEQ ID NO: 333         moltype = AA   length = 7
FEATURE                Location/Qualifiers
REGION                 1..7
                       note = R3 Myelin Basic Protein
source                 1..7
                       mol_type = protein
                       organism = synthetic construct
SEQUENCE: 333
FVLPNKN                                                              7

SEQ ID NO: 334         moltype = AA   length = 7
FEATURE                Location/Qualifiers
REGION                 1..7
                       note = R3 Myelin Basic Protein
source                 1..7
                       mol_type = protein
                       organism = synthetic construct
SEQUENCE: 334
IILPSAQ                                                              7

SEQ ID NO: 335         moltype = AA   length = 7
FEATURE                Location/Qualifiers
REGION                 1..7
                       note = R3 Myelin Basic Protein
source                 1..7
                       mol_type = protein
                       organism = synthetic construct
SEQUENCE: 335
KNSIAPR                                                              7

SEQ ID NO: 336         moltype = AA   length = 7
FEATURE                Location/Qualifiers
REGION                 1..7
                       note = R3 Myelin Basic Protein
source                 1..7
                       mol_type = protein
                       organism = synthetic construct
SEQUENCE: 336
LPPQISR                                                              7

SEQ ID NO: 337         moltype = AA   length = 7
FEATURE                Location/Qualifiers
REGION                 1..7
                       note = R3 Myelin Basic Protein
source                 1..7
                       mol_type = protein
                       organism = synthetic construct
SEQUENCE: 337
MPSLKHQ                                                              7

SEQ ID NO: 338         moltype = AA   length = 7
FEATURE                Location/Qualifiers
REGION                 1..7
                       note = R3 Myelin Basic Protein
source                 1..7
                       mol_type = protein
                       organism = synthetic construct
```

```
SEQUENCE: 338
NPTDTNK                                                                    7

SEQ ID NO: 339          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 339
NTSLSFK                                                                    7

SEQ ID NO: 340          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 340
QNSYLSN                                                                    7

SEQ ID NO: 341          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 341
QQAHLQS                                                                    7

SEQ ID NO: 342          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 342
SPPRFIP                                                                    7

SEQ ID NO: 343          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 343
SWFESHN                                                                    7

SEQ ID NO: 344          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 344
TPQVMLK                                                                    7

SEQ ID NO: 345          moltype = AA  length = 7
FEATURE                 Location/Qualifiers
REGION                  1..7
                        note = R3 Myelin Basic Protein
source                  1..7
                        mol_type = protein
                        organism = synthetic construct
SEQUENCE: 345
TSPPLAH                                                                    7

SEQ ID NO: 346          moltype = AA  length = 7
FEATURE                 Location/Qualifiers
REGION                  1..7
                        note = R3 Myelin Basic Protein
source                  1..7
                        mol_type = protein
```

```
                          organism = synthetic construct
SEQUENCE: 346
TSRLVST                                                                    7

SEQ ID NO: 347            moltype = AA  length = 7
FEATURE                   Location/Qualifiers
REGION                    1..7
                          note = R3 Myelin Basic Protein
source                    1..7
                          mol_type = protein
                          organism = synthetic construct
SEQUENCE: 347
VAHQRVS                                                                    7

SEQ ID NO: 348            moltype = AA  length = 7
FEATURE                   Location/Qualifiers
REGION                    1..7
                          note = R3 Myelin Basic Protein
source                    1..7
                          mol_type = protein
                          organism = synthetic construct
SEQUENCE: 348
VPTLRIP                                                                    7

SEQ ID NO: 349            moltype = AA  length = 7
FEATURE                   Location/Qualifiers
REGION                    1..7
                          note = R3 Myelin Basic Protein
source                    1..7
                          mol_type = protein
                          organism = synthetic construct
SEQUENCE: 349
YATATPS                                                                    7

SEQ ID NO: 350            moltype = AA  length = 7
FEATURE                   Location/Qualifiers
REGION                    1..7
                          note = R3 Myelin Basic Protein
source                    1..7
                          mol_type = protein
                          organism = synthetic construct
SEQUENCE: 350
ANLSRSV                                                                    7

SEQ ID NO: 351            moltype = AA  length = 7
FEATURE                   Location/Qualifiers
REGION                    1..7
                          note = R3 Myelin Basic Protein
source                    1..7
                          mol_type = protein
                          organism = synthetic construct
SEQUENCE: 351
FSARTNT                                                                    7

SEQ ID NO: 352            moltype = AA  length = 7
FEATURE                   Location/Qualifiers
REGION                    1..7
                          note = R3 Myelin Basic Protein
source                    1..7
                          mol_type = protein
                          organism = synthetic construct
SEQUENCE: 352
HFYGPGP                                                                    7

SEQ ID NO: 353            moltype = AA  length = 7
FEATURE                   Location/Qualifiers
REGION                    1..7
                          note = R3 Myelin Basic Protein
source                    1..7
                          mol_type = protein
                          organism = synthetic construct
SEQUENCE: 353
HPWLGNR                                                                    7

SEQ ID NO: 354            moltype = AA  length = 7
FEATURE                   Location/Qualifiers
REGION                    1..7
                          note = R3 Myelin Basic Protein
source                    1..7
```

```
                          mol_type = protein
                          organism = synthetic construct
SEQUENCE: 354
HYSPNVM                                                                 7

SEQ ID NO: 355            moltype = AA   length = 7
FEATURE                   Location/Qualifiers
REGION                    1..7
                          note = R3 Myelin Basic Protein
source                    1..7
                          mol_type = protein
                          organism = synthetic construct
SEQUENCE: 355
NFAQHMQ                                                                 7

SEQ ID NO: 356            moltype = AA   length = 7
FEATURE                   Location/Qualifiers
REGION                    1..7
                          note = R3 Myelin Basic Protein
source                    1..7
                          mol_type = protein
                          organism = synthetic construct
SEQUENCE: 356
SNAERWR                                                                 7

SEQ ID NO: 357            moltype = AA   length = 7
FEATURE                   Location/Qualifiers
REGION                    1..7
                          note = R3 Myelin Basic Protein
source                    1..7
                          mol_type = protein
                          organism = synthetic construct
SEQUENCE: 357
SRPTRVP                                                                 7

SEQ ID NO: 358            moltype = AA   length = 7
FEATURE                   Location/Qualifiers
REGION                    1..7
                          note = R3 Myelin Basic Protein
source                    1..7
                          mol_type = protein
                          organism = synthetic construct
SEQUENCE: 358
SVEYGQL                                                                 7

SEQ ID NO: 359            moltype = AA   length = 7
FEATURE                   Location/Qualifiers
REGION                    1..7
                          note = R3 Myelin Basic Protein
source                    1..7
                          mol_type = protein
                          organism = synthetic construct
SEQUENCE: 359
TGNLRLY                                                                 7

SEQ ID NO: 360            moltype = AA   length = 7
FEATURE                   Location/Qualifiers
REGION                    1..7
                          note = R3 Myelin Basic Protein
source                    1..7
                          mol_type = protein
                          organism = synthetic construct
SEQUENCE: 360
MDLSLKP                                                                 7

SEQ ID NO: 361            moltype = AA   length = 7
FEATURE                   Location/Qualifiers
REGION                    1..7
                          note = R3 Myelin Basic Protein
source                    1..7
                          mol_type = protein
                          organism = synthetic construct
SEQUENCE: 361
NTPKVLA                                                                 7

SEQ ID NO: 362            moltype = AA   length = 7
FEATURE                   Location/Qualifiers
REGION                    1..7
                          note = R3 Myelin Basic Protein
```

```
source                   1..7
                         mol_type = protein
                         organism = synthetic construct
SEQUENCE: 362
TQMTMDS                                                                        7

SEQ ID NO: 363           moltype = AA  length = 7
FEATURE                  Location/Qualifiers
REGION                   1..7
                         note = R3 Myelin PLP
source                   1..7
                         mol_type = protein
                         organism = synthetic construct
SEQUENCE: 363
ASLTLAL                                                                        7

SEQ ID NO: 364           moltype = AA  length = 7
FEATURE                  Location/Qualifiers
REGION                   1..7
                         note = R3 Myelin PLP
source                   1..7
                         mol_type = protein
                         organism = synthetic construct
SEQUENCE: 364
DRHEGHR                                                                        7

SEQ ID NO: 365           moltype = AA  length = 7
FEATURE                  Location/Qualifiers
REGION                   1..7
                         note = R3 Myelin PLP
source                   1..7
                         mol_type = protein
                         organism = synthetic construct
SEQUENCE: 365
FRIDKSM                                                                        7

SEQ ID NO: 366           moltype = AA  length = 7
FEATURE                  Location/Qualifiers
REGION                   1..7
                         note = R3 Myelin PLP
source                   1..7
                         mol_type = protein
                         organism = synthetic construct
SEQUENCE: 366
GHLQSLF                                                                        7

SEQ ID NO: 367           moltype = AA  length = 7
FEATURE                  Location/Qualifiers
REGION                   1..7
                         note = R3 Myelin PLP
source                   1..7
                         mol_type = protein
                         organism = synthetic construct
SEQUENCE: 367
GLWGPSL                                                                        7

SEQ ID NO: 368           moltype = AA  length = 7
FEATURE                  Location/Qualifiers
REGION                   1..7
                         note = R3 Myelin PLP
source                   1..7
                         mol_type = protein
                         organism = synthetic construct
SEQUENCE: 368
KPSASIY                                                                        7

SEQ ID NO: 369           moltype = AA  length = 7
FEATURE                  Location/Qualifiers
REGION                   1..7
                         note = R3 Myelin PLP
source                   1..7
                         mol_type = protein
                         organism = synthetic construct
SEQUENCE: 369
LPSHASI                                                                        7

SEQ ID NO: 370           moltype = AA  length = 7
FEATURE                  Location/Qualifiers
REGION                   1..7
```

```
                            note = R3 Myelin PLP
source                      1..7
                            mol_type = protein
                            organism = synthetic construct
SEQUENCE: 370
LPVKNLL                                                                 7

SEQ ID NO: 371              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 371
MKIMPMD                                                                 7

SEQ ID NO: 372              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 372
SAQSRSF                                                                 7

SEQ ID NO: 373              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 373
SLPSLLP                                                                 7

SEQ ID NO: 374              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 374
SVVYQNS                                                                 7

SEQ ID NO: 375              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 375
TTTIADM                                                                 7

SEQ ID NO: 376              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 376
VTGPGTP                                                                 7

SEQ ID NO: 377              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 377
VTPNKAR                                                                 7

SEQ ID NO: 378              moltype = AA  length = 7
FEATURE                     Location/Qualifiers
```

```
REGION                      1..7
                            note = R3 Myelin PLP
source                      1..7
                            mol_type = protein
                            organism = synthetic construct
SEQUENCE: 378
WHYTPSM                                                                          7

SEQ ID NO: 379              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 379
WSRISVD                                                                          7

SEQ ID NO: 380              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 380
ALFQERK                                                                          7

SEQ ID NO: 381              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 381
AQASSAR                                                                          7

SEQ ID NO: 382              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 382
EVLYPNN                                                                          7

SEQ ID NO: 383              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 383
HLHTRPT                                                                          7

SEQ ID NO: 384              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 384
IRPTHNG                                                                          7

SEQ ID NO: 385              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 385
KGVIPAT                                                                          7

SEQ ID NO: 386              moltype = AA  length = 7
```

-continued

```
FEATURE              Location/Qualifiers
REGION               1..7
                     note = R3 Myelin PLP
source               1..7
                     mol_type = protein
                     organism = synthetic construct
SEQUENCE: 386
LHQTYRP                                                              7

SEQ ID NO: 387       moltype = AA  length = 7
FEATURE              Location/Qualifiers
REGION               1..7
                     note = R3 Myelin PLP
source               1..7
                     mol_type = protein
                     organism = synthetic construct
SEQUENCE: 387
LPHRLNP                                                              7

SEQ ID NO: 388       moltype = AA  length = 7
FEATURE              Location/Qualifiers
REGION               1..7
                     note = R3 Myelin PLP
source               1..7
                     mol_type = protein
                     organism = synthetic construct
SEQUENCE: 388
TGISSTP                                                              7

SEQ ID NO: 389       moltype = AA  length = 7
FEATURE              Location/Qualifiers
REGION               1..7
                     note = R3 Myelin PLP
source               1..7
                     mol_type = protein
                     organism = synthetic construct
SEQUENCE: 389
TMPIKAM                                                              7

SEQ ID NO: 390       moltype = AA  length = 7
FEATURE              Location/Qualifiers
REGION               1..7
                     note = R3 Myelin PLP
source               1..7
                     mol_type = protein
                     organism = synthetic construct
SEQUENCE: 390
VPGHISG                                                              7

SEQ ID NO: 391       moltype = AA  length = 7
FEATURE              Location/Qualifiers
REGION               1..7
                     note = R3 Myelin PLP
source               1..7
                     mol_type = protein
                     organism = synthetic construct
SEQUENCE: 391
VSASWMP                                                              7

SEQ ID NO: 392       moltype = AA  length = 7
FEATURE              Location/Qualifiers
REGION               1..7
                     note = R3 Myelin PLP
source               1..7
                     mol_type = protein
                     organism = synthetic construct
SEQUENCE: 392
WSPHGYK                                                              7

SEQ ID NO: 393       moltype = AA  length = 7
FEATURE              Location/Qualifiers
REGION               1..7
                     note = R3 Myelin PLP
source               1..7
                     mol_type = protein
                     organism = synthetic construct
SEQUENCE: 393
YSQAISA                                                              7
```

| | | |
|---|---|---|
| SEQ ID NO: 394<br>FEATURE<br>REGION<br><br>source<br><br><br>SEQUENCE: 394<br>AVVAMNK | moltype = AA   length = 7<br>Location/Qualifiers<br>1..7<br>note = R3 Myelin PLP<br>1..7<br>mol_type = protein<br>organism = synthetic construct<br><br> | <br><br><br><br><br><br><br><br>7 |
| SEQ ID NO: 395<br>FEATURE<br>REGION<br><br>source<br><br><br>SEQUENCE: 395<br>GIPSSKN | moltype = AA   length = 7<br>Location/Qualifiers<br>1..7<br>note = R3 Myelin PLP<br>1..7<br>mol_type = protein<br>organism = synthetic construct<br><br> | <br><br><br><br><br><br><br><br>7 |
| SEQ ID NO: 396<br>FEATURE<br>REGION<br><br>source<br><br><br>SEQUENCE: 396<br>NDASTVS | moltype = AA   length = 7<br>Location/Qualifiers<br>1..7<br>note = R3 Myelin PLP<br>1..7<br>mol_type = protein<br>organism = synthetic construct<br><br> | <br><br><br><br><br><br><br><br>7 |
| SEQ ID NO: 397<br>FEATURE<br>REGION<br><br>source<br><br><br>SEQUENCE: 397<br>QLPRNNL | moltype = AA   length = 7<br>Location/Qualifiers<br>1..7<br>note = R3 Myelin PLP<br>1..7<br>mol_type = protein<br>organism = synthetic construct<br><br> | <br><br><br><br><br><br><br><br>7 |
| SEQ ID NO: 398<br>FEATURE<br>REGION<br><br>source<br><br><br>SEQUENCE: 398<br>SLNRGGA | moltype = AA   length = 7<br>Location/Qualifiers<br>1..7<br>note = R3 Myelin PLP<br>1..7<br>mol_type = protein<br>organism = synthetic construct<br><br> | <br><br><br><br><br><br><br><br>7 |
| SEQ ID NO: 399<br>FEATURE<br>REGION<br><br>source<br><br><br>SEQUENCE: 399<br>SLPGYRH | moltype = AA   length = 7<br>Location/Qualifiers<br>1..7<br>note = R3 Myelin PLP<br>1..7<br>mol_type = protein<br>organism = synthetic construct<br><br> | <br><br><br><br><br><br><br><br>7 |
| SEQ ID NO: 400<br>FEATURE<br>REGION<br><br>source<br><br><br>SEQUENCE: 400<br>SVLPDKL | moltype = AA   length = 7<br>Location/Qualifiers<br>1..7<br>note = R3 Myelin PLP<br>1..7<br>mol_type = protein<br>organism = synthetic construct<br><br> | <br><br><br><br><br><br><br><br>7 |
| SEQ ID NO: 401<br>FEATURE<br>REGION<br><br>source<br><br><br>SEQUENCE: 401<br>TLWAQKT | moltype = AA   length = 7<br>Location/Qualifiers<br>1..7<br>note = R3 Myelin PLP<br>1..7<br>mol_type = protein<br>organism = synthetic construct<br><br> | <br><br><br><br><br><br><br><br>7 |

```
SEQ ID NO: 402          moltype = AA   length = 7
FEATURE                 Location/Qualifiers
REGION                  1..7
                        note = R3 Myelin PLP
source                  1..7
                        mol_type = protein
                        organism = synthetic construct
SEQUENCE: 402
TQPRYPS                                                                  7

SEQ ID NO: 403          moltype = AA   length = 7
FEATURE                 Location/Qualifiers
REGION                  1..7
                        note = R3 Myelin PLP
source                  1..7
                        mol_type = protein
                        organism = synthetic construct
SEQUENCE: 403
VFPERRV                                                                  7

SEQ ID NO: 404          moltype = AA   length = 7
FEATURE                 Location/Qualifiers
REGION                  1..7
                        note = R3 Myelin PLP
source                  1..7
                        mol_type = protein
                        organism = synthetic construct
SEQUENCE: 404
VGYRSAS                                                                  7

SEQ ID NO: 405          moltype = AA   length = 7
FEATURE                 Location/Qualifiers
REGION                  1..7
                        note = R3 Myelin PLP
source                  1..7
                        mol_type = protein
                        organism = synthetic construct
SEQUENCE: 405
VRTSMNH                                                                  7

SEQ ID NO: 406          moltype = AA   length = 7
FEATURE                 Location/Qualifiers
REGION                  1..7
                        note = R3 Myelin PLP
source                  1..7
                        mol_type = protein
                        organism = synthetic construct
SEQUENCE: 406
YTWTPSR                                                                  7

SEQ ID NO: 407          moltype = AA   length = 7
FEATURE                 Location/Qualifiers
REGION                  1..7
                        note = R3 Myelin PLP
source                  1..7
                        mol_type = protein
                        organism = synthetic construct
SEQUENCE: 407
FSLDRDG                                                                  7

SEQ ID NO: 408          moltype = AA   length = 7
FEATURE                 Location/Qualifiers
REGION                  1..7
                        note = R3 Myelin PLP
source                  1..7
                        mol_type = protein
                        organism = synthetic construct
SEQUENCE: 408
FSTPTNV                                                                  7

SEQ ID NO: 409          moltype = AA   length = 7
FEATURE                 Location/Qualifiers
REGION                  1..7
                        note = R3 Myelin PLP
source                  1..7
                        mol_type = protein
                        organism = synthetic construct
SEQUENCE: 409
```

```
GPAAVII                                                                   7

SEQ ID NO: 410          moltype = AA   length = 7
FEATURE                 Location/Qualifiers
REGION                  1..7
                        note = R3 Myelin PLP
source                  1..7
                        mol_type = protein
                        organism = synthetic construct
SEQUENCE: 410
GWSTAIR                                                                   7

SEQ ID NO: 411          moltype = AA   length = 7
FEATURE                 Location/Qualifiers
REGION                  1..7
                        note = R3 Myelin PLP
source                  1..7
                        mol_type = protein
                        organism = synthetic construct
SEQUENCE: 411
HKAPLGT                                                                   7

SEQ ID NO: 412          moltype = AA   length = 7
FEATURE                 Location/Qualifiers
REGION                  1..7
                        note = R3 Myelin PLP
source                  1..7
                        mol_type = protein
                        organism = synthetic construct
SEQUENCE: 412
IDRVRGL                                                                   7

SEQ ID NO: 413          moltype = AA   length = 7
FEATURE                 Location/Qualifiers
REGION                  1..7
                        note = R3 Myelin PLP
source                  1..7
                        mol_type = protein
                        organism = synthetic construct
SEQUENCE: 413
LMQKPSI                                                                   7

SEQ ID NO: 414          moltype = AA   length = 7
FEATURE                 Location/Qualifiers
REGION                  1..7
                        note = R3 Myelin PLP
source                  1..7
                        mol_type = protein
                        organism = synthetic construct
SEQUENCE: 414
SVMWMTP                                                                   7

SEQ ID NO: 415          moltype = AA   length = 7
FEATURE                 Location/Qualifiers
REGION                  1..7
                        note = R3 Myelin PLP
source                  1..7
                        mol_type = protein
                        organism = synthetic construct
SEQUENCE: 415
TKITPHR                                                                   7

SEQ ID NO: 416          moltype = AA   length = 7
FEATURE                 Location/Qualifiers
REGION                  1..7
                        note = R3 Myelin PLP
source                  1..7
                        mol_type = protein
                        organism = synthetic construct
SEQUENCE: 416
YSSRLTA                                                                   7

SEQ ID NO: 417          moltype = AA   length = 7
FEATURE                 Location/Qualifiers
REGION                  1..7
                        note = R3 Myelin PLP
source                  1..7
                        mol_type = protein
                        organism = synthetic construct
```

```
SEQUENCE: 417
ARFVPLT                                                                          7

SEQ ID NO: 418         moltype = AA  length = 7
FEATURE                Location/Qualifiers
REGION                 1..7
                       note = R3 Myelin PLP
source                 1..7
                       mol_type = protein
                       organism = synthetic construct
SEQUENCE: 418
DGSRDLV                                                                          7

SEQ ID NO: 419         moltype = AA  length = 7
FEATURE                Location/Qualifiers
REGION                 1..7
                       note = R3 Myelin PLP
source                 1..7
                       mol_type = protein
                       organism = synthetic construct
SEQUENCE: 419
EKSTTVA                                                                          7

SEQ ID NO: 420         moltype = AA  length = 7
FEATURE                Location/Qualifiers
REGION                 1..7
                       note = R3 Myelin PLP
source                 1..7
                       mol_type = protein
                       organism = synthetic construct
SEQUENCE: 420
YSDTYKH                                                                          7

SEQ ID NO: 421         moltype = AA  length = 7
FEATURE                Location/Qualifiers
REGION                 1..7
                       note = R3 Myelin PLP
source                 1..7
                       mol_type = protein
                       organism = synthetic construct
SEQUENCE: 421
EPSSFTF                                                                          7

SEQ ID NO: 422         moltype = AA  length = 7
FEATURE                Location/Qualifiers
REGION                 1..7
                       note = R3 Myelin PLP
source                 1..7
                       mol_type = protein
                       organism = synthetic construct
SEQUENCE: 422
GKSYSQI                                                                          7

SEQ ID NO: 423         moltype = AA  length = 7
FEATURE                Location/Qualifiers
REGION                 1..7
                       note = R3 Myelin PLP
source                 1..7
                       mol_type = protein
                       organism = synthetic construct
SEQUENCE: 423
GNVFQTS                                                                          7

SEQ ID NO: 424         moltype = AA  length = 7
FEATURE                Location/Qualifiers
REGION                 1..7
                       note = R3 Myelin PLP
source                 1..7
                       mol_type = protein
                       organism = synthetic construct
SEQUENCE: 424
IIPPTSV                                                                          7

SEQ ID NO: 425         moltype = AA  length = 7
FEATURE                Location/Qualifiers
REGION                 1..7
                       note = R3 Myelin PLP
source                 1..7
                       mol_type = protein
```

```
                          organism = synthetic construct
SEQUENCE: 425
LPLRLHA                                                                7

SEQ ID NO: 426            moltype = AA   length = 7
FEATURE                   Location/Qualifiers
REGION                    1..7
                          note = R3 Myelin PLP
source                    1..7
                          mol_type = protein
                          organism = synthetic construct
SEQUENCE: 426
NVFSATP                                                                7

SEQ ID NO: 427            moltype = AA   length = 7
FEATURE                   Location/Qualifiers
REGION                    1..7
                          note = R3 Myelin PLP
source                    1..7
                          mol_type = protein
                          organism = synthetic construct
SEQUENCE: 427
QRRSVIL                                                                7

SEQ ID NO: 428            moltype = AA   length = 7
FEATURE                   Location/Qualifiers
REGION                    1..7
                          note = R3 Myelin PLP
source                    1..7
                          mol_type = protein
                          organism = synthetic construct
SEQUENCE: 428
SGVATYT                                                                7

SEQ ID NO: 429            moltype = AA   length = 7
FEATURE                   Location/Qualifiers
REGION                    1..7
                          note = R3 Myelin PLP
source                    1..7
                          mol_type = protein
                          organism = synthetic construct
SEQUENCE: 429
SWDVLEL                                                                7

SEQ ID NO: 430            moltype = AA   length = 7
FEATURE                   Location/Qualifiers
REGION                    1..7
                          note = R3 Myelin PLP
source                    1..7
                          mol_type = protein
                          organism = synthetic construct
SEQUENCE: 430
TFPERLR                                                                7

SEQ ID NO: 431            moltype = AA   length = 7
FEATURE                   Location/Qualifiers
REGION                    1..7
                          note = R3 Myelin PLP
source                    1..7
                          mol_type = protein
                          organism = synthetic construct
SEQUENCE: 431
WSPHRSF                                                                7

SEQ ID NO: 432            moltype = AA   length = 7
FEATURE                   Location/Qualifiers
REGION                    1..7
                          note = R3 Myelin PLP
source                    1..7
                          mol_type = protein
                          organism = synthetic construct
SEQUENCE: 432
IHHLESS                                                                7

SEQ ID NO: 433            moltype = AA   length = 7
FEATURE                   Location/Qualifiers
REGION                    1..7
                          note = R3 Myelin PLP
source                    1..7
```

```
                            mol_type = protein
                            organism = synthetic construct
SEQUENCE: 433
LNGISAL                                                                 7

SEQ ID NO: 434              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 434
SALISTR                                                                 7

SEQ ID NO: 435              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 435
SGLHYAL                                                                 7

SEQ ID NO: 436              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 436
TRASYPQ                                                                 7

SEQ ID NO: 437              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 437
NIPSSIL                                                                 7

SEQ ID NO: 438              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 438
QPNMLKP                                                                 7

SEQ ID NO: 439              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 439
RLQPEPT                                                                 7

SEQ ID NO: 440              moltype = AA  length = 7
FEATURE                     Location/Qualifiers
REGION                      1..7
                            note = R3 Myelin PLP
source                      1..7
                            mol_type = protein
                            organism = synthetic construct
SEQUENCE: 440
SVEKYSK                                                                 7

SEQ ID NO: 441              moltype = AA  length = 7
FEATURE                     Location/Qualifiers
REGION                      1..7
                            note = R3 Myelin PLP
```

```
source                      1..7
                            mol_type = protein
                            organism = synthetic construct
SEQUENCE: 441
VSSQEQA                                                              7

SEQ ID NO: 442              moltype = AA   length = 7
FEATURE                     Location/Qualifiers
REGION                      1..7
                            note = R3 Myelin PLP
source                      1..7
                            mol_type = protein
                            organism = synthetic construct
SEQUENCE: 442
WNTADRL                                                              7

SEQ ID NO: 443              moltype = AA   length = 7
FEATURE                     Location/Qualifiers
REGION                      1..7
                            note = R3 Myelin PLP
source                      1..7
                            mol_type = protein
                            organism = synthetic construct
SEQUENCE: 443
MPHAPVQ                                                              7

SEQ ID NO: 444              moltype = AA   length = 7
FEATURE                     Location/Qualifiers
REGION                      1..7
                            note = R3 Myelin PLP
source                      1..7
                            mol_type = protein
                            organism = synthetic construct
SEQUENCE: 444
TDVEMVP                                                              7

SEQ ID NO: 445              moltype = AA   length = 7
FEATURE                     Location/Qualifiers
REGION                      1..7
                            note = R3 Myelin PLP
source                      1..7
                            mol_type = protein
                            organism = synthetic construct
SEQUENCE: 445
AHQSSVT                                                              7

SEQ ID NO: 446              moltype = AA   length = 7
FEATURE                     Location/Qualifiers
REGION                      1..7
                            note = R3 Myelin PLP
source                      1..7
                            mol_type = protein
                            organism = synthetic construct
SEQUENCE: 446
GSAWKKH                                                              7

SEQ ID NO: 447              moltype = AA   length = 9
FEATURE                     Location/Qualifiers
REGION                      1..9
                            note = R3 Nidogen-2
source                      1..9
                            mol_type = protein
                            organism = synthetic construct
SEQUENCE: 447
CIHHKGVLC                                                            9

SEQ ID NO: 448              moltype = AA   length = 9
FEATURE                     Location/Qualifiers
REGION                      1..9
                            note = R3 Nidogen-2
source                      1..9
                            mol_type = protein
                            organism = synthetic construct
SEQUENCE: 448
CKDGHIRHC                                                            9

SEQ ID NO: 449              moltype = AA   length = 9
FEATURE                     Location/Qualifiers
REGION                      1..9
```

-continued

```
                       note = R3 Nidogen-2
source                 1..9
                       mol_type = protein
                       organism = synthetic construct
SEQUENCE: 449
CNLATSLQC                                                                       9

SEQ ID NO: 450         moltype = AA  length = 9
FEATURE                Location/Qualifiers
REGION                 1..9
                       note = R3 Nidogen-2
source                 1..9
                       mol_type = protein
                       organism = synthetic construct
SEQUENCE: 450
CRSPHEPMC                                                                       9

SEQ ID NO: 451         moltype = AA  length = 9
FEATURE                Location/Qualifiers
REGION                 1..9
                       note = R3 Nidogen-2
source                 1..9
                       mol_type = protein
                       organism = synthetic construct
SEQUENCE: 451
CVDKMASVC                                                                       9

SEQ ID NO: 452         moltype = AA  length = 9
FEATURE                Location/Qualifiers
REGION                 1..9
                       note = R3 Nidogen-2
source                 1..9
                       mol_type = protein
                       organism = synthetic construct
SEQUENCE: 452
CYSAPTKSC                                                                       9

SEQ ID NO: 453         moltype = AA  length = 7
FEATURE                Location/Qualifiers
REGION                 1..7
                       note = R3 Nidogen-2
source                 1..7
                       mol_type = protein
                       organism = synthetic construct
SEQUENCE: 453
EAMMHRN                                                                         7

SEQ ID NO: 454         moltype = AA  length = 7
FEATURE                Location/Qualifiers
REGION                 1..7
                       note = R3 Nidogen-2
source                 1..7
                       mol_type = protein
                       organism = synthetic construct
SEQUENCE: 454
LHITPEV                                                                         7

SEQ ID NO: 455         moltype = AA  length = 7
FEATURE                Location/Qualifiers
REGION                 1..7
                       note = R3 Nidogen-2
source                 1..7
                       mol_type = protein
                       organism = synthetic construct
SEQUENCE: 455
LSIRGLT                                                                         7

SEQ ID NO: 456         moltype = AA  length = 7
FEATURE                Location/Qualifiers
REGION                 1..7
                       note = R3 Nidogen-2
source                 1..7
                       mol_type = protein
                       organism = synthetic construct
SEQUENCE: 456
NILSQVN                                                                         7

SEQ ID NO: 457         moltype = AA  length = 7
FEATURE                Location/Qualifiers
```

```
REGION                  1..7
                        note = R3 Nidogen-2
source                  1..7
                        mol_type = protein
                        organism = synthetic construct
SEQUENCE: 457
QLLESRT                                                                      7

SEQ ID NO: 458          moltype = AA  length = 7
FEATURE                 Location/Qualifiers
REGION                  1..7
                        note = R3 Nidogen-2
source                  1..7
                        mol_type = protein
                        organism = synthetic construct
SEQUENCE: 458
QMDAKHM                                                                      7

SEQ ID NO: 459          moltype = AA  length = 7
FEATURE                 Location/Qualifiers
REGION                  1..7
                        note = R3 Nidogen-2
source                  1..7
                        mol_type = protein
                        organism = synthetic construct
SEQUENCE: 459
QTLRPKQ                                                                      7

SEQ ID NO: 460          moltype = AA  length = 7
FEATURE                 Location/Qualifiers
REGION                  1..7
                        note = R3 Nidogen-2
source                  1..7
                        mol_type = protein
                        organism = synthetic construct
SEQUENCE: 460
TIASLLV                                                                      7

SEQ ID NO: 461          moltype = AA  length = 7
FEATURE                 Location/Qualifiers
REGION                  1..7
                        note = R3 Nidogen-2
source                  1..7
                        mol_type = protein
                        organism = synthetic construct
SEQUENCE: 461
WLAAGSQ                                                                      7

SEQ ID NO: 462          moltype = AA  length = 7
FEATURE                 Location/Qualifiers
REGION                  1..7
                        note = R3 Nidogen-2
source                  1..7
                        mol_type = protein
                        organism = synthetic construct
SEQUENCE: 462
ALYLPGR                                                                      7

SEQ ID NO: 463          moltype = AA  length = 7
FEATURE                 Location/Qualifiers
REGION                  1..7
                        note = R3 Nidogen-2
source                  1..7
                        mol_type = protein
                        organism = synthetic construct
SEQUENCE: 463
ARMAFSL                                                                      7

SEQ ID NO: 464          moltype = AA  length = 7
FEATURE                 Location/Qualifiers
REGION                  1..7
                        note = R3 Nidogen-2
source                  1..7
                        mol_type = protein
                        organism = synthetic construct
SEQUENCE: 464
ATYNMSQ                                                                      7

SEQ ID NO: 465          moltype = AA  length = 7
```

```
FEATURE              Location/Qualifiers
REGION               1..7
                     note = R3 Nidogen-2
source               1..7
                     mol_type = protein
                     organism = synthetic construct
SEQUENCE: 465
GLRTMEP                                                                        7

SEQ ID NO: 466       moltype = AA  length = 7
FEATURE              Location/Qualifiers
REGION               1..7
                     note = R3 Nidogen-2
source               1..7
                     mol_type = protein
                     organism = synthetic construct
SEQUENCE: 466
TPWLPTI                                                                        7

SEQ ID NO: 467       moltype = AA  length = 7
FEATURE              Location/Qualifiers
REGION               1..7
                     note = R3 Nidogen-2
source               1..7
                     mol_type = protein
                     organism = synthetic construct
SEQUENCE: 467
YNHTMMY                                                                        7

SEQ ID NO: 468       moltype = AA  length = 9
FEATURE              Location/Qualifiers
REGION               1..9
                     note = R3 Nidogen-2
source               1..9
                     mol_type = protein
                     organism = synthetic construct
SEQUENCE: 468
CSFKMNQKC                                                                      9

SEQ ID NO: 469       moltype = AA  length = 7
FEATURE              Location/Qualifiers
REGION               1..7
                     note = R3 Nidogen-2
source               1..7
                     mol_type = protein
                     organism = synthetic construct
SEQUENCE: 469
LVHPFHG                                                                        7

SEQ ID NO: 470       moltype = AA  length = 9
FEATURE              Location/Qualifiers
REGION               1..9
                     note = R3 Nidogen-2
source               1..9
                     mol_type = protein
                     organism = synthetic construct
SEQUENCE: 470
CSSSAPRIC                                                                      9

SEQ ID NO: 471       moltype = AA  length = 7
FEATURE              Location/Qualifiers
REGION               1..7
                     note = R3 Nidogen-2
source               1..7
                     mol_type = protein
                     organism = synthetic construct
SEQUENCE: 471
HSRLPTP                                                                        7

SEQ ID NO: 472       moltype = AA  length = 9
FEATURE              Location/Qualifiers
REGION               1..9
                     note = Laminin 421/521
source               1..9
                     mol_type = protein
                     organism = synthetic construct
SEQUENCE: 472
CKSPIKGTC                                                                      9
```

| | |
|---|---|
| SEQ ID NO: 473<br>FEATURE<br>REGION<br><br>source | moltype = AA   length = 9<br>Location/Qualifiers<br>1..9<br>note = Laminin 421/521<br>1..9<br>mol_type = protein<br>organism = synthetic construct |

SEQUENCE: 473
CLQKNHKFC                                                               9

| | |
|---|---|
| SEQ ID NO: 474<br>FEATURE<br>REGION<br><br>source | moltype = AA   length = 12<br>Location/Qualifiers<br>1..12<br>note = Laminin 421/521<br>1..12<br>mol_type = protein<br>organism = synthetic construct |

SEQUENCE: 474
CVLKCEDQKY RG                                                          12

| | |
|---|---|
| SEQ ID NO: 475<br>FEATURE<br>REGION<br><br>source | moltype = AA   length = 12<br>Location/Qualifiers<br>1..12<br>note = Laminin 421/521<br>1..12<br>mol_type = protein<br>organism = synthetic construct |

SEQUENCE: 475
DGANMFNIAP AN                                                          12

| | |
|---|---|
| SEQ ID NO: 476<br>FEATURE<br>REGION<br><br>source | moltype = AA   length = 12<br>Location/Qualifiers<br>1..12<br>note = Laminin 421/521<br>1..12<br>mol_type = protein<br>organism = synthetic construct |

SEQUENCE: 476
DRMYSTVPAE GL                                                          12

| | |
|---|---|
| SEQ ID NO: 477<br>FEATURE<br>REGION<br><br>source | moltype = AA   length = 7<br>Location/Qualifiers<br>1..7<br>note = Laminin 421/521<br>1..7<br>mol_type = protein<br>organism = synthetic construct |

SEQUENCE: 477
EAVSTQI                                                                 7

| | |
|---|---|
| SEQ ID NO: 478<br>FEATURE<br>REGION<br><br>source | moltype = AA   length = 12<br>Location/Qualifiers<br>1..12<br>note = Laminin 421/521<br>1..12<br>mol_type = protein<br>organism = synthetic construct |

SEQUENCE: 478
GINLRALDLH AN                                                          12

| | |
|---|---|
| SEQ ID NO: 479<br>FEATURE<br>REGION<br><br>source | moltype = AA   length = 12<br>Location/Qualifiers<br>1..12<br>note = Laminin 421/521<br>1..12<br>mol_type = protein<br>organism = synthetic construct |

SEQUENCE: 479
HQSVTGVRSH FH                                                          12

| | |
|---|---|
| SEQ ID NO: 480<br>FEATURE<br>REGION<br><br>source | moltype = AA   length = 12<br>Location/Qualifiers<br>1..12<br>note = Laminin 421/521<br>1..12<br>mol_type = protein<br>organism = synthetic construct |

SEQUENCE: 480
SVVGWAAPRT AQ                                                          12

```
SEQ ID NO: 481            moltype = AA   length = 12
FEATURE                   Location/Qualifiers
REGION                    1..12
                          note = Laminin 421/521
source                    1..12
                          mol_type = protein
                          organism = synthetic construct
SEQUENCE: 481
TILKPAAQGF AD                                                              12

SEQ ID NO: 482            moltype = AA   length = 7
FEATURE                   Location/Qualifiers
REGION                    1..7
                          note = Laminin 421/521
source                    1..7
                          mol_type = protein
                          organism = synthetic construct
SEQUENCE: 482
TSAVSLR                                                                     7

SEQ ID NO: 483            moltype = AA   length = 12
FEATURE                   Location/Qualifiers
REGION                    1..12
                          note = Laminin 421/521
source                    1..12
                          mol_type = protein
                          organism = synthetic construct
SEQUENCE: 483
TTLWLDRDEA LK                                                              12

SEQ ID NO: 484            moltype = AA   length = 12
FEATURE                   Location/Qualifiers
REGION                    1..12
                          note = Laminin 421/521
source                    1..12
                          mol_type = protein
                          organism = synthetic construct
SEQUENCE: 484
VIADQSKSAV AV                                                              12

SEQ ID NO: 485            moltype = AA   length = 12
FEATURE                   Location/Qualifiers
REGION                    1..12
                          note = Laminin 421/521
source                    1..12
                          mol_type = protein
                          organism = synthetic construct
SEQUENCE: 485
AQNLRVHAWA SL                                                              12

SEQ ID NO: 486            moltype = AA   length = 9
FEATURE                   Location/Qualifiers
REGION                    1..9
                          note = Laminin 421/521
source                    1..9
                          mol_type = protein
                          organism = synthetic construct
SEQUENCE: 486
CPMHQSKTC                                                                   9

SEQ ID NO: 487            moltype = AA   length = 9
FEATURE                   Location/Qualifiers
REGION                    1..9
                          note = Laminin 421/521
source                    1..9
                          mol_type = protein
                          organism = synthetic construct
SEQUENCE: 487
CTDGRNFVC                                                                   9

SEQ ID NO: 488            moltype = AA   length = 9
FEATURE                   Location/Qualifiers
REGION                    1..9
                          note = Laminin 421/521
source                    1..9
                          mol_type = protein
                          organism = synthetic construct
SEQUENCE: 488
```

```
CTGETLLTC                                                                            9

SEQ ID NO: 489          moltype = AA  length = 9
FEATURE                 Location/Qualifiers
REGION                  1..9
                        note = Laminin 421/521
source                  1..9
                        mol_type = protein
                        organism = synthetic construct
SEQUENCE: 489
CTSSSHQTC                                                                            9

SEQ ID NO: 490          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 490
ETGGLAYGSG QK                                                                       12

SEQ ID NO: 491          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 491
GIVPSRHTTG LG                                                                       12

SEQ ID NO: 492          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 492
GWTSDLSRNV RG                                                                       12

SEQ ID NO: 493          moltype = AA  length = 7
FEATURE                 Location/Qualifiers
REGION                  1..7
                        note = Laminin 421/521
source                  1..7
                        mol_type = protein
                        organism = synthetic construct
SEQUENCE: 493
HTQIHRL                                                                              7

SEQ ID NO: 494          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 494
KFADTKLTSL RY                                                                       12

SEQ ID NO: 495          moltype = AA  length = 7
FEATURE                 Location/Qualifiers
REGION                  1..7
                        note = Laminin 421/521
source                  1..7
                        mol_type = protein
                        organism = synthetic construct
SEQUENCE: 495
QLQHVHL                                                                              7

SEQ ID NO: 496          moltype = AA  length = 12
FEATURE                 Location/Qualifiers
REGION                  1..12
                        note = Laminin 421/521
source                  1..12
                        mol_type = protein
                        organism = synthetic construct
```

-continued

```
SEQUENCE: 496
QPTPSQIKFT RT                                                                    12

SEQ ID NO: 497          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 497
RALDRYLPWS PH                                                                    12

SEQ ID NO: 498          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 498
SLPYAASLNS VE                                                                    12

SEQ ID NO: 499          moltype = AA  length = 7
FEATURE                 Location/Qualifiers
REGION                  1..7
                        note = Laminin 421/521
source                  1..7
                        mol_type = protein
                        organism = synthetic construct
SEQUENCE: 499
STNVQRA                                                                           7

SEQ ID NO: 500          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 500
SVLSTGTANQ RH                                                                    12

SEQ ID NO: 501          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 501
SVQTPMWRSL VG                                                                    12

SEQ ID NO: 502          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 502
SWHFTGTPFM NR                                                                    12

SEQ ID NO: 503          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 503
SYTATWSEMS RS                                                                    12

SEQ ID NO: 504          moltype = AA  length = 12
FEATURE                 Location/Qualifiers
REGION                  1..12
                        note = Laminin 421/521
source                  1..12
                        mol_type = protein
```

```
                        organism = synthetic construct
SEQUENCE: 504
TALSHRHEAM RW                                                            12

SEQ ID NO: 505          moltype = AA   length = 7
FEATURE                 Location/Qualifiers
REGION                  1..7
                        note = Laminin 421/521
source                  1..7
                        mol_type = protein
                        organism = synthetic construct
SEQUENCE: 505
TKGIAPK                                                                  7

SEQ ID NO: 506          moltype = AA   length = 12
FEATURE                 Location/Qualifiers
REGION                  1..12
                        note = Laminin 421/521
source                  1..12
                        mol_type = protein
                        organism = synthetic construct
SEQUENCE: 506
TVARSTAQER SI                                                            12

SEQ ID NO: 507          moltype = AA   length = 12
FEATURE                 Location/Qualifiers
REGION                  1..12
                        note = Laminin 421/521
source                  1..12
                        mol_type = protein
                        organism = synthetic construct
SEQUENCE: 507
AVRPLGLPDN HR                                                            12

SEQ ID NO: 508          moltype = AA   length = 9
FEATURE                 Location/Qualifiers
REGION                  1..9
                        note = Laminin 421/521
source                  1..9
                        mol_type = protein
                        organism = synthetic construct
SEQUENCE: 508
CIGGPHRNC                                                                9

SEQ ID NO: 509          moltype = AA   length = 9
FEATURE                 Location/Qualifiers
REGION                  1..9
                        note = Laminin 421/521
source                  1..9
                        mol_type = protein
                        organism = synthetic construct
SEQUENCE: 509
CKSPAIKGC                                                                9

SEQ ID NO: 510          moltype = AA   length = 9
FEATURE                 Location/Qualifiers
REGION                  1..9
                        note = Laminin 421/521
source                  1..9
                        mol_type = protein
                        organism = synthetic construct
SEQUENCE: 510
CNSWKAAKC                                                                9

SEQ ID NO: 511          moltype = AA   length = 12
FEATURE                 Location/Qualifiers
REGION                  1..12
                        note = Laminin 421/521
source                  1..12
                        mol_type = protein
                        organism = synthetic construct
SEQUENCE: 511
DSLYRGMHQP RI                                                            12

SEQ ID NO: 512          moltype = AA   length = 12
FEATURE                 Location/Qualifiers
REGION                  1..12
                        note = Laminin 421/521
source                  1..12
```

```
SEQUENCE: 512
EDRMMTYRYT ST                                                                    12

SEQ ID NO: 513         moltype = AA   length = 12
FEATURE                Location/Qualifiers
REGION                 1..12
                       note = Laminin 421/521
source                 1..12
                       mol_type = protein
                       organism = synthetic construct
SEQUENCE: 513
EVERILTPHV NN                                                                    12

SEQ ID NO: 514         moltype = AA   length = 12
FEATURE                Location/Qualifiers
REGION                 1..12
                       note = Laminin 421/521
source                 1..12
                       mol_type = protein
                       organism = synthetic construct
SEQUENCE: 514
FNSDSRSTHQ ED                                                                    12

SEQ ID NO: 515         moltype = AA   length = 12
FEATURE                Location/Qualifiers
REGION                 1..12
                       note = Laminin 421/521
source                 1..12
                       mol_type = protein
                       organism = synthetic construct
SEQUENCE: 515
HPAWADFFTM SS                                                                    12

SEQ ID NO: 516         moltype = AA   length = 7
FEATURE                Location/Qualifiers
REGION                 1..7
                       note = Laminin 421/521
source                 1..7
                       mol_type = protein
                       organism = synthetic construct
SEQUENCE: 516
IDLSLRS                                                                           7

SEQ ID NO: 517         moltype = AA   length = 12
FEATURE                Location/Qualifiers
REGION                 1..12
                       note = Laminin 421/521
source                 1..12
                       mol_type = protein
                       organism = synthetic construct
SEQUENCE: 517
IDQSGLQKSG MK                                                                    12

SEQ ID NO: 518         moltype = AA   length = 12
FEATURE                Location/Qualifiers
REGION                 1..12
                       note = Laminin 421/521
source                 1..12
                       mol_type = protein
                       organism = synthetic construct
SEQUENCE: 518
LGSSRSPSSF LG                                                                    12

SEQ ID NO: 519         moltype = AA   length = 12
FEATURE                Location/Qualifiers
REGION                 1..12
                       note = Laminin 421/521
source                 1..12
                       mol_type = protein
                       organism = synthetic construct
SEQUENCE: 519
NGHEVQSRAA NR                                                                    12

SEQ ID NO: 520         moltype = AA   length = 12
FEATURE                Location/Qualifiers
REGION                 1..12
                       note = Laminin 421/521
```

-continued

```
source                  1..12
                        mol_type = protein
                        organism = synthetic construct
SEQUENCE: 520
QGWKDRLPIW RY                                                              12

SEQ ID NO: 521          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 521
SHDVANGTSV RT                                                              12

SEQ ID NO: 522          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 522
SPDRTNWGWQ TN                                                              12

SEQ ID NO: 523          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 523
SVESNSKLTM PR                                                              12

SEQ ID NO: 524          moltype = AA  length = 7
FEATURE                 Location/Qualifiers
REGION                  1..7
                        note = Laminin 421/521
source                  1..7
                        mol_type = protein
                        organism = synthetic construct
SEQUENCE: 524
WPMMQTR                                                                     7

SEQ ID NO: 525          moltype = AA  length = 9
FEATURE                 Location/Qualifiers
REGION                  1..9
                        note = Laminin 421/521
source                  1..9
                        mol_type = protein
                        organism = synthetic construct
SEQUENCE: 525
CKSERGPEC                                                                   9

SEQ ID NO: 526          moltype = AA  length = 9
FEATURE                 Location/Qualifiers
REGION                  1..9
                        note = Laminin 421/521
source                  1..9
                        mol_type = protein
                        organism = synthetic construct
SEQUENCE: 526
CQGWPRPMC                                                                   9

SEQ ID NO: 527          moltype = AA  length = 9
FEATURE                 Location/Qualifiers
REGION                  1..9
                        note = Laminin 421/521
source                  1..9
                        mol_type = protein
                        organism = synthetic construct
SEQUENCE: 527
CSRAGLSAC                                                                   9

SEQ ID NO: 528          moltype = AA  length = 9
FEATURE                 Location/Qualifiers
REGION                  1..9
```

```
                            note = Laminin 421/521
source                      1..9
                            mol_type = protein
                            organism = synthetic construct
SEQUENCE: 528
CTWKHRDNC                                                                        9

SEQ ID NO: 529              moltype = AA  length = 12
FEATURE                     Location/Qualifiers
REGION                      1..12
                            note = Laminin 421/521
source                      1..12
                            mol_type = protein
                            organism = synthetic construct
SEQUENCE: 529
GLLDWGSLQG GN                                                                   12

SEQ ID NO: 530              moltype = AA  length = 7
FEATURE                     Location/Qualifiers
REGION                      1..7
                            note = Laminin 421/521
source                      1..7
                            mol_type = protein
                            organism = synthetic construct
SEQUENCE: 530
GPLLFRG                                                                          7

SEQ ID NO: 531              moltype = AA  length = 7
FEATURE                     Location/Qualifiers
REGION                      1..7
                            note = Laminin 421/521
source                      1..7
                            mol_type = protein
                            organism = synthetic construct
SEQUENCE: 531
GSPEKRT                                                                          7

SEQ ID NO: 532              moltype = AA  length = 7
FEATURE                     Location/Qualifiers
REGION                      1..7
                            note = Laminin 421/521
source                      1..7
                            mol_type = protein
                            organism = synthetic construct
SEQUENCE: 532
KASIAYD                                                                          7

SEQ ID NO: 533              moltype = AA  length = 12
FEATURE                     Location/Qualifiers
REGION                      1..12
                            note = Laminin 421/521
source                      1..12
                            mol_type = protein
                            organism = synthetic construct
SEQUENCE: 533
LGYGQGTPHR SN                                                                   12

SEQ ID NO: 534              moltype = AA  length = 12
FEATURE                     Location/Qualifiers
REGION                      1..12
                            note = Laminin 421/521
source                      1..12
                            mol_type = protein
                            organism = synthetic construct
SEQUENCE: 534
QGWEFQVPAR HS                                                                   12

SEQ ID NO: 535              moltype = AA  length = 12
FEATURE                     Location/Qualifiers
REGION                      1..12
                            note = Laminin 421/521
source                      1..12
                            mol_type = protein
                            organism = synthetic construct
SEQUENCE: 535
QTFGYSMFNV RT                                                                   12

SEQ ID NO: 536              moltype = AA  length = 12
FEATURE                     Location/Qualifiers
```

```
REGION                    1..12
                          note = Laminin 421/521
source                    1..12
                          mol_type = protein
                          organism = synthetic construct
SEQUENCE: 536
RNLHYPLNHP FM                                                              12

SEQ ID NO: 537            moltype = AA   length = 7
FEATURE                   Location/Qualifiers
REGION                    1..7
                          note = Laminin 421/521
source                    1..7
                          mol_type = protein
                          organism = synthetic construct
SEQUENCE: 537
TAPRWTQ                                                                     7

SEQ ID NO: 538            moltype = AA   length = 7
FEATURE                   Location/Qualifiers
REGION                    1..7
                          note = Laminin 421/521
source                    1..7
                          mol_type = protein
                          organism = synthetic construct
SEQUENCE: 538
VPSYILR                                                                     7

SEQ ID NO: 539            moltype = AA   length = 7
FEATURE                   Location/Qualifiers
REGION                    1..7
                          note = Laminin 421/521
source                    1..7
                          mol_type = protein
                          organism = synthetic construct
SEQUENCE: 539
WRSPLTT                                                                     7

SEQ ID NO: 540            moltype = AA   length = 9
FEATURE                   Location/Qualifiers
REGION                    1..9
                          note = Laminin 421/521
source                    1..9
                          mol_type = protein
                          organism = synthetic construct
SEQUENCE: 540
CQTSGHHQC                                                                   9

SEQ ID NO: 541            moltype = AA   length = 9
FEATURE                   Location/Qualifiers
REGION                    1..9
                          note = Laminin 421/521
source                    1..9
                          mol_type = protein
                          organism = synthetic construct
SEQUENCE: 541
CSSQAKRSC                                                                   9

SEQ ID NO: 542            moltype = AA   length = 9
FEATURE                   Location/Qualifiers
REGION                    1..9
                          note = Laminin 421/521
source                    1..9
                          mol_type = protein
                          organism = synthetic construct
SEQUENCE: 542
CTAWTRQEC                                                                   9

SEQ ID NO: 543            moltype = AA   length = 12
FEATURE                   Location/Qualifiers
REGION                    1..12
                          note = Laminin 421/521
source                    1..12
                          mol_type = protein
                          organism = synthetic construct
SEQUENCE: 543
EYVKFSHSPR TY                                                              12

SEQ ID NO: 544            moltype = AA   length = 12
```

```
FEATURE                 Location/Qualifiers
REGION                  1..12
                        note = Laminin 421/521
source                  1..12
                        mol_type = protein
                        organism = synthetic construct
SEQUENCE: 544
GGWQSLWDKP EH                                                                   12

SEQ ID NO: 545          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 545
GPMLKNLSDA VT                                                                   12

SEQ ID NO: 546          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 546
NHDQGSLTRW RS                                                                   12

SEQ ID NO: 547          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 547
SLLSVVNTSS KS                                                                   12

SEQ ID NO: 548          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 548
VVPSWPSVHR PP                                                                   12

SEQ ID NO: 549          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 549
WGWNGANMSP RG                                                                   12

SEQ ID NO: 550          moltype = AA  length = 9
FEATURE                 Location/Qualifiers
REGION                  1..9
                        note = Laminin 421/521
source                  1..9
                        mol_type = protein
                        organism = synthetic construct
SEQUENCE: 550
CHNADNNGC                                                                        9

SEQ ID NO: 551          moltype = AA  length = 7
FEATURE                 Location/Qualifiers
REGION                  1..7
                        note = Laminin 421/521
source                  1..7
                        mol_type = protein
                        organism = synthetic construct
SEQUENCE: 551
LPMLRHS                                                                          7
```

```
SEQ ID NO: 552          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 552
NDTGRHASGI SK                                                            12

SEQ ID NO: 553          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 553
QALRTNYSPL NS                                                            12

SEQ ID NO: 554          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 554
TLKAGTRAND GV                                                            12

SEQ ID NO: 555          moltype = AA  length = 9
FEATURE                 Location/Qualifiers
REGION                  1..9
                        note = Laminin 421/521
source                  1..9
                        mol_type = protein
                        organism = synthetic construct
SEQUENCE: 555
CGETTAGKC                                                                 9

SEQ ID NO: 556          moltype = AA  length = 7
FEATURE                 Location/Qualifiers
REGION                  1..7
                        note = Laminin 421/521
source                  1..7
                        mol_type = protein
                        organism = synthetic construct
SEQUENCE: 556
HSTYAPG                                                                   7

SEQ ID NO: 557          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 557
QINWKQADKN AD                                                            12

SEQ ID NO: 558          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 558
ALPWQSGVHG TK                                                            12

SEQ ID NO: 559          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 559
TFGSGRSMPI QY                                                            12
```

```
SEQ ID NO: 560          moltype = AA   length = 12
FEATURE                 Location/Qualifiers
REGION                  1..12
                        note = Laminin 421/521
source                  1..12
                        mol_type = protein
                        organism = synthetic construct
SEQUENCE: 560
VYRNGGGLPL TA                                                              12

SEQ ID NO: 561          moltype = AA   length = 12
FEATURE                 Location/Qualifiers
REGION                  1..12
                        note = Laminin 421/521
source                  1..12
                        mol_type = protein
                        organism = synthetic construct
SEQUENCE: 561
ALKIGPETTI YM                                                              12

SEQ ID NO: 562          moltype = AA   length = 12
FEATURE                 Location/Qualifiers
REGION                  1..12
                        note = Laminin 421/521
source                  1..12
                        mol_type = protein
                        organism = synthetic construct
SEQUENCE: 562
DWTQVRVTNW FL                                                              12

SEQ ID NO: 563          moltype = AA   length = 12
FEATURE                 Location/Qualifiers
REGION                  1..12
                        note = Laminin 421/521
source                  1..12
                        mol_type = protein
                        organism = synthetic construct
SEQUENCE: 563
LGHQNGGRAD MW                                                              12

SEQ ID NO: 564          moltype = AA   length = 7
FEATURE                 Location/Qualifiers
REGION                  1..7
                        note = Laminin 421/521
source                  1..7
                        mol_type = protein
                        organism = synthetic construct
SEQUENCE: 564
MTNSGAK                                                                     7

SEQ ID NO: 565          moltype = AA   length = 7
FEATURE                 Location/Qualifiers
REGION                  1..7
                        note = Laminin 421/521
source                  1..7
                        mol_type = protein
                        organism = synthetic construct
SEQUENCE: 565
WAYTDYM                                                                     7

SEQ ID NO: 566          moltype = AA   length = 12
FEATURE                 Location/Qualifiers
REGION                  1..12
                        note = Laminin 421/521
source                  1..12
                        mol_type = protein
                        organism = synthetic construct
SEQUENCE: 566
AHAAGRDMRQ GT                                                              12

SEQ ID NO: 567          moltype = AA   length = 12
FEATURE                 Location/Qualifiers
REGION                  1..12
                        note = Laminin 421/521
source                  1..12
                        mol_type = protein
                        organism = synthetic construct
SEQUENCE: 567
```

-continued

```
DVIHSSRGAY FE                                                          12

SEQ ID NO: 568         moltype = AA  length = 12
FEATURE                Location/Qualifiers
REGION                 1..12
                       note = Laminin 421/521
source                 1..12
                       mol_type = protein
                       organism = synthetic construct
SEQUENCE: 568
NWTHLGVARL QP                                                          12

SEQ ID NO: 569         moltype = AA  length = 12
FEATURE                Location/Qualifiers
REGION                 1..12
                       note = Laminin 421/521
source                 1..12
                       mol_type = protein
                       organism = synthetic construct
SEQUENCE: 569
SYDGTMLKQV RL                                                          12

SEQ ID NO: 570         moltype = AA  length = 12
FEATURE                Location/Qualifiers
REGION                 1..12
                       note = Laminin 421/521
source                 1..12
                       mol_type = protein
                       organism = synthetic construct
SEQUENCE: 570
WQWRSTELGY RY                                                          12

SEQ ID NO: 571         moltype = AA  length = 12
FEATURE                Location/Qualifiers
REGION                 1..12
                       note = Laminin 421/521
source                 1..12
                       mol_type = protein
                       organism = synthetic construct
SEQUENCE: 571
WSPANGWRHQ TI                                                          12

SEQ ID NO: 572         moltype = AA  length = 9
FEATURE                Location/Qualifiers
REGION                 1..9
                       note = Laminin 421/521
source                 1..9
                       mol_type = protein
                       organism = synthetic construct
SEQUENCE: 572
CLHNGQRSC                                                              9

SEQ ID NO: 573         moltype = AA  length = 9
FEATURE                Location/Qualifiers
REGION                 1..9
                       note = Laminin 421/521
source                 1..9
                       mol_type = protein
                       organism = synthetic construct
SEQUENCE: 573
CTPRSATLC                                                              9

SEQ ID NO: 574         moltype = AA  length = 12
FEATURE                Location/Qualifiers
REGION                 1..12
                       note = Laminin 421/521
source                 1..12
                       mol_type = protein
                       organism = synthetic construct
SEQUENCE: 574
DIMKSPRSNL RS                                                          12

SEQ ID NO: 575         moltype = AA  length = 12
FEATURE                Location/Qualifiers
REGION                 1..12
                       note = Laminin 421/521
source                 1..12
                       mol_type = protein
                       organism = synthetic construct
```

```
SEQUENCE: 575
QTFHEYLNPA RG                                                                    12

SEQ ID NO: 576            moltype = AA  length = 12
FEATURE                   Location/Qualifiers
REGION                    1..12
                          note = Laminin 421/521
source                    1..12
                          mol_type = protein
                          organism = synthetic construct
SEQUENCE: 576
SLNTTWVSPM MK                                                                    12

SEQ ID NO: 577            moltype = AA  length = 7
FEATURE                   Location/Qualifiers
REGION                    1..7
                          note = Laminin 421/521
source                    1..7
                          mol_type = protein
                          organism = synthetic construct
SEQUENCE: 577
AQRMNQA                                                                           7

SEQ ID NO: 578            moltype = AA  length = 7
FEATURE                   Location/Qualifiers
REGION                    1..7
                          note = Laminin 421/521
source                    1..7
                          mol_type = protein
                          organism = synthetic construct
SEQUENCE: 578
GDAQILM                                                                           7

SEQ ID NO: 579            moltype = AA  length = 12
FEATURE                   Location/Qualifiers
REGION                    1..12
                          note = Laminin 421/521
source                    1..12
                          mol_type = protein
                          organism = synthetic construct
SEQUENCE: 579
GHRTLVTSER YL                                                                    12

SEQ ID NO: 580            moltype = AA  length = 12
FEATURE                   Location/Qualifiers
REGION                    1..12
                          note = Laminin 421/521
source                    1..12
                          mol_type = protein
                          organism = synthetic construct
SEQUENCE: 580
LGPSTQGAGQ TR                                                                    12

SEQ ID NO: 581            moltype = AA  length = 12
FEATURE                   Location/Qualifiers
REGION                    1..12
                          note = Laminin 421/521
source                    1..12
                          mol_type = protein
                          organism = synthetic construct
SEQUENCE: 581
TFAAAQAELI MV                                                                    12

SEQ ID NO: 582            moltype = AA  length = 12
FEATURE                   Location/Qualifiers
REGION                    1..12
                          note = Laminin 421/521
source                    1..12
                          mol_type = protein
                          organism = synthetic construct
SEQUENCE: 582
WEEHRVEILP DV                                                                    12

SEQ ID NO: 583            moltype = AA  length = 12
FEATURE                   Location/Qualifiers
REGION                    1..12
                          note = Laminin 421/521
source                    1..12
                          mol_type = protein
```

```
-continued
                    organism = synthetic construct
SEQUENCE: 583
AGAYTSRHAF DE                                                            12

SEQ ID NO: 584      moltype = AA  length = 9
FEATURE             Location/Qualifiers
REGION              1..9
                    note = Laminin 421/521
source              1..9
                    mol_type = protein
                    organism = synthetic construct
SEQUENCE: 584
CGLATNKSC                                                                9

SEQ ID NO: 585      moltype = AA  length = 12
FEATURE             Location/Qualifiers
REGION              1..12
                    note = Laminin 421/521
source              1..12
                    mol_type = protein
                    organism = synthetic construct
SEQUENCE: 585
GDVITAYINP WP                                                            12

SEQ ID NO: 586      moltype = AA  length = 12
FEATURE             Location/Qualifiers
REGION              1..12
                    note = Laminin 421/521
source              1..12
                    mol_type = protein
                    organism = synthetic construct
SEQUENCE: 586
GYDLSRLWGM AS                                                            12

SEQ ID NO: 587      moltype = AA  length = 7
FEATURE             Location/Qualifiers
REGION              1..7
                    note = Laminin 421/521
source              1..7
                    mol_type = protein
                    organism = synthetic construct
SEQUENCE: 587
ANRYLAS                                                                  7

SEQ ID NO: 588      moltype = AA  length = 9
FEATURE             Location/Qualifiers
REGION              1..9
                    note = Laminin 421/521
source              1..9
                    mol_type = protein
                    organism = synthetic construct
SEQUENCE: 588
CKWTQLWGC                                                                9

SEQ ID NO: 589      moltype = AA  length = 9
FEATURE             Location/Qualifiers
REGION              1..9
                    note = Laminin 421/521
source              1..9
                    mol_type = protein
                    organism = synthetic construct
SEQUENCE: 589
CLKDTHLNC                                                                9

SEQ ID NO: 590      moltype = AA  length = 12
FEATURE             Location/Qualifiers
REGION              1..12
                    note = Laminin 421/521
source              1..12
                    mol_type = protein
                    organism = synthetic construct
SEQUENCE: 590
GQPRNIHLPG TH                                                            12

SEQ ID NO: 591      moltype = AA  length = 12
FEATURE             Location/Qualifiers
REGION              1..12
                    note = Laminin 421/521
source              1..12
```

```
SEQUENCE: 591
GSTTHPHFGL PG                                                              12

SEQ ID NO: 592        moltype = AA   length = 12
FEATURE               Location/Qualifiers
REGION                1..12
                      note = Laminin 421/521
source                1..12
                      mol_type = protein
                      organism = synthetic construct
SEQUENCE: 592
GWIQDTFVLG RS                                                              12

SEQ ID NO: 593        moltype = AA   length = 7
FEATURE               Location/Qualifiers
REGION                1..7
                      note = Laminin 421/521
source                1..7
                      mol_type = protein
                      organism = synthetic construct
SEQUENCE: 593
QGHPFIY                                                                     7

SEQ ID NO: 594        moltype = AA   length = 12
FEATURE               Location/Qualifiers
REGION                1..12
                      note = Laminin 421/521
source                1..12
                      mol_type = protein
                      organism = synthetic construct
SEQUENCE: 594
SNPKHVSSLG QM                                                              12

SEQ ID NO: 595        moltype = AA   length = 12
FEATURE               Location/Qualifiers
REGION                1..12
                      note = Laminin 421/521
source                1..12
                      mol_type = protein
                      organism = synthetic construct
SEQUENCE: 595
WGANTTGRTH GG                                                              12

SEQ ID NO: 596        moltype = AA   length = 12
FEATURE               Location/Qualifiers
REGION                1..12
                      note = Laminin 421/521
source                1..12
                      mol_type = protein
                      organism = synthetic construct
SEQUENCE: 596
AQGVWWSEWF AP                                                              12

SEQ ID NO: 597        moltype = AA   length = 9
FEATURE               Location/Qualifiers
REGION                1..9
                      note = Laminin 421/521
source                1..9
                      mol_type = protein
                      organism = synthetic construct
SEQUENCE: 597
CFQPKMNSC                                                                   9

SEQ ID NO: 598        moltype = AA   length = 9
FEATURE               Location/Qualifiers
REGION                1..9
                      note = Laminin 421/521
source                1..9
                      mol_type = protein
                      organism = synthetic construct
SEQUENCE: 598
CWSGNSRSC                                                                   9

SEQ ID NO: 599        moltype = AA   length = 7
FEATURE               Location/Qualifiers
REGION                1..7
                      note = Laminin 421/521
```

```
source                  1..7
                        mol_type = protein
                        organism = synthetic construct
SEQUENCE: 599
FPLKIRT                                                                 7

SEQ ID NO: 600          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 600
LARSSIMAAN NV                                                           12

SEQ ID NO: 601          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 601
AKTQAPSNWS GV                                                           12

SEQ ID NO: 602          moltype = AA  length = 9
FEATURE                 Location/Qualifiers
REGION                  1..9
                        note = Laminin 421/521
source                  1..9
                        mol_type = protein
                        organism = synthetic construct
SEQUENCE: 602
CSVWNSGNC                                                               9

SEQ ID NO: 603          moltype = AA  length = 9
FEATURE                 Location/Qualifiers
REGION                  1..9
                        note = Laminin 421/521
source                  1..9
                        mol_type = protein
                        organism = synthetic construct
SEQUENCE: 603
CTGRISKHC                                                               9

SEQ ID NO: 604          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 604
GAMMNSNNLV AR                                                           12

SEQ ID NO: 605          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 605
GGGYHIFGPL VT                                                           12

SEQ ID NO: 606          moltype = AA  length = 7
FEATURE                 Location/Qualifiers
REGION                  1..7
                        note = Laminin 421/521
source                  1..7
                        mol_type = protein
                        organism = synthetic construct
SEQUENCE: 606
HSFLGAR                                                                 7

SEQ ID NO: 607          moltype = AA  length = 7
FEATURE                 Location/Qualifiers
REGION                  1..7
```

```
                        note = Laminin 421/521
source                  1..7
                        mol_type = protein
                        organism = synthetic construct
SEQUENCE: 607
LLAGPFR                                                                       7

SEQ ID NO: 608          moltype = AA  length = 7
FEATURE                 Location/Qualifiers
REGION                  1..7
                        note = Laminin 421/521
source                  1..7
                        mol_type = protein
                        organism = synthetic construct
SEQUENCE: 608
QTLQTRH                                                                       7

SEQ ID NO: 609          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 609
ALGGEPRKAY QR                                                                12

SEQ ID NO: 610          moltype = AA  length = 9
FEATURE                 Location/Qualifiers
REGION                  1..9
                        note = Laminin 421/521
source                  1..9
                        mol_type = protein
                        organism = synthetic construct
SEQUENCE: 610
CNHLTQKLC                                                                     9

SEQ ID NO: 611          moltype = AA  length = 9
FEATURE                 Location/Qualifiers
REGION                  1..9
                        note = Laminin 421/521
source                  1..9
                        mol_type = protein
                        organism = synthetic construct
SEQUENCE: 611
CTSKLARHC                                                                     9

SEQ ID NO: 612          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 612
AVYPLDLGAG MR                                                                12

SEQ ID NO: 613          moltype = AA  length = 9
FEATURE                 Location/Qualifiers
REGION                  1..9
                        note = Laminin 421/521
source                  1..9
                        mol_type = protein
                        organism = synthetic construct
SEQUENCE: 613
CHRTYNSTC                                                                     9

SEQ ID NO: 614          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 614
LDRNADSVRA VL                                                                12

SEQ ID NO: 615          moltype = AA  length = 12
FEATURE                 Location/Qualifiers
```

```
REGION                     1..12
                           note = Laminin 421/521
source                     1..12
                           mol_type = protein
                           organism = synthetic construct
SEQUENCE: 615
TTNGVPGHDR SP                                                              12

SEQ ID NO: 616             moltype = AA  length = 12
FEATURE                    Location/Qualifiers
REGION                     1..12
                           note = Laminin 421/521
source                     1..12
                           mol_type = protein
                           organism = synthetic construct
SEQUENCE: 616
ADMPQMTLKY GV                                                              12

SEQ ID NO: 617             moltype = AA  length = 7
FEATURE                    Location/Qualifiers
REGION                     1..7
                           note = Laminin 421/521
source                     1..7
                           mol_type = protein
                           organism = synthetic construct
SEQUENCE: 617
AWNGNRS                                                                     7

SEQ ID NO: 618             moltype = AA  length = 7
FEATURE                    Location/Qualifiers
REGION                     1..7
                           note = Laminin 421/521
source                     1..7
                           mol_type = protein
                           organism = synthetic construct
SEQUENCE: 618
GDLLLKR                                                                     7

SEQ ID NO: 619             moltype = AA  length = 7
FEATURE                    Location/Qualifiers
REGION                     1..7
                           note = Laminin 421/521
source                     1..7
                           mol_type = protein
                           organism = synthetic construct
SEQUENCE: 619
VPQIRIK                                                                     7

SEQ ID NO: 620             moltype = AA  length = 7
FEATURE                    Location/Qualifiers
REGION                     1..7
                           note = Laminin 421/521
source                     1..7
                           mol_type = protein
                           organism = synthetic construct
SEQUENCE: 620
SWQMRSY                                                                     7

SEQ ID NO: 621             moltype = AA  length = 12
FEATURE                    Location/Qualifiers
REGION                     1..12
                           note = Laminin 421/521
source                     1..12
                           mol_type = protein
                           organism = synthetic construct
SEQUENCE: 621
YHLGPNQKMR TS                                                              12

SEQ ID NO: 622             moltype = AA  length = 12
FEATURE                    Location/Qualifiers
REGION                     1..12
                           note = Laminin 421/521
source                     1..12
                           mol_type = protein
                           organism = synthetic construct
SEQUENCE: 622
ASHSRPLMNY AP                                                              12

SEQ ID NO: 623             moltype = AA  length = 12
```

```
FEATURE                 Location/Qualifiers
REGION                  1..12
                        note = Laminin 421/521
source                  1..12
                        mol_type = protein
                        organism = synthetic construct
SEQUENCE: 623
QTRWDDGSYQ IS                                                              12

SEQ ID NO: 624          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 624
SLAVANTRFM IR                                                              12

SEQ ID NO: 625          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 625
EGHVWSEYTW GT                                                              12

SEQ ID NO: 626          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 626
ETYKVTRVIS PW                                                              12

SEQ ID NO: 627          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 627
GHPWTEIDFM SS                                                              12

SEQ ID NO: 628          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 628
KQELSDNLAS HR                                                              12

SEQ ID NO: 629          moltype = AA  length = 12
FEATURE                 Location/Qualifiers
REGION                  1..12
                        note = Laminin 421/521
source                  1..12
                        mol_type = protein
                        organism = synthetic construct
SEQUENCE: 629
SFRNLEKLSL WS                                                              12

SEQ ID NO: 630          moltype = AA  length = 7
FEATURE                 Location/Qualifiers
REGION                  1..7
                        note = Laminin 421/521
source                  1..7
                        mol_type = protein
                        organism = synthetic construct
SEQUENCE: 630
GDLWNVP                                                                     7
```

```
SEQ ID NO: 631         moltype = AA  length = 7
FEATURE                Location/Qualifiers
REGION                 1..7
                       note = Laminin 421/521
source                 1..7
                       mol_type = protein
                       organism = synthetic construct
SEQUENCE: 631
GPKNHHQ                                                                    7

SEQ ID NO: 632         moltype = AA  length = 12
FEATURE                Location/Qualifiers
REGION                 1..12
                       note = Laminin 421/521
source                 1..12
                       mol_type = protein
                       organism = synthetic construct
SEQUENCE: 632
GSGFRNEEHS AH                                                             12

SEQ ID NO: 633         moltype = AA  length = 12
FEATURE                Location/Qualifiers
REGION                 1..12
                       note = Laminin 421/521
source                 1..12
                       mol_type = protein
                       organism = synthetic construct
SEQUENCE: 633
NNNAAMQNHG VR                                                             12

SEQ ID NO: 634         moltype = AA  length = 7
FEATURE                Location/Qualifiers
REGION                 1..7
                       note = Laminin 421/521
source                 1..7
                       mol_type = protein
                       organism = synthetic construct
SEQUENCE: 634
RAQAHQV                                                                    7

SEQ ID NO: 635         moltype = AA  length = 9
FEATURE                Location/Qualifiers
REGION                 1..9
                       note = Laminin 421/521
source                 1..9
                       mol_type = protein
                       organism = synthetic construct
SEQUENCE: 635
CSLANPATC                                                                  9

SEQ ID NO: 636         moltype = AA  length = 12
FEATURE                Location/Qualifiers
REGION                 1..12
                       note = Laminin 421/521
source                 1..12
                       mol_type = protein
                       organism = synthetic construct
SEQUENCE: 636
GEPLTRFPNS DS                                                             12

SEQ ID NO: 637         moltype = AA  length = 12
FEATURE                Location/Qualifiers
REGION                 1..12
                       note = Laminin 421/521
source                 1..12
                       mol_type = protein
                       organism = synthetic construct
SEQUENCE: 637
KPILWNRSLN AL                                                             12

SEQ ID NO: 638         moltype = AA  length = 12
FEATURE                Location/Qualifiers
REGION                 1..12
                       note = Laminin 421/521
source                 1..12
                       mol_type = protein
                       organism = synthetic construct
SEQUENCE: 638
GFADVIHRKW SS                                                             12
```

| | | |
|---|---|---|
| SEQ ID NO: 639<br>FEATURE<br>REGION<br><br>source | moltype = AA   length = 12<br>Location/Qualifiers<br>1..12<br>note = Laminin 421/521<br>1..12<br>mol_type = protein<br>organism = synthetic construct | |
| SEQUENCE: 639<br>HQSLAGVPWS RH | | 12 |
| SEQ ID NO: 640<br>FEATURE<br>REGION<br><br>source | moltype = AA   length = 12<br>Location/Qualifiers<br>1..12<br>note = Laminin 421/521<br>1..12<br>mol_type = protein<br>organism = synthetic construct | |
| SEQUENCE: 640<br>VPVFLDQARV MK | | 12 |
| SEQ ID NO: 641<br>FEATURE<br>REGION<br><br>source | moltype = AA   length = 12<br>Location/Qualifiers<br>1..12<br>note = Laminin 421/521<br>1..12<br>mol_type = protein<br>organism = synthetic construct | |
| SEQUENCE: 641<br>DDLLTAPRLG VW | | 12 |
| SEQ ID NO: 642<br>FEATURE<br>REGION<br><br>source | moltype = AA   length = 12<br>Location/Qualifiers<br>1..12<br>note = Laminin 421/521<br>1..12<br>mol_type = protein<br>organism = synthetic construct | |
| SEQUENCE: 642<br>SDRGKTVLHG QI | | 12 |
| SEQ ID NO: 643<br>FEATURE<br>REGION<br><br>source | moltype = AA   length = 9<br>Location/Qualifiers<br>1..9<br>note = Laminin 421/521<br>1..9<br>mol_type = protein<br>organism = synthetic construct | |
| SEQUENCE: 643<br>CGITQTTTC | | 9 |
| SEQ ID NO: 644<br>FEATURE<br>REGION<br><br>source | moltype = AA   length = 9<br>Location/Qualifiers<br>1..9<br>note = Laminin 421/521<br>1..9<br>mol_type = protein<br>organism = synthetic construct | |
| SEQUENCE: 644<br>CHQRQQTYC | | 9 |
| SEQ ID NO: 645<br>FEATURE<br>REGION<br><br>source | moltype = AA   length = 12<br>Location/Qualifiers<br>1..12<br>note = Laminin 421/521<br>1..12<br>mol_type = protein<br>organism = synthetic construct | |
| SEQUENCE: 645<br>EYWHQRGSWF HR | | 12 |
| SEQ ID NO: 646<br>FEATURE<br>REGION<br><br>source<br><br>SEQUENCE: 646 | moltype = AA   length = 7<br>Location/Qualifiers<br>1..7<br>note = Laminin 421/521<br>1..7<br>mol_type = protein<br>organism = synthetic construct | |

YTPRNQL                                                                                     7

SEQ ID NO: 647          moltype = AA   length = 9
FEATURE                 Location/Qualifiers
REGION                  1..9
                        note = Laminin 421/521
source                  1..9
                        mol_type = protein
                        organism = synthetic construct
SEQUENCE: 647
CTKSPSNSC                                                                                   9

SEQ ID NO: 648          moltype = AA   length = 7
FEATURE                 Location/Qualifiers
REGION                  1..7
                        note = Laminin 421/521
source                  1..7
                        mol_type = protein
                        organism = synthetic construct
SEQUENCE: 648
WAFKAPQ                                                                                     7

SEQ ID NO: 649          moltype = AA   length = 12
FEATURE                 Location/Qualifiers
REGION                  1..12
                        note = Laminin 421/521
source                  1..12
                        mol_type = protein
                        organism = synthetic construct
SEQUENCE: 649
GSLDMGNNKQ PV                                                                              12

SEQ ID NO: 650          moltype = AA   length = 12
FEATURE                 Location/Qualifiers
REGION                  1..12
                        note = Laminin 421/521
source                  1..12
                        mol_type = protein
                        organism = synthetic construct
SEQUENCE: 650
AVVSQNQMSQ QK                                                                              12

SEQ ID NO: 651          moltype = AA   length = 9
FEATURE                 Location/Qualifiers
REGION                  1..9
                        note = Laminin 421/521
source                  1..9
                        mol_type = protein
                        organism = synthetic construct
SEQUENCE: 651
CLNQKWEAC                                                                                   9

SEQ ID NO: 652          moltype = AA   length = 7
FEATURE                 Location/Qualifiers
REGION                  1..7
                        note = Laminin 421/521
source                  1..7
                        mol_type = protein
                        organism = synthetic construct
SEQUENCE: 652
WPVRNLL                                                                                     7

SEQ ID NO: 653          moltype = AA   length = 12
FEATURE                 Location/Qualifiers
REGION                  1..12
                        note = Laminin 421/521
source                  1..12
                        mol_type = protein
                        organism = synthetic construct
SEQUENCE: 653
GYRSFIHENW SI                                                                              12

SEQ ID NO: 654          moltype = AA   length = 12
FEATURE                 Location/Qualifiers
REGION                  1..12
                        note = Laminin 421/521
source                  1..12
                        mol_type = protein
                        organism = synthetic construct -continued

| | | |
|---|---|---|
| SEQUENCE: 654 SGWEGKTHQG VR | | 12 |
| SEQ ID NO: 655 FEATURE REGION source | moltype = AA length = 12 Location/Qualifiers 1..12 note = Laminin 421/521 1..12 mol_type = protein organism = synthetic construct | |
| SEQUENCE: 655 LQSNAADHHQ GM | | 12 |
| SEQ ID NO: 656 FEATURE REGION source | moltype = AA length = 12 Location/Qualifiers 1..12 note = Laminin 421/521 1..12 mol_type = protein organism = synthetic construct | |
| SEQUENCE: 656 ATSKYPNSWA QT | | 12 |
| SEQ ID NO: 657 FEATURE REGION source | moltype = AA length = 12 Location/Qualifiers 1..12 note = Laminin 421/521 1..12 mol_type = protein organism = synthetic construct | |
| SEQUENCE: 657 DRLTPITWDW SR | | 12 |
| SEQ ID NO: 658 FEATURE REGION source | moltype = AA length = 12 Location/Qualifiers 1..12 note = Laminin 421/521 1..12 mol_type = protein organism = synthetic construct | |
| SEQUENCE: 658 WTKHNTPAHH LS | | 12 |
| SEQ ID NO: 659 FEATURE REGION source | moltype = AA length = 12 Location/Qualifiers 1..12 note = Laminin 421/521 1..12 mol_type = protein organism = synthetic construct | |
| SEQUENCE: 659 WNANYGTMTR HA | | 12 |
| SEQ ID NO: 660 FEATURE REGION source | moltype = AA length = 7 Location/Qualifiers 1..7 note = Laminin 421/521 1..7 mol_type = protein organism = synthetic construct | |
| SEQUENCE: 660 HASNQRV | | 7 |
| SEQ ID NO: 661 FEATURE REGION source | moltype = AA length = 7 Location/Qualifiers 1..7 note = Laminin 421/521 1..7 mol_type = protein organism = synthetic construct | |
| SEQUENCE: 661 GRTIHSM | | 7 |
| SEQ ID NO: 662 FEATURE REGION source | moltype = AA length = 12 Location/Qualifiers 1..12 note = Laminin 421/521 1..12 mol_type = protein | |

-continued

```
SEQUENCE: 662
RLVTASMVSP SF                                                              12

SEQ ID NO: 663         moltype = AA  length = 12
FEATURE                Location/Qualifiers
REGION                 1..12
                       note = Laminin 421/521
source                 1..12
                       mol_type = protein
                       organism = synthetic construct
SEQUENCE: 663
DGQVSDHSYV QW                                                              12

SEQ ID NO: 664         moltype = AA  length = 12
FEATURE                Location/Qualifiers
REGION                 1..12
                       note = Laminin 421/521
source                 1..12
                       mol_type = protein
                       organism = synthetic construct
SEQUENCE: 664
KISMNRLHAN FT                                                              12

SEQ ID NO: 665         moltype = AA  length = 12
FEATURE                Location/Qualifiers
REGION                 1..12
                       note = Laminin 421/521
source                 1..12
                       mol_type = protein
                       organism = synthetic construct
SEQUENCE: 665
WDLPTLRKTK QA                                                              12

SEQ ID NO: 666         moltype = AA  length = 7
FEATURE                Location/Qualifiers
REGION                 1..7
                       note = Laminin 421/521
source                 1..7
                       mol_type = protein
                       organism = synthetic construct
SEQUENCE: 666
WVAAERR                                                                     7

SEQ ID NO: 667         moltype = AA  length = 12
FEATURE                Location/Qualifiers
REGION                 1..12
                       note = Laminin 421/521
source                 1..12
                       mol_type = protein
                       organism = synthetic construct
SEQUENCE: 667
MTHSAHNSQK TN                                                              12

SEQ ID NO: 668         moltype = AA  length = 7
FEATURE                Location/Qualifiers
REGION                 1..7
                       note = Laminin 421/521
source                 1..7
                       mol_type = protein
                       organism = synthetic construct
SEQUENCE: 668
WGLKLPH                                                                     7

SEQ ID NO: 669         moltype = AA  length = 7
FEATURE                Location/Qualifiers
REGION                 1..7
                       note = Laminin 421/521
source                 1..7
                       mol_type = protein
                       organism = synthetic construct
SEQUENCE: 669
QGWFRHS                                                                     7

SEQ ID NO: 670         moltype = AA  length = 7
FEATURE                Location/Qualifiers
REGION                 1..7
                       note = Laminin 421/521
source                 1..7
```

-continued

```
                            mol_type = protein
                            organism = synthetic construct
SEQUENCE: 670
IPVGERK                                                                  7

SEQ ID NO: 671              moltype = AA   length = 9
FEATURE                     Location/Qualifiers
REGION                      1..9
                            note = Laminin 421/521
source                      1..9
                            mol_type = protein
                            organism = synthetic construct
SEQUENCE: 671
CMNKIQRDC                                                                9

SEQ ID NO: 672              moltype = AA   length = 12
FEATURE                     Location/Qualifiers
REGION                      1..12
                            note = Laminin 421/521
source                      1..12
                            mol_type = protein
                            organism = synthetic construct
SEQUENCE: 672
KALGYSLVGG EW                                                           12

SEQ ID NO: 673              moltype = AA   length = 12
FEATURE                     Location/Qualifiers
REGION                      1..12
                            note = Laminin 421/521
source                      1..12
                            mol_type = protein
                            organism = synthetic construct
SEQUENCE: 673
APKVTNARPT QL                                                           12

SEQ ID NO: 674              moltype = AA   length = 12
FEATURE                     Location/Qualifiers
REGION                      1..12
                            note = Laminin 421/521
source                      1..12
                            mol_type = protein
                            organism = synthetic construct
SEQUENCE: 674
AWVEAQNASN PS                                                           12

SEQ ID NO: 675              moltype = AA   length = 9
FEATURE                     Location/Qualifiers
REGION                      1..9
                            note = Laminin 421/521
source                      1..9
                            mol_type = protein
                            organism = synthetic construct
SEQUENCE: 675
CSKHNHSRC                                                                9

SEQ ID NO: 676              moltype = AA   length = 12
FEATURE                     Location/Qualifiers
REGION                      1..12
                            note = Laminin 421/521
source                      1..12
                            mol_type = protein
                            organism = synthetic construct
SEQUENCE: 676
GKPDHRLVSL WR                                                           12

SEQ ID NO: 677              moltype = AA   length = 9
FEATURE                     Location/Qualifiers
REGION                      1..9
                            note = Laminin 421/521
source                      1..9
                            mol_type = protein
                            organism = synthetic construct
SEQUENCE: 677
CSHHKLKQC                                                                9

SEQ ID NO: 678              moltype = AA   length = 12
FEATURE                     Location/Qualifiers
REGION                      1..12
                            note = Laminin 421/521
```

-continued

| | | |
|---|---|---|
| source | 1..12<br>mol_type = protein<br>organism = synthetic construct | |
| SEQUENCE: 678<br>GGYDLPWANW QN | | 12 |
| SEQ ID NO: 679<br>FEATURE<br>REGION<br><br>source | moltype = AA   length = 12<br>Location/Qualifiers<br>1..12<br>note = nerve-binding peptide<br>1..12<br>mol_type = protein<br>organism = synthetic construct | |
| SEQUENCE: 679<br>GWQMFPPMQN TR | | 12 |
| SEQ ID NO: 680<br>FEATURE<br>REGION<br><br>source | moltype = AA   length = 12<br>Location/Qualifiers<br>1..12<br>note = nerve-binding peptide<br>1..12<br>mol_type = protein<br>organism = synthetic construct | |
| SEQUENCE: 680<br>SSLY

```
                        note = nerve-binding peptide
source                  1..12
                        mol_type = protein
                        organism = synthetic construct
SEQUENCE: 686
GWNEATNSAR HT                                                           12

SEQ ID NO: 687          mo

```
REGION                  1..12
                        note = nerve-binding peptide
source                  1..12
                        mol_type = protein
                        organism = synthetic construct
SEQUENC

```
FEATURE                 Location/Qualifiers
REGION                  1..12
                        note = nerve-binding peptide
source                  1..12
                        mol_type = protein
                        organism = synthetic construct
SEQUENCE: 702
KTTSMTALTM GL                                                        12

SEQ ID NO: 703          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 703
VNYQTPWNKH WY                                                        12

SEQ ID NO: 704          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 704
VESGHAYSVS SW                                                        12

SEQ ID NO: 705          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 705
VRSDMVSGGL QK                                                        12

SEQ ID NO: 706          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 706
YANGIEAKDS SR                                                        12

SEQ ID NO: 707          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 707
YAWDTVASRN YK                                                        12

SEQ ID NO: 708          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 708
LQTHSITYRH ER                                                        12

SEQ ID NO: 709          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 709
SLGSSFVQGG EL                                                        12
```

| | | |
|---|---|---|
| SEQ ID NO: 710<br>FEATURE<br>REGION<br><br>source | moltype = AA  length = 12<br>Location/Qualifiers<br>1..12<br>note = nerve-binding peptide<br>1..12<br>mol_type = protein<br>organism = synthetic construct | |
| SEQUENCE: 710<br>WEKHTGPLSR YL | | 12 |
| SEQ ID NO: 711<br>FEATURE<br>REGION<br><br>source | moltype = AA  length = 12<br>Location/Qualifiers<br>1..12<br>note = nerve-binding peptide<br>1..12<br>mol_type = protein<br>organism = synthetic construct | |
| SEQUENCE: 711<br>AFRFEFQVPD SH | | 12 |
| SEQ ID NO: 712<br>FEATURE<br>REGION<br><br>source | moltype = AA  length = 12<br>Location/Qualifiers<br>1..12<br>note = nerve-binding peptide<br>1..12<br>mol_type = protein<br>organism = synthetic construct | |
| SEQUENCE: 712<br>GHAHSLTQNP LF | | 12 |
| SEQ ID NO: 713<br>FEATURE<br>REGION<br><br>source | moltype = AA  length = 12<br>Location/Qualifiers<br>1..12<br>note = nerve-binding peptide<br>1..12<br>mol_type = protein<br>organism = synthetic construct | |
| SEQUENCE: 713<br>GLTIMSSRHS LQ | | 12 |
| SEQ ID NO: 714<br>FEATURE<br>REGION<br><br>source | moltype = AA  length = 12<br>Location/Qualifiers<br>1..12<br>note = nerve-binding peptide<br>1..12<br>mol_type = protein<br>organism = synthetic construct | |
| SEQUENCE: 714<br>NGMNWLQVHQ LS | | 12 |
| SEQ ID NO: 715<br>FEATURE<br>REGION<br><br>source | moltype = AA  length = 12<br>Location/Qualifiers<br>1..12<br>note = nerve-binding peptide<br>1..12<br>mol_type = protein<br>organism = synthetic construct | |
| SEQUENCE: 715<br>WSGGMEDNSN RL | | 12 |
| SEQ ID NO: 716<br>FEATURE<br>REGION<br><br>source | moltype = AA  length = 12<br>Location/Qualifiers<br>1..12<br>note = nerve-binding peptide<br>1..12<br>mol_type = protein<br>organism = synthetic construct | |
| SEQUENCE: 716<br>AIMSYNSPWI QG | | 12 |
| SEQ ID NO: 717<br>FEATURE<br>REGION<br><br>source | moltype = AA  length = 12<br>Location/Qualifiers<br>1..12<br>note = nerve-binding peptide<br>1..12<br>mol_type = protein<br>organism = synthetic construct | |
| SEQUENCE: 717<br>DVMQMFHQVH FY | | 12 |

```
SEQ ID NO: 718          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 718
QANLYYWDPS DL                                                        12

SEQ ID NO: 719          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 719
QRATNDILIR GW                                                        12

SEQ ID NO: 720          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 720
SPMANVWFNR LS                                                        12

SEQ ID NO: 721          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 721
YSANSNPKKS LM                                                        12

SEQ ID NO: 722          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 722
ALNHNGPVKT GL                                                        12

SEQ ID NO: 723          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 723
DASQYPLVSG LW                                                        12

SEQ ID NO: 724          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 724
EPWQSRDKVI EE                                                        12

SEQ ID NO: 725          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 725
```

-continued

```
GLWDGKGRIV EV                                                    12

SEQ ID NO: 726          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 726
GTVSYMVKMD NN                                                    12

SEQ ID NO: 727          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 727
SLQLWNSEKV TT                                                    12

SEQ ID NO: 728          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 728
WVGPDIIAQM RI                                                    12

SEQ ID NO: 729          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 729
EIIVMSGSNV TN                                                    12

SEQ ID NO: 730          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 730
HSGAYTIQAS YK                                                    12

SEQ ID NO: 731          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 731
MLKMERPGRM AY                                                    12

SEQ ID NO: 732          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 732
SDHTFKRVMF RW                                                    12

SEQ ID NO: 733          moltype = AA  length = 12
FEATURE                 Location/Qualifiers
REGION                  1..12
                        note = nerve-binding peptide
source                  1..12
                        mol_type = protein
                        organism = synthetic construct
```

```
SEQUENCE: 733
EMVPMKFLMM AK                                                     12

SEQ ID NO: 734          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 734
NTEYSRYTSI WK                                                     12

SEQ ID NO: 735          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 735
TDNGSFLGKL TS                                                     12

SEQ ID NO: 736          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 736
TEWMVRASSI GE                                                     12

SEQ ID NO: 737          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 737
VPVPKKMSLD PT                                                     12

SEQ ID NO: 738          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 738
WPLKRFEQLP LK                                                     12

SEQ ID NO: 739          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 739
MLRHVDLTEP NA                                                     12

SEQ ID NO: 740          moltype = AA  length = 12
FEATURE                 Location/Qualifiers
REGION                  1..12
                        note = nerve-binding peptide
source                  1..12
                        mol_type = protein
                        organism = synthetic construct
SEQUENCE: 740
QSTLGVHMLR VS                                                     12

SEQ ID NO: 741          moltype = AA  length = 12
FEATURE                 Location/Qualifiers
REGION                  1..12
                        note = nerve-binding peptide
source                  1..12
                        mol_type = protein
```

-continued

```
                          organism = synthetic construct
SEQUENCE: 741
RTVITNEMLL LV                                                              12

SEQ ID NO: 742            moltype = AA  length = 12
FEATURE                   Location/Qualifiers
REGION                    1..12
                          note = nerve-binding peptide
source                    1..12
                          mol_type = protein
                          organism = synthetic construct
SEQUENCE: 742
SEPIEKGSRT IV                                                              12

SEQ ID NO: 743            moltype = AA  length = 12
FEATURE                   Location/Qualifiers
REGION                    1..12
                          note = nerve-binding peptide
source                    1..12
                          mol_type = protein
                          organism = synthetic construct
SEQUENCE: 743
TLNARDQLSI NG                                                              12

SEQ ID NO: 744            moltype = AA  length = 12
FEATURE                   Location/Qualifiers
REGION                    1..12
                          note = nerve-binding peptide
source                    1..12
                          mol_type = protein
                          organism = synthetic construct
SEQUENCE: 744
GTALNLQKDI NK                                                              12

SEQ ID NO: 745            moltype = AA  length = 12
FEATURE                   Location/Qualifiers
REGION                    1..12
                          note = nerve-binding peptide
source                    1..12
                          mol_type = protein
                          organism = synthetic construct
SEQUENCE: 745
SGWHLVMSMS IG                                                              12

SEQ ID NO: 746            moltype = AA  length = 12
FEATURE                   Location/Qualifiers
REGION                    1..12
                          note = nerve-binding peptide
source                    1..12
                          mol_type = protein
                          organism = synthetic construct
SEQUENCE: 746
TSAHHDRTLA GS                                                              12

SEQ ID NO: 747            moltype = AA  length = 17
FEATURE                   Location/Qualifiers
REGION                    1..17
                          note = HNP401-N-2 with GG linker
MOD_RES                   1
                          note = 5FAM
MOD_RES                   17
                          note = NH2
source                    1..17
                          mol_type = protein
                          organism = synthetic construct
SEQUENCE: 747
QVPWEEPYYV VKKSSGG                                                         17

SEQ ID NO: 748            moltype = AA  length = 20
FEATURE                   Location/Qualifiers
REGION                    1..20
                          note = HNP401with GCC linker
MOD_RES                   1
                          note = Ac
MOD_RES                   20
                          note = CONH2
source                    1..20
                          mol_type = protein
                          organism = synthetic construct
```

```
SEQUENCE: 748
SGQVPWEEPY YVVKKSSGGC                                                        20

SEQ ID NO: 749         moltype = AA  length = 17
FEATURE                Location/Qualifiers
REGION                 1..17
                       note = NP41
MOD_RES                1
                       note = Ac
source                 1..17
                       mol_type = protein
                       organism = synthetic construct
SEQUENCE: 749
SHSNTQTLAK APEHTGK                                                           17
```